(12) United States Patent
Huse et al.

(10) Patent No.: US 12,648,963 B2
(45) Date of Patent: Jun. 9, 2026

(54) MiR200c-EpCAM AXIS REPROGRAMED IMMUNE CELLS FOR ENHANCED ANTI-TUMOR FUNCTION

(71) Applicants: Memorial Sloan-Kettering Cancer Center, New York, NY (US); Sloan-Kettering Institute for Cancer Research, New York, NY (US); Memorial Hospital for Cancer and Allied Diseases, New York, NY (US)

(72) Inventors: Morgan Huse, New York, NY (US); Minggang Zhang, New York, NY (US)

(73) Assignees: Memorial Sloan-Kettering Cancer Center, New York, NY (US); Memorial Hospital for Cancer and Allied Diseases, New York, NY (US); Sloan-Kettering Institute for Cancer Research, New York, NY (US)

( * ) Notice: Subject to any disclaimer, the term of this patent is extended or adjusted under 35 U.S.C. 154(b) by 476 days.

(21) Appl. No.: 18/546,936

(22) PCT Filed: Feb. 18, 2022

(86) PCT No.: PCT/US2022/016921
§ 371 (c)(1),
(2) Date: Aug. 17, 2023

(87) PCT Pub. No.: WO2022/178211
PCT Pub. Date: Aug. 25, 2022

(65) Prior Publication Data
US 2024/0131073 A1 Apr. 25, 2024
US 2024/0226161 A9 Jul. 11, 2024

Related U.S. Application Data

(60) Provisional application No. 63/242,554, filed on Sep. 10, 2021, provisional application No. 63/151,206, filed on Feb. 19, 2021.

(51) Int. Cl.
| | |
|---|---|
| *A61K 35/17* | (2025.01) |
| *A61K 9/00* | (2006.01) |
| *A61K 40/11* | (2025.01) |
| *A61K 40/31* | (2025.01) |
| *A61K 40/42* | (2025.01) |
| *A61K 45/06* | (2006.01) |
| *A61P 35/00* | (2006.01) |
| *C07K 14/705* | (2006.01) |
| *C12N 5/0783* | (2010.01) |
| *C12N 15/113* | (2010.01) |
| *C12N 15/86* | (2006.01) |

(52) U.S. Cl.
CPC ............ *A61K 35/17* (2013.01); *A61K 9/0019* (2013.01); *A61K 40/11* (2025.01); *A61K 40/31* (2025.01); *A61K 40/42* (2025.01); *A61K 40/4211* (2025.01); *A61K 40/4254* (2025.01); *A61K 40/4257* (2025.01); *A61K 40/4258* (2025.01); *A61K 40/4273* (2025.01); *A61K 45/06* (2013.01); *A61P 35/00* (2018.01); *C07K 14/705* (2013.01); *C12N 5/0636* (2013.01); *C12N 15/113* (2013.01); *C12N 15/86* (2013.01); *A61K 2239/28* (2023.05); *A61K 2239/31* (2023.05); *A61K 2239/38* (2023.05); *A61K 2239/57* (2023.05); *C12N 2310/141* (2013.01); *C12N 2740/10043* (2013.01)

(58) Field of Classification Search
CPC ..................................................... A61K 35/17
See application file for complete search history.

(56) References Cited

U.S. PATENT DOCUMENTS

| | | |
|---|---|---|
| 2009/0138977 A1 | 5/2009 | Domon et al. |
| 2009/0163435 A1 | 6/2009 | Bader et al. |

FOREIGN PATENT DOCUMENTS

| | | |
|---|---|---|
| WO | WO-2020/018964 A1 | 1/2020 |

OTHER PUBLICATIONS

Zhang et al. Sep. 15, 2021, Science Translational Medicine, vol. 13, Issue 611, https://doi.org/10.1126/scitranslmed.abg4328.*
International Search Report and Written Opinion for PCT/US2022/016921 dated Aug. 26, 2022, 12 pages.
Zhou, J et al. "LncRNATCF7 promotes the growth and self-renewal of glioma cells via suppressing the miR-2000-EpCAM axis," pp. 203-208. Biomedicine & Pharmacotherapy. vol. 97. Jan. 2018.

* cited by examiner

*Primary Examiner* — Prema M Mertz
(74) *Attorney, Agent, or Firm* — Foley & Lardner LLP

(57) ABSTRACT

Provided herein are compositions, kits, and methods for manufacturing cells for adoptive cell therapy comprising engineered immune cells that overexpress miR200c and/or EpCAM.

8 Claims, 66 Drawing Sheets
Specification includes a Sequence Listing.

FIG. 5F

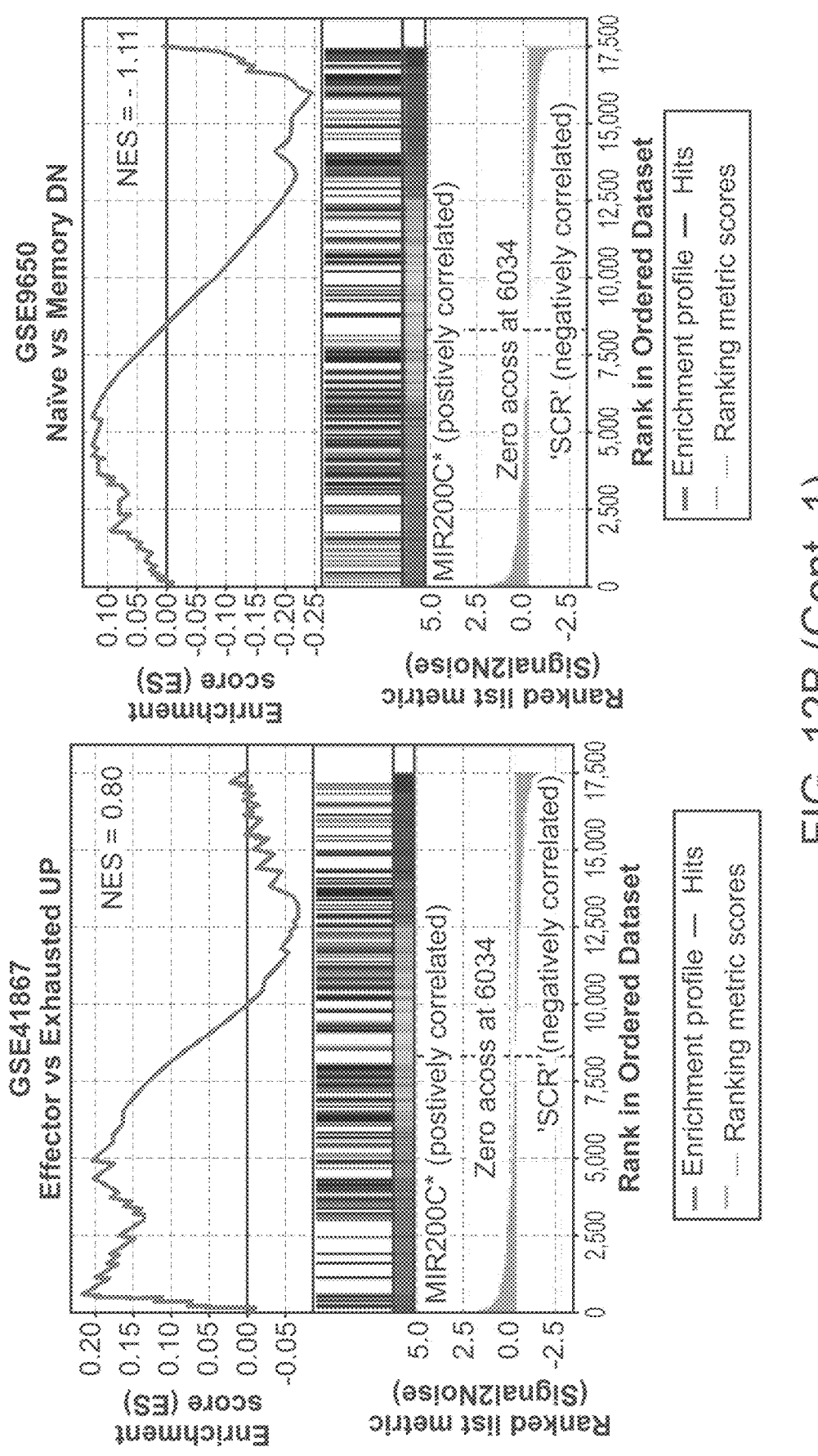
FIG. 12B (Cont. 1)

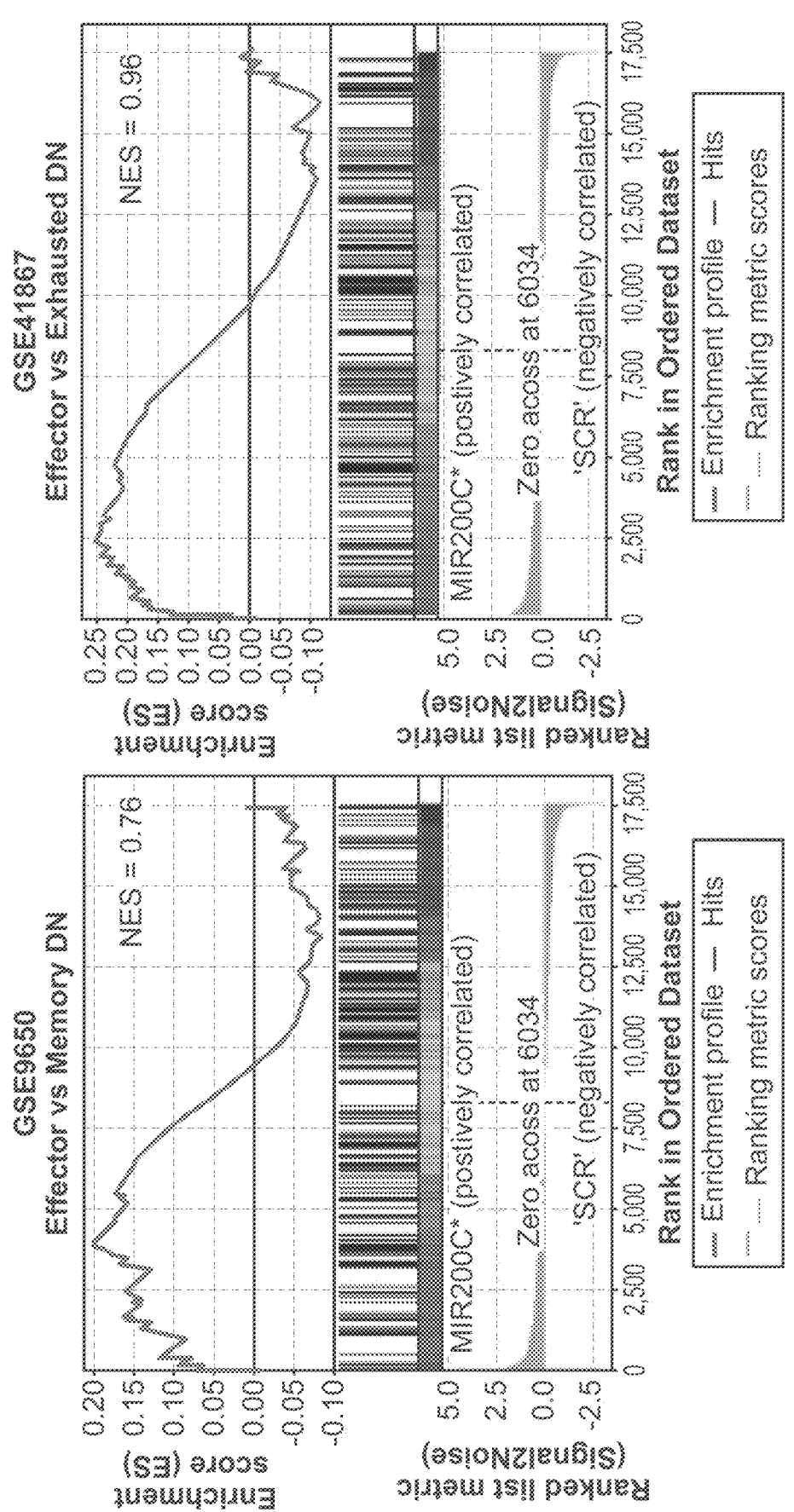
FIG. 12B (Cont. 2)

FIG. 13C

MiR200c-EpCAM AXIS REPROGRAMED IMMUNE CELLS FOR ENHANCED ANTI-TUMOR FUNCTION

CROSS-REFERENCE TO RELATED APPLICATIONS

This application is a U.S. National Stage Application of PCT/US2022/016921, filed Feb. 18, 2022, which claims the benefit of and priority to U.S. Provisional Patent Application No. 63/151,206, filed Feb. 19, 2021, and U.S. Provisional Patent Application No. 63/242,554, filed Sep. 10, 2021, the entire contents of which are incorporated herein by reference.

STATEMENT OF GOVERNMENT SUPPORT

This invention was made with government support under CA008748 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 25, 2022, is named 115872-2462_SL.txt and is 17,106 bytes in size.

TECHNICAL FIELD

The present technology relates to compositions, kits, and methods for manufacturing cells for adoptive cell therapy comprising engineered immune cells that overexpress miR200c and/or EpCAM.

BACKGROUND

The following description of the background of the present technology is provided simply as an aid in understanding the present technology and is not admitted to describe or constitute prior art to the present technology.

Adoptive cell therapy (ACT) involves expanding immune cells ex vivo and then reinfusing them to treat diseases such as cancer. T cells that recognize tumor antigens can be expanded selectively, or T cells can be transduced with chimeric antigen receptors (CARs) that target tumor antigens. CAR therapy, in particular, has yielded remarkable results against certain B cell leukemias. It has been very challenging, however, to apply ACT to other malignancies, particularly solid tumors (N. N. Shah, T. J. Fry, *Nat Rev Clin Oncol* 16, 372-385 (2019)). At least some of this difficulty arises from cell-intrinsic regulatory programs that limit the scope of T cell function. The ability to mount potent cytotoxic and inflammatory responses is largely restricted to short-lived effector T cells, which can neither survive nor self renew over prolonged periods (N. Zhang, M. J. Bevan, *Immunity* 35, 161-168 (2011)). In addition, T cells become functionally exhausted after sustained antigen exposure, placing strict constraints on their activity (L. M. McLane et al., *Annu Rev Immunol*, (2019)). While this behavior is entirely appropriate under homeostatic conditions or when the immune system is battling transient infections, it is counterproductive in the context of cellular immunotherapy, where T cells must mount vigorous responses against established tumors for extended periods of time.

Accordingly, there is an urgent need for methods and compositions that improve in vivo survival and functional sustainability of T cells.

SUMMARY OF THE PRESENT TECHNOLOGY

In one aspect, the present disclosure provides an engineered immune cell comprising a non-endogenous expression vector that includes a mammalian miR200c nucleic acid sequence. In some embodiments, the mammalian miR200c nucleic acid sequence comprises SEQ ID NO: 25 or SEQ ID NO: 26. Additionally or alternatively, in some embodiments, the engineered immune cell comprises a non-endogenous expression vector that includes a mammalian EpCAM nucleic acid sequence. In certain embodiments, the mammalian EpCAM nucleic acid sequence comprises SEQ ID NO: 27 or SEQ ID NO: 28, or comprises an EpCAM nucleic acid encoding the polypeptide of SEQ ID NO: 29 or SEQ ID NO: 30. In some embodiments, the non-endogenous expression vector including the miR200c nucleic acid sequence and the non-endogenous expression vector including the EpCAM nucleic acid sequence are the same. In other embodiments, the non-endogenous expression vector including the miR200c nucleic acid sequence and the non-endogenous expression vector including the EpCAM nucleic acid sequence are distinct.

In another aspect, the present disclosure provides an engineered immune cell comprising a non-endogenous expression vector that includes a mammalian EpCAM nucleic acid sequence. In certain embodiments, the mammalian EpCAM nucleic acid sequence comprises the EpCAM nucleic acid sequence of SEQ ID NO: 27 or SEQ ID NO: 28, or an EpCAM nucleic acid encoding the polypeptide of SEQ ID NO: 29 or SEQ ID NO: 30.

In any and all embodiments of the engineered immune cell disclosed herein, the non-endogenous expression vector including the miR200c nucleic acid sequence and/or the non-endogenous expression vector including the EpCAM nucleic acid sequence is a plasmid, a cosmid, a bacmid, a bacterial artificial chromosome (BAC), a yeast artificial chromosome (YAC), or a viral vector. In certain embodiments, the viral vector is a retroviral vector. In any and all embodiments of the engineered immune cell disclosed herein, the non-endogenous expression vector is episomal or is integrated into the genome of the engineered immune cell.

Additionally or alternatively, in some embodiments of the engineered immune cell disclosed herein, the miR200c nucleic acid sequence and/or the EpCAM nucleic acid sequence is operably linked to an expression control sequence. The expression control sequence may be an inducible promoter or a constitutive promoter. In certain embodiments, the expression control sequence is a native EpCAM promoter, a native miR200c promoter, or a heterologous promoter. Additionally or alternatively, in some embodiments of the engineered immune cell disclosed herein, the non-endogenous vector including the miR200c nucleic acid sequence or the EpCAM nucleic acid sequence further comprises at least one of a bioluminescent protein, a fluorescent protein, a chemiluminescent protein, an epitope tag, or a selectable marker.

Additionally or alternatively, in some embodiments, the engineered immune cell is a lymphocyte or a myeloid cell. The lymphocyte may be a T cell, a B cell, a tumor infiltrating lymphocyte, or a natural killer cell. In some embodiments, the T cell is a CD8$^+$ cytotoxic T cell or a CD4$^+$ T cell. In any and all embodiments of the engineered immune cell disclosed herein, the T cell comprises a native T cell receptor (TCR), a non-native TCR, or a chimeric antigen receptor (CAR). In any of the preceding embodiments of the engineered immune cell disclosed herein, the engineered immune cells are derived from an autologous donor or an allogenic donor.

In one aspect, the present disclosure provides a composition comprising an effective amount of any and all embodiments of the engineered immune cell disclosed herein and a pharmaceutically acceptable carrier.

In another aspect, the present disclosure provides a method of preparing immune cells for adoptive cell therapy comprising: isolating immune cells from a donor subject; and transducing the immune cells with a non-endogenous expression vector that includes a mammalian miR200c encoding nucleic acid sequence (e.g., the miR200c encoding nucleic acid sequence of SEQ ID NO: 25 or SEQ ID NO: 26), and/or a mammalian EpCAM encoding nucleic acid sequence (e.g., the EpCAM nucleic acid sequence of SEQ ID NO: 27 or SEQ ID NO: 28 or an EpCAM nucleic acid encoding the polypeptide of SEQ ID NO: 29 or SEQ ID NO: 30).

In yet another aspect, the present disclosure provides a method of preparing immune cells for adoptive cell therapy comprising: isolating immune cells from a donor subject; transducing the immune cells with a non-endogenous expression vector that includes a mammalian miR200c encoding nucleic acid sequence (e.g., the miR200c encoding nucleic acid sequence of SEQ ID NO: 25 or SEQ ID NO: 26), and/or a mammalian EpCAM encoding nucleic acid sequence (e.g., the EpCAM nucleic acid sequence of SEQ ID NO: 27 or SEQ ID NO: 28 or an EpCAM nucleic acid encoding the polypeptide of SEQ ID NO: 29 or SEQ ID NO: 30); and administering the transduced cells to a recipient subject. In some embodiments, the donor subject and the recipient subject are the same. In other embodiments, the donor subject and the recipient subject are different.

Additionally or alternatively, in some embodiments of the methods disclosed herein, the immune cells isolated from the donor subject comprise one or more lymphocytes. The one or more lymphocytes may be a T cell, a B cell, a tumor infiltrating lymphocyte, or a natural killer cell. In some embodiments, the T cell is a $CD8^+$ cytotoxic T cell or a $CD4^+$ T cell. In any and all embodiments of the methods disclosed herein, the T cell comprises a native T cell receptor (TCR), a non-native TCR, or a chimeric antigen receptor (CAR). In certain embodiments, the chimeric antigen receptor (CAR) binds to a tumor antigen. Additionally or alternatively, in some embodiments, the CAR binds to a tumor antigen selected from the group consisting of carbonic anhydrase 9 (CAIX), CD19, prominin-1 (CD133), CD38 antigen (CD38), CD3, GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, LMP2, p53, lung resistance protein (LRP), Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, P1GF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y ($Le^y$) antigen, E-cadherin, V-cadherin, GPC3, EpCAM, CD4, CD8, CD21, CD23, CD46, CD80, HLA-DR, CD74, CD22, CD14, CD15, CD16, CD123, TCR gamma/delta, NKp46, KIR, CD56, DLL3, PD-1, PD-L1, CD28, CD137, CD99, GloboH, CD24, STEAP1, B7H3, Polysialic Acid, OX40, OX40-ligand, and peptide MHC complexes (with peptides derived from TP53, KRAS, MYC, EBNA1-6, PRAME, MART, tyronsinase, MAGEA1-A6, pme117, LMP2, or WT1).

In one aspect, the present disclosure provides a method for treating cancer or inhibiting tumor growth or metastasis in a subject in need thereof comprising administering to the subject an effective amount of any and all embodiments of the engineered immune cell disclosed herein. Examples of cancers or tumors include, but are not limited to, adrenal cancers, bladder cancers, blood cancers, bone cancers, brain cancers, breast cancers, carcinoma, cervical cancers, colon cancers, colorectal cancers, corpus uterine cancers, ear, nose and throat (ENT) cancers, endometrial cancers, esophageal cancers, gastrointestinal cancers, head and neck cancers, Hodgkin's disease, intestinal cancers, kidney cancers, larynx cancers, acute and chronic leukemias, liver cancers, lymph node cancers, lymphomas, lung cancers, melanomas, mesothelioma, myelomas, nasopharynx cancers, neuroblastomas, non-Hodgkin's lymphoma, oral cancers, ovarian cancers, pancreatic cancers, penile cancers, pharynx cancers, prostate cancers, rectal cancers, sarcoma, seminomas, skin cancers, stomach cancers, teratomas, testicular cancers, thyroid cancers, uterine cancers, vaginal cancers, vascular tumors, and metastases thereof. In some embodiments of the methods disclosed herein, the engineered immune cell is administered pleurally, intravenously, subcutaneously, intranodally, intratumorally, intrathecally, intrapleurally or intraperitoneally.

Additionally or alternatively, in some embodiments, the methods of the present technology further comprise administering an additional therapy selected from among chemotherapeutic agents, immune checkpoint inhibitors, monoclonal antibodies that specifically target tumor antigens, immune activating agents (e.g., interferons, interleukins, cytokines), oncolytic virus therapy and cancer vaccines.

BRIEF DESCRIPTION OF THE DRAWINGS

FIG. 1A shows a schematic diagram demonstrating the design of the miR trogocytosis screen. For FIG. 1B, miRs conferring high (blue) or low (red) trogocytosis in the trogocytosis screen were transduced, along with miRScr, into OT1 CTLs. The cytotoxicity of the resulting CTLs was then evaluated using OVA-loaded EL4 cells as targets. Data points denote the killing index, defined as the fraction of target cells lysed by CTLs expressing a miR of interest divided by the fraction of target cells lysed by CTLs expressing miRScr. miR200c and miR16 are highlighted. For FIGS. 1C-1D and FIGS. 1F-1G, OT1 CTLs expressing the indicated miRs were incubated with EL4 target cells loaded with the indicated concentrations of OVA. FIG. 1C shows trogocytosis quantified by flow cytometry after 2 hours. FIG. 1D shows specific lysis of target cells assessed after 4 hours. FIG. 1F shows CTL-target cell conjugate formation assessed by flow cytometry after 20 min. FIG. 1G shows CTL degranulation assessed by surface exposure of Lamp1 after 2 hours. For FIG. 1E, OT1 CTLs expressing the indicated miRs were incubated with B16OVA target cells at various effector:target (E:T) ratios, and target cell lysis was assessed after 4 hours. All error bars denote standard error of the mean (SEM), determined from technical triplicates. *, , *, and **** indicate P≤0.05, P≤0.01, P≤0.001, and P≤0.0001, respectively, calculated by Student's t test. Significance calculations compared miR200c (red asterisks) or miR16 (blue asterisks) CTLs with miRScr CTLs. All data are representative of at least 2 independent experiments.

In FIGS. 2A-2C, significance calculations compared the miR200c and miRScr groups, whereas in FIG. 2D, significance calculation compared the miR200c+αPD1 and miR200c groups (maroon asterisks) or the miRScr+ αPD1 and miRScr groups (aqua asterisks). All data are representative of at least 2 independent experiments. See also FIGS. 9A-9D.

FIG. 3C shows that Bcl2 levels in miR200c and miRScr CTLs, assessed by immunoblot, with actin as a loading control. For FIG. 3D, CTLs expressing miR200c or miRScr were transferred into medium lacking IL2 and survival were assessed 48 hours later by DAPI incorporation. n=3 for each group.

FIG. 4A shows a schematic diagram of experimental approach. FIG. 4B shows a representative flow cytometry plot demonstrating TNF and IFNγ expression in the indicated tumor infiltrating CTLs, extracted one week after infusion and restimulated with PMA/ionomycin. FIG. 4C shows quantification of TNF⁺

(left), IFNγ⁺ (center), and TNF⁺FNγ⁺ (right) tumor infiltrating CTLs from unstimulated (un) and PMA/ionomycin stimulated (stim) samples. n=3 mice per group. FIG. 4D shows a representative flow cytometry plot demonstrating TCF1 and T-bet expression in tumor infiltrating CTLs, extracted one week after infusion into tumor bearing mice. FIG. 4E shows quantification of TCF1 and T-bet expression in tumor infiltrating CTLs. n=3 mice per group. FIGS. 4F-4G show flow cytometric analysis of exhaustion markers in miRScr or miR200c OT1 CTLs, extracted 2 weeks after infusion into B16OVA tumor bearing mice. FIG. 4F shows a representative overlay plot demonstrating PD1 and LAG3 expression in tumor infiltrating CTLs. FIG. 4G shows quantification of PD1 (left), LAG3 (middle), and TIM3 (right) expression in CTLs extracted from the tumor and spleen (sp). n≥6 per group for PD1 and LAG3, n=4 per group for TIM3. FIG. 4H shows β-catenin (βcat) levels in CTLs expressing the indicated miRs, assessed by immunoblot using actin as a loading control. All error bars denote SEM. ns, *, and ** indicate not significant, P≤0.05, and P≤0.01, respectively, calculated by Student's t test. Data in G were pooled from two independent experiments. All other data are representative of at least 2 independent experiments. See also FIGS. 11A-11J.

FIGS. 5A-5G show that miR200c promotes epithelial gene expression and anti-tumor function by suppressing Zeb 1. FIG. 5A shows GSEA of RNA-seq data demonstrating correspondence between miR200c-induced genes and genes downregulated during EMT (D. P. Hollern, et al., PLoS Genet 14: e1007135 (2018); E. Charafe-Jauffret et al., Oncogene 25: 2273-2284 (2006)), genes downregulated during metastasis (J. Jaeger, et al., Clin Cancer Res 13: 806-815 (2007)) (right), and genes repressed by Zeb1 (K. Aigner, et al., Oncogene 26: 6979-6988 (2007)). NES=Normalized Enrichment Score. FIG. 5B shows a representative histogram demonstrating upregulation of EpCAM in miR200c CTLs. Isotype control staining is shown in gray. FIG. 5C shows (Left) an immunoblot demonstrating downregulation of Zeb1 in miR200c CTLs, and (Right) an immunoblot demonstrating Zeb1 depletion by gRNAs 1, 4, and 6 in OT1 Cas9 CTLs. Actin served as a loading control. FIG. 5D shows upregulation of EpCAM in CTLs expressing Zeb1 gRNAs. For FIG. 5E, Zeb1-CR and control (NT-CR) CTLs were transferred into medium lacking IL2 and survival assessed 48 hours later by DAPI incorporation. n=3 for each group. For FIG. 5F, a 1:1 mixture of Zeb1-CR1 and NT-CR CTLs was transferred into B16OVA tumor bearing mice. After 7 days, CTLs were extracted from various organs and quantified by flow cytometry. n=4 for each group. For FIG. 5G, mice bearing s.c. B16OVA tumors were treated with OT1 Cas9 CTLs expressing the indicated miRs and gRNAs. Left, tumor size graphed against time. Right, Kaplan-Meier plot showing overall survival. PBS denotes vehicle control. n=5 for each group. All error bars indicate SEM. *,  *, and **** indicate P≤0.05, P≤0.01, P≤0.001, and P≤0.0001, respectively, calculated by Student's t test (FIG. 5E), 2way ANOVA (FIG. 5F and the left graph in FIG. 5G), and Log-rank test for the right graph in FIG. 5G. In FIG. 5G, significance calculations compared miR200c-NT-CR with miRScr-NT-CR (red asterisks) and miRScr-Zeb 1-CR1 with miRScr-NT-CR (purple asterisks). All data are representative of at least 2 independent experiments. See also FIGS. 12A-12B, FIGS. 13A-13C, and FIGS. 14A-14D.

FIG. 6A shows EpCAM expression on OT1 Cas9 CTLs transduced with retroviruses expressing the indicated miRs and gRNAs. NT refers to nontargeting control gRNA. for FIG. 6B, mice bearing s.c. B16OVA tumors were treated with OT1 Cas9 CTLs expressing the indicated miRs and gRNAs. PBS denotes vehicle control. Left, tumor size graphed against time. Right, Kaplan-Meier plot showing overall survival. n=10 for each group. For FIG. 6C, a 1:1 mixture of OT1-Cas9 CTLs expressing the indicated miRs and gRNAs was transferred into B16-OVA tumor bearing mice. After 7 days, CTLs were extracted from various organs and analyzed by flow cytometry. n=4 for each group. All error bars indicate SEM. * , , *, and ** indicate P≤0.05, P≤0.01, P≤0.001, and P≤0.0001, respectively, calculated by 2way ANOVA (FIG. 6B, left graph, and FIG. 6C) or Log-rank test (FIG. 6B, right graph). In FIG. 6B**, significance calculations compared miR200c-NT-CR with miRScr-NT-CR (red asterisks) and miR200c-NT-CR with miR200c-EpCAM-CR (pink asterisks). All data are representative of at least 2 independent experiments.

FIG. 7A shows EpCAM expression in OT1 CTLs transduced with EpCAM or control (Ctrl) retrovirus. For FIG. 7B show, a 1:1 mixture of EpCAM and Ctrl CTLs was transferred into B16OVA tumor bearing mice. After 7 days, CTLs were extracted from various organs and quantified by flow cytometry. n≥3 for each group. FIGS. 7C-7E show that mice bearing s.c. B16OVA (FIG. 7C), B16 (FIG. 7D), or EL4 (FIG. 7E) tumors were injected with OT1 (FIG. 7C) or Pmel 1 (FIG. 7D) CTLs expressing EpCAM or empty vector (Ctrl) or OT1 CTLs expressing EpCAM or empty vector (Ctrl) together with GD2CAR (FIG. 7E). An additional group received vehicle control (PBS). Above, mean tumor volume is plotted against time. Below, Kaplan-Meier plots showing overall survival. n=10 for FIG. 7C, n=10 for FIG. 7D, n≥8 for FIG. 7E. For FIGS. 7F-7H, a 1:1 mixture of EpCAM and Ctrl CTLs was transferred into B16OVA tumor bearing mice. After 1 week, tumor infiltrating CTLs were stained for TCF1 (FIG. 7F) and T-bet (FIG. 7G), or restimulated and stained for TNF (FIG. 7H). n=3 mice per group. All error bars indicate SEM. ns, * , , *, and ** indicate not significant, P≤0.05, P≤0.01, P≤0.001, and P≤0.0001, respectively, calculated by Student's t test (FIGS. 7F-7H), 2way ANOVA (FIG. 7B and top graphs in FIGS. 7C-7E), or Log-rank test (bottom graphs in FIGS. 7C-7E). FIGS. 7C-7E, significance calculations compared the EpCAM and Ctrl groups. Data are representative of at least 2 independent experiments. See also FIGS. 15A-15F**.

FIG. 8A shows a schematic diagram of the NALM6 model. FIG. 8B shows a representative BLI images of mice 2 weeks after the indicated treatment. FIG. 8C shows tumor growth in mice receiving untransduced T cells (left) and in mice receiving Ctrl (center) or EpCAM (right) transduced CAR T cells. n=7 mice per group. FIG. 8D shows survival curves from the same experiment. p-value calculated by Log-rank test. FIG. 8E shows quantification of PD1 (left), LAG3 (middle), and TIM3 (right) expression in T cells extracted from the bone marrow (bm) and spleen (sp) 17 d after infusion into NALM6 tumor bearing mice. n=5 per group. ns denotes not significant, calculated by Student's t test. For FIG. 8F, NSG mice bearing NALM6 tumors were injected with a 1:1 mixture of CD19 CAR T cells transduced with EpCAM or CD271(Ctrl). After 7 days, CTLs were extracted from various organs and quantified by flow cytometry. n≥3 for each group. * , , and *, indicate P≤0.05, P≤0.01, and P≤0.001, respectively, calculated by 2way ANOVA. All data are representative of at least 2 independent experiments. See also FIGS. 16A-16C.

FIG. 9A shows a schematic diagram of sponge-based inhibition of miR200c. For FIG. 9B, sponge constructs containing between 2 (sp2) and 6 (sp6) repeats of miR200c complement were inserted into a combined Firefly/Renilla luciferase expression vector downstream of the Firefly luciferase gene. Firefly/Renilla luminescence ratio was recorded after transfection into 293T cells stably expressing miR200c. n=3 per group. FIG. 9C shows that OT1 CTLs expressing the indicated miRs and either a miR200c sponge (200sp) or a nontargeting sponge control (Scrsp) were incubated with EL4 target cells loaded with the indicated concentrations of OVA. Specific lysis was assessed after 4 hours. Data points were derived from technical triplicates. For FIG. 9D, mice bearing s.c. B16OVA tumors were treated with OT1 CTLs expressing the indicated miRs and sponge constructs. PBS denotes vehicle control. Left, mean tumor volume graphed against time. Right, Kaplan-Meier plot showing overall survival. n=10 for each group. All error bars indicate SEM. ns, , *, and ** indicate not significant, P≤0.01, P≤0.001, and P≤0.0001, respectively, calculated by Student's t test (FIG. 9C), 1 way ANOVA (FIG. 9B), 2way ANOVA (FIG. 9D, left graph), and Log-rank test (FIG. 9D, right graph). In FIG. 9D**, significance calculations compared the miR200c-Scrsp and miRScr-Scrsp groups. All data are representative of at least 2 independent experiments.

FIG. 10B shows (Above) representative images of B16OVA tumors demonstrating infiltrating miR200c or miRScr OT1 CTLs (identified by CD45.2 expression in a CD45.1$^{+/+}$ host). Scale bars=100 μm. Below, quantification of miR200c or miRScr OT1 CTL density. n≥239 sections from 49 mice. Data pooled from 13 independent experiments. Error bars denote SEM. *, , and * indicate P≤0.05, P≤0.01, and P≤0.01, respectively, calculated by 2way ANOVA (FIGS. 10A-10B) or unpaired Student's t test (FIG. 10C).

FIG. 11B shows Ki67 expression in OT1 CTLs transduced with the indicated miRs. Isotype control staining is shown in gray. FIG. 11C shows Ki67 expression in miRScr and miR200c tumor infiltrating OT1 CTLs, 1 week after transfer into B16OVA tumor bearing mice. n=6 mice per group. For FIGS. 11D-11E, miRScr or miR200c OT1 CTLs were stimulated with anti-CD3ε/CD28 and stained for TNF (FIG. 11D) and IFNγ (FIG. 11E) after 4 hours. FIG. 11F shows flow cytometric analysis of Eomes (left) and Blimp1 (right) expression in miRScr or miR200c OT1 CTLs, extracted from B16OVA tumors 1 week after infusion into tumor bearing mice. n=3 mice per group. FIG. 11G shows a representative flow plot of TCF1 and T-bet expression in miRScr and miR200c CTLs prior to infusion. FIG. 11H shows quantification of PD1 expression in CTLs extracted from the tumor 1 week after infusion into B16OVA tumor bearing mice. n=8 per sample. FIG. 11I shows flow plots demonstrating CD44 and CD62L expression in CTLs expressing the indicated miRs. FIG. 11J shows E-Cadherin expression in OT1 CTLs transduced with miRScr or miR200c. Isotype control staining is shown in gray. All error bars denote SEM. ns indicates not significant, determined by Student's t test. Data in H were pooled from 2 independent experiments. All other data are representative of at least 2 independent experiments.

FIG. 12A shows a volcano plot demonstrating genes differentially expressed in miR200c CTLs relative to miRScr controls. Statistically significant differential expression is denoted in cyan. Selected upregulated genes are labeled by geneid. FIG. 12B shows GSEA comparing miR200c-induced genes and genes associated with naïve, memory, effector, and exhausted T cells (E. J. Wherry, et al., *Immunity* 27: 670-684 (2007)). NES=Normalized Enrichment Score.

Figure 13C:
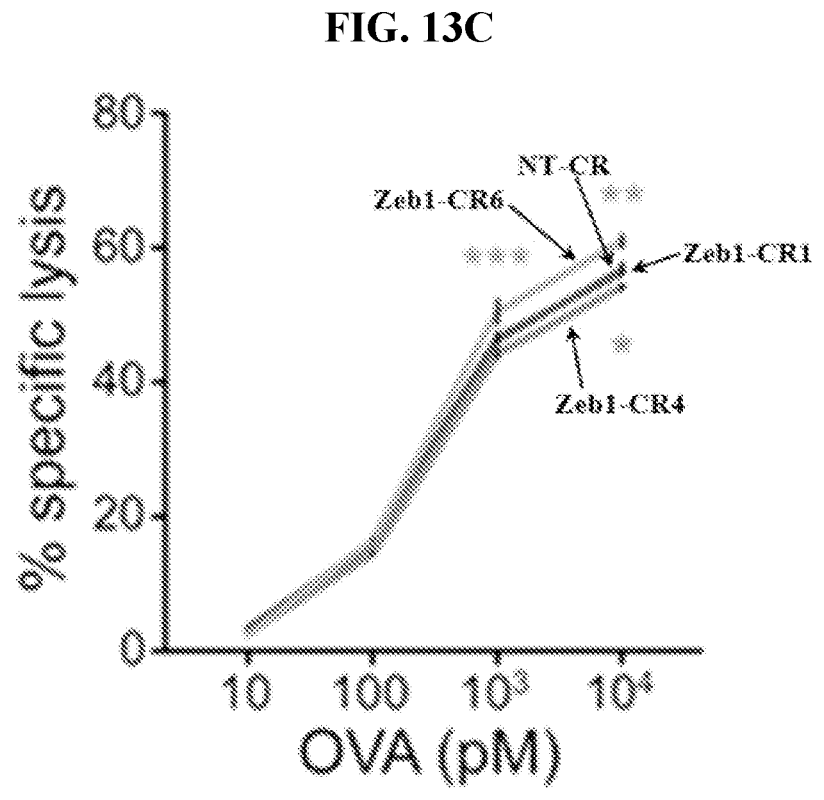

FIGS. 13A-13C show that Zeb 1 deletion phenocopies miR200c expression. Related to FIGS. 5A-5G. FIG. 13A shows E-Cadherin expression in OT1 Cas9 CTLs transduced with the indicated gRNAs. FIG. 13B shows OT1 Cas9 CTLs expressing the indicated gRNAs were stained with CTV and then stimulated with OVA-loaded splenocytes. CTV dilution was evaluated after 5 days. Shaded curves denote time 0. For FIG. 13C, OT1 Cas9 CTLs expressing the indicated gRNAs were incubated with EL4 target cells loaded with increasing concentrations of OVA. Specific lysis was assessed after 4 hours. Error bars denote SEM, determined from technical triplicates. *, , and * indicate P≤0.05, P≤0.01, and P≤0.001, respectively, calculated by Student's t test. All data are representative of at least 2 independent experiments.

FIG. 14A shows AhR levels in OT1 CTLs expressing the indicated miRs (left), in OT1 Cas9 CTLs expressing the indicated gRNAs (center), and in OT1 CTLs transduced with exogenous AhR and empty vector (Ctrl). For FIG. 14B, OT1 CTLs transduced with AhR or empty vector (Ctrl) were incubated with EL4 target cells loaded with increasing concentrations of OVA. Specific lysis was assessed after 4 hours. n=3, from technical triplicates. For FIG. 14C, mice bearing s.c. B16OVA tumors were injected with OT1 CTLs expressing AhR or empty vector (Ctrl). An additional group received vehicle control (PBS). Left, mean tumor volume graphed against time. Right, Kaplan-Meier plot showing overall survival. n=5 for each group. For FIG. 14D, mice bearing s.c. B16OVA tumors were injected with Ahr$^{+/-}$ or Ahr$^{-/-}$ OTI CTLs expressing the indicated miRs. An additional group received vehicle control (PBS). Left, mean tumor volume graphed against time. Right, Kaplan-Meier plot showing overall survival. n=5 for each group. All error bars indicate SEM. *, , *, and **** indicate P≤0.05, P≤0.01, P≤0.001, and P≤0.0001, respectively, calculated by unpaired Student's t test (FIG. 14B) or 2way ANOVA (FIGS. 14C-14D). In FIG. 14D, significance calculations compared Ahr$^{+/+}$200c with Ahr$^{+/-}$Scr (red asterisks) and Ahr$^{-/-}$ 200c with Ahr$^{+/-}$Scr (pink asterisks). All data are representative of at least 2 independent experiments.

7A-7H. FIG. 15A shows Bc12 levels (left) and β-catenin (βcat) levels (right) in CTLs expressing EpCAM or empty vector (Ctrl), assessed by immunoblot. Actin served as a loading control. For FIG. 15B, CTLs expressing EpCAM or empty vector (Ctrl) were transferred into medium lacking IL2 and survival assessed 24 hours later by DAPI incorporation. n=4 for each group. FIG. 15C shows CellEvent Caspase 3/7 staining of EpCAM and Ctrl CTLs cultured in RPMI with either 30 IU/ml IL2 (left) or 5 ng/ml IL7 (right). n=3 for each group. FIG. 15D shows CellEvent Caspase 3/7 staining of EpCAM and Ctrl CTLs treated with 2 μM staurosporine or 20 ng/ml FasL. n=3 for each group. For FIG. 15E, OT1 CTLs expressing EpCAM or empty vector (Ctrl) were incubated with target cells loaded with the indicated concentrations of OVA. Specific lysis was assessed after 4 h. Data points were derived from technical triplicates. FIG. 15F shows flow plot demonstrating CD44 and CD62L expression in CTLs expressing EpCAM or empty vector (Ctrl). All error bars denote SEM. , *, and **** indicate P≤0.01, P≤0.001, and P≤0.0001, respectively, calculated by unpaired Student's t test. All data are representative of at least 2 independent experiments.

FIG. 16A shows quantification of PD1 (left), LAG3 (middle), and TIM3 (right) expression in OT1 CTLs extracted from the tumor and spleen (sp) 2 weeks after infusion into B16OVA tumor bearing mice. n≥6 per group for PD1 and LAG3, n=4 per group for TIM3. Data were pooled from two independent experiments. For FIGS. 16A-16C, NSG mice bearing NALM6 tumors were injected with human CD19CAR T cells transduced with EpCAM or empty vector (Ctrl). Quantification of PD1 (left), LAG3 (middle), and TIM3 (right) expression in CD4$^+$ (B) and CD8$^+$ (C) T cells extracted from the bone marrow (bm) and spleen (sp) 17 days after infusion. All error bars denote SEM. ns denotes not significant, calculated by unpaired Student's t test.

DETAILED DESCRIPTION

Figure 1A:
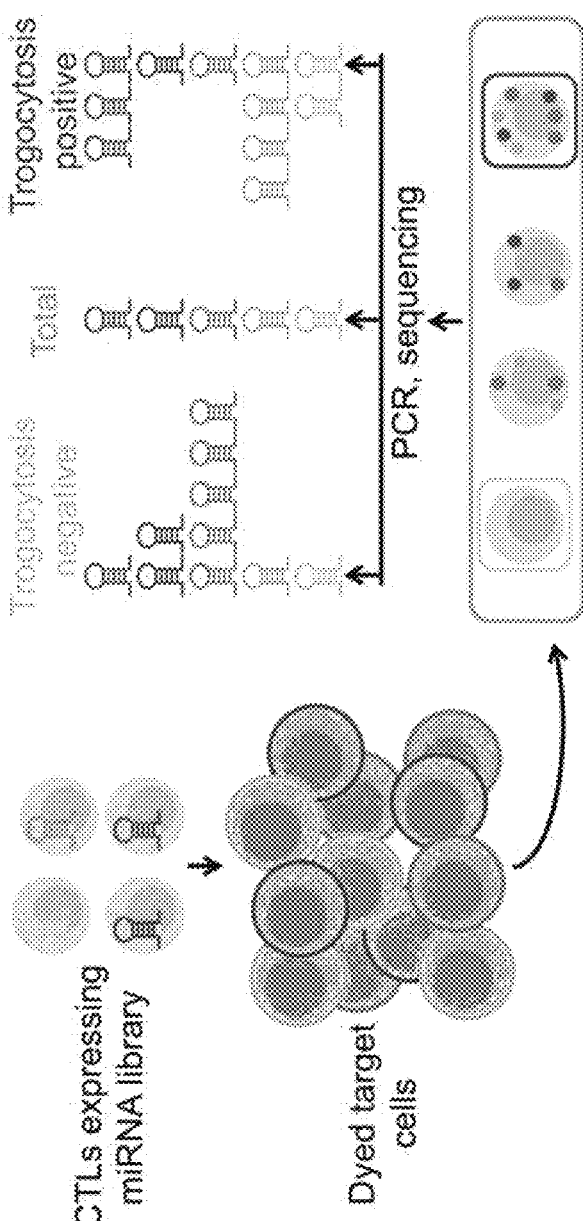
FIGS. 1A-1G show trogocytosis screen to identify miRs that alter in vitro cytotoxicity.

It is to be appreciated that certain aspects, modes, embodiments, variations and features of the present methods are described below in various levels of detail in order to provide a substantial understanding of the present technology.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) PCR 1: *A Practical Approach* (IRL Press at Oxford University Press); MacPherson et al. (1995) PCR 2: *A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.*

The present disclosure demonstrates that ectopic expression of microRNA-200c (miR200c) or EpCAM in immune cells markedly reduces apoptosis during engraftment, thereby enhancing their in vivo persistence compared to native immune cells. As demonstrated in the Examples herein, CD8$^+$ cytotoxic T lymphocytes (CTLs) transduced with miR200c or EpCAM exhibited an increase in CTL survival, proliferation, and TNF production in vitro compared to native CTLs, without impairing their cytotoxicity. Moreover, CTLs overexpressing miR200c or EpCAM significantly augmented anti-tumor function in preclinical ACT models of both solid and liquid malignancies. Accordingly, the engineered immune cells of the present technology are useful in methods for improved ACT to treat various diseases.

Definitions

Unless defined otherwise, all technical and scientific terms used herein have the meaning commonly understood by a person skilled in the art to which this disclosure belongs. The following references provide one of skill with a general definition of many of the terms used in the present disclosure. Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

As used herein, the singular forms "a", "an" and "the" are intended to include the plural forms as well, unless the context clearly indicates otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value.

As used herein, the term "administration" of an agent to a subject includes any route of introducing or delivering the agent to a subject to perform its intended function. Administration can be carried out by any suitable route, including, but not limited to, intravenously, intramuscularly, intraperitoneally, subcutaneously, and other suitable routes as described herein. Administration includes self-administration and the administration by another.

As used herein "adoptive cell therapeutic composition" refers to any composition comprising cells suitable for adoptive cell transfer. In exemplary embodiments, the adoptive cell therapeutic composition comprises a cell type selected from a group consisting of a tumor infiltrating lymphocyte (TIL), TCR (i.e. heterologous T-cell receptor) modified lymphocytes (e.g., eTCR T cells and caTCR T cells) and CAR (i.e. chimeric antigen receptor) modified lymphocytes (e.g., CAR T cells). In another embodiment, the adoptive cell therapeutic composition comprises a cell type selected from a group consisting of T-cells, CD8+ cells, CD4+ cells, NK-cells, delta-gamma T-cells, regulatory T-cells and peripheral blood mononuclear cells. In another embodiment, TILs, T-cells, CD8+ cells, CD4+ cells, NK-cells, delta-gamma T-cells, regulatory T-cells or peripheral blood mononuclear cells form the adoptive cell therapeutic composition. In one embodiment, the adoptive cell therapeutic composition comprises T cells.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to agents that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. In some embodiments, amino acids forming a polypeptide are in the D form. In some embodiments, the amino acids forming a polypeptide are in the L form. In some embodiments, a first plurality of amino acids forming a polypeptide is in the D form and a second plurality is in the L form.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter code.

As used herein, the term "analog" refers to a structurally related polypeptide or nucleic acid molecule having the function of a reference polypeptide or nucleic acid molecule.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 1000 cells, at least about 10,000 cells, at least about 100,000 cells, at least about $1 \times 10^6$ cells, at least about $1 \times 10^7$ cells, at least about $1 \times 10^8$ cells, at least about $1 \times 10^9$ cells, at least about $1 \times 10^{10}$ cells, at least about $1 \times 10^{11}$ cells, at least about $1 \times 10^{12}$ cells, or more cells expressing similar or different phenotypes.

As used herein, "chimeric antigen receptor" or "CAR", is a synthetic receptor which grafts or confers a specificity of interest onto an immune effector cell. There are currently three generations of CARs. "First generation" CARs are typically composed of an extracellular antigen binding domain (e.g., a single-chain variable fragment (scFv)), a transmembrane domain, and cytoplasmic/intracellular domain of the T cell receptor (TCR) chain. "First generation" CARs typically have the intracellular domain from the CD3 chain, which is the primary transmitter of signals from endogenous TCRs. "First generation" CARs can provide de novo antigen recognition and cause activation of both CD4$^+$ and CD8$^+$ T cells through their CD3ζ chain signaling domain in a single fusion molecule, independent of HLA-mediated antigen presentation. In some embodiments, the engineered immune cells provided herein express a "first generation" CAR. "Second generation" CARs add intracellular domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-1BB) and activation (e.g., CD3ζ). In some embodiments, the engineered immune cells provided herein express a "second generation" CAR. "Third generation" CARs comprise those that provide multiple co-stimulation (e.g., CD28 and 4-1BB) and activation (e.g., CD3ζ). In some embodiments, the engineered immune cells provided herein express a "third generation" CAR.

As used herein, the term "chimeric co-stimulatory receptor" or "CCR" refers to a chimeric receptor that binds to an antigen and provides co-stimulatory signals, but does not provide a T-cell activation signal.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

As used herein, the term, "co-stimulatory signaling domain," or "co-stimulatory domain", refers to the portion of the engineered receptor comprising the intracellular domain of a co-stimulatory molecule. Co-stimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1BB (CD137), OX40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from CD28 and 4-1BB, other costimulatory domains are contemplated for use with the engineered receptors described herein. The inclusion of one or more co-stimulatory signaling domains can enhance the efficacy and expansion of T cells expressing engineered receptors. The intracellular signaling and co-stimulatory signaling domains can be linked in any order in tandem to the carboxyl terminus of the transmembrane domain.

As used herein, the term "effective amount" or "therapeutically effective amount" refers to a quantity of an agent sufficient to achieve a desired therapeutic effect. In the context of therapeutic applications, the amount of a therapeutic agent administered to the subject can depend on the type and severity of the infection and on the characteristics of the individual, such as general health, age, sex, body weight and tolerance to drugs. It can also depend on the degree, severity and type of disease. The skilled artisan will be able to determine appropriate dosages depending on these and other factors.

As used herein, the term "engineered immune cell" refers to an immune cell that is genetically modified.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell. The expression level of a gene can be determined by measuring the amount of mRNA or protein in a cell or tissue sample. In one aspect, the expression level of a gene from one sample can be directly compared to the expression level of that gene from a control or reference sample. In another aspect, the expression level of a gene from one sample can be directly compared to the expression level of that gene from the same sample following administration of the compositions disclosed herein. The term "expression" also refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5) presentation of a polypeptide or protein on the cell surface; and (6) secretion or presentation or release of a polypeptide or protein from a cell.

As used herein, an "expression vector" includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, the term "heterologous nucleic acid molecule or polypeptide" refers to a nucleic acid molecule (e.g., a cDNA, DNA or RNA molecule) or polypeptide that is either not normally expressed or is expressed at an aberrant level in a cell or sample obtained from a cell. This nucleic acid can be from another organism, or it can be, for example, an mRNA molecule that is not normally expressed in a cell or sample.

As used herein, the term "increase" or "enhance" means to alter positively by at least about 5%, including, but not limited to, alter positively by about 5%, by about 10%, by about 25%, by about 30%, by about 50%, by about 75%, or by about 100%.

As used herein, the term "immune cell" refers to any cell that plays a role in the immune response of a subject. Immune cells are of hematopoietic origin, and include lymphocytes, such as B cells and T cells; natural killer cells; myeloid cells, such as monocytes, macrophages, dendritic cells, eosinophils, neutrophils, mast cells, basophils, and granulocytes.

As used herein, the term "native immune cell" refers to an immune cell that naturally occurs in the immune system.

As used herein, "operably linked" with reference to nucleic acid sequences, regions, elements or domains means that the nucleic acid regions are functionally related to each other. For example, nucleic acid encoding a leader peptide can be operably linked to nucleic acid encoding a polypeptide, whereby the nucleic acids can be transcribed and translated to express a functional fusion protein, wherein the leader peptide effects secretion of the fusion polypeptide. In some instances, the nucleic acid encoding a first polypeptide (e.g., a leader peptide) is operably linked to nucleic acid encoding a second polypeptide and the nucleic acids are transcribed as a single mRNA transcript, but translation of the mRNA transcript can result in one of two polypeptides being expressed. For example, an amber stop codon can be located between the nucleic acid encoding the first polypeptide and the nucleic acid encoding the second polypeptide, such that, when introduced into a partial amber suppressor cell, the resulting single mRNA transcript can be translated to produce either a fusion protein containing the first and second polypeptides, or can be translated to produce only the first polypeptide. In another example, a promoter can be operably linked to nucleic acid encoding a polypeptide, whereby the promoter regulates or mediates the transcription of the nucleic acid.

As used herein, the term "ligand" refers to a molecule that binds to a receptor. In particular, the ligand binds a receptor on another cell, allowing for cell-to-cell recognition and/or interaction.

The term "lymphocyte" refers to all immature, mature, undifferentiated and differentiated white lymphocyte populations including tissue specific and specialized varieties. It encompasses, by way of non-limiting example, B cells, T cells, NKT cells, and NK cells. In some embodiments, lymphocytes include all B cell lineages including pre-B cells, progenitor B cells, early pro-B cells, late pro-B cells, large pre-B cells, small pre-B cells, immature B cells, mature B cells, plasma B cells, memory B cells, B-1 cells, B-2 cells and anergic AN1/T3 cell populations.

As used herein, "microRNA" or "miRNA" refers to a class of naturally occurring, small non-coding RNA molecules that are partially complementary to one or more messenger RNA (mRNA) molecules, and downregulate expression of target genes by binding to the 3'-untranslated regions (3'-UTR) of mRNAs encoded by the target genes. As used herein, the term "miRNA" refers to both single-stranded miRNA and pre-miRNA, which is a double-stranded RNA having a stem-loop structure. The sequence of the miRNA can correspond to the full length of the miRNA encoding gene, or a subsequence thereof. Typically, the miRNA is at least about 15-50 nucleotides in length.

The term "myeloid cell" refers to all immature, mature, undifferentiated, and differentiated white blood cell populations that are derived from myeloid progenitors including tissue specific and specialized varieties, and encompasses, by way of non-limiting example, granulocytes (i.e., mast cells, neutrophils, eosinophils and basophils), monocytes, macrophages, and dendritic cells.

As used herein, the term "neoplasia" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasia can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells).

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, the term "reduce" means to alter negatively by at least about 5%, including, but not limited to, alter negatively by about 5%, by about 10%, by about 25%, by about 30%, by about 50%, by about 75%, or by about 100%.

As used herein, "expression control sequence" or "regulatory region" of a nucleic acid molecule means a cis-acting nucleotide sequence that influences expression, positively or negatively, of an operatively linked gene. Regulatory regions include sequences of nucleotides that confer inducible (i.e., require a substance or stimulus for increased transcription) expression of a gene. When an inducer is present or at increased concentration, gene expression can be increased. Regulatory regions also include sequences that confer repression of gene expression (i.e., a substance or stimulus decreases transcription). When a repressor is present or at increased concentration gene expression can be decreased. Regulatory regions are known to influence, modulate or control many in vivo biological activities including cell proliferation, cell growth and death, cell differentiation and immune modulation. Regulatory regions typically bind to one or more trans-acting proteins, which results in either increased or decreased transcription of the gene.

Particular examples of gene regulatory regions are promoters and enhancers. Promoters are sequences located around the transcription or translation start site, typically positioned 5' of the translation start site. Promoters usually are located within 1 Kb of the translation start site, but can be located further away, for example, 2 Kb, 3 Kb, 4 Kb, 5 Kb or more, up to and including 10 Kb. Enhancers are known to influence gene expression when positioned 5' or 3' of the gene, or when positioned in or a part of an exon or an intron. Enhancers also can function at a significant distance from the gene, for example, at a distance from about 3 Kb, 5 Kb, 7 Kb, 10 Kb, 15 Kb or more.

Regulatory regions also include, but are not limited to, in addition to promoter regions, sequences that facilitate translation, splicing signals for introns, maintenance of the correct reading frame of the gene to permit in-frame translation of mRNA and, stop codons, leader sequences and fusion partner sequences, internal ribosome binding site (IRES) elements for the creation of multigene, or polycistronic, messages, polyadenylation signals to provide proper polyadenylation of the transcript of a gene of interest and stop codons, and can be optionally included in an expression vector.

As used herein, the term "RNA" or "ribonucleic acid" defines a molecule comprising at least one ribonucleotide residue. Each ribonucleotide contains a ribose sugar, a phosphate group, and one of the four nitrogenous bases: adenine (A), cytosine (C), guanine (G), and uracil (U). Adjacent ribose nucleotide residues are chemically attached to one another in a chain via phosphodiester bonds. In cells, RNA is synthesized from DNA by RNA polymerase during transcription. The new RNA sequences are complementary to their DNA template, rather than being identical copies of the template. Some RNAs are then translated into proteins by ribosomes. Although some RNA molecules are not translated into proteins, many of the non-coding RNAs play crucial, active roles in the cell. For example, some RNA molecules (e.g. miRNAs and siRNAs) are involved in switching genes on and off, and other RNA molecules make up the protein synthesis machinery in ribosomes. The term RNA includes double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides.

As used herein, the terms "subject," "individual," or "patient" are used interchangeably and refer to an individual organism, a vertebrate, or a mammal and may include humans, non-human primates, rodents, and the like (e.g., which is to be the recipient of a particular treatment, or from whom cells are harvested). In certain embodiments, the individual, patient or subject is a human.

As used herein, "synthetic," with reference to, for example, a synthetic nucleic acid molecule or a synthetic gene or a synthetic peptide refers to a nucleic acid molecule or polypeptide molecule that is produced by recombinant methods and/or by chemical synthesis methods. As used herein, production by recombinant means by using recombinant DNA methods means the use of the well-known methods of molecular biology for expressing proteins encoded by cloned DNA.

As used herein, the term "T-cell" includes naïve T cells, CD4+ T cells, CD8+ T cells, memory T cells (including central memory T cells, stem-cell-like memory T cells (or stem-like memory T cells), and two types of effector memory T cells: e.g., $T_{EM}$ cells and TEMRA cells), activated T cells, anergic T cells, tolerant T cells, chimeric B cells, Regulatory T cells (also known as suppressor T cells), Natural killer T cells, Mucosal associated invariant T cells, and γδ T cells, and antigen-specific T cells.

As used herein, "T cell receptor" or "TCR", is a protein complex found on the surface of T cells, that is responsible for recognizing fragments of antigen as peptides bound to major histocompatibility complex molecules. TCR is composed of two disulfide-linked protein chains. Cells expressing a TCR containing the highly variable alpha (α) and beta (β) chains are referred to as αβ T cells. Cells expressing an alternate TCR, formed by variable gamma (γ) and delta (δ) chains, are referred to as γδ T cells. When the TCR engages with antigenic peptide and MHC (peptide/MHC), the T lymphocyte is activated through signal transduction, that is, a series of biochemical events mediated by associated enzymes, co-receptors, specialized adaptor molecules, and activated or released transcription factors. In some embodiments, the TCR is a native T cell receptor that is endogenous to the immune cells. In some embodiments, the TCR is an artificial receptor that mimics native TCR function, i.e., recognizing peptide antigens of key intracellular proteins in the context of MHC on the cell surface.

As used herein "tumor-infiltrating lymphocytes" or TILs refer to white blood cells that have left the bloodstream and migrated into a tumor.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. Therapeutic effects of treatment include, without limitation, inhibiting recurrence of disease, alleviation of symptoms, diminishment of any direct or indirect pathological consequences of the disease, preventing metastases, decreasing the rate of disease progression, amelioration or palliation of the disease state, and remission or improved prognosis. It is also to be appreciated that the various modes of treatment of diseases as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Adoptive Cell Therapy

The importance of sustained T cell activity for ACT has generated a great deal of interest in methods that increase the effective size of therapeutic T cell populations and prolong their functionality. Patients are typically subjected to conditioning chemotherapy or ablative radiation prior to infusion in order to reduce competition between transferred T cells and endogenous lymphocytes for homeostatic cytokines. Although these approaches significantly increase engraftment efficiency, a large fraction of infused T cells still perish within days (J. N. Blattman et al., *J Exp Med* 195, 657-664 (2002); C. Berger et al., *J Clin Invest* 118, 294-305 (2008)), and strategies for mitigating this death are poorly developed. Maintaining functional persistence after engraftment is also of critical importance. Provided herein are compositions comprising engineered immune cells that overexpress EpCAM and/or miR200c and uses thereof, that address these issues.

In addition, provided herein are compositions comprising heterologous nucleic acids encoding EpCAM and/or miR200c, vectors comprising heterologous nucleic acids encoding EpCAM and/or miR200c, or engineered immune cells expressing heterologous nucleic acids encoding EpCAM and/or miR200c and methods of using such compositions for the manufacture of an engineered immune cell. Without wishing to be bound by theory, ectopic expression of the epithelial cell markers miR200c and EpCAM prolonged the engraftment efficiency and persistence of T cells in tumor bearing subjects without compromising antigen-driven proliferation and cytokine secretion. Consequently, T cells overexpressing miR200c or EpCAM display enhanced anti-tumor activity in both T cell receptor (TCR) and CAR driven models of ACT.

In some embodiments, the engineered immune cells provided herein express a T-cell receptor (TCR) or other cell-surface ligand that binds to a target antigen, such as a tumor antigen or viral protein. In some embodiments, the T cell receptor is a wild-type or native T-cell receptor. In some embodiments, the TCR is an engineered receptor or a non-native receptor. In some embodiments, the engineered receptor is an engineered TCR (eTCR). In some embodiments, the engineered receptor is a chimeric antibody TCR (caTCR). In some embodiments, the engineered receptor is a chimeric antigen receptor (CAR).

In exemplary embodiments, the engineered immune cells provided herein express a native receptor, a non-native receptor, or an engineered receptor (e.g., a CAR, caTCR, or eTCR) or other cell-surface ligand that binds to a tumor antigen. In some embodiments, the engineered immune cells provided herein express a native receptor, a non-native receptor, or an engineered receptor (e.g., a CAR, caTCR, or eTCR) or other cell-surface ligand that binds to a tumor antigen presented in the context of an MHC molecule. In some embodiments, the engineered immune cells provided herein express a native receptor, a non-native receptor or an engineered receptor (e.g., a CAR, caTCR, or eTCR) or other cell-surface ligand that binds to a tumor antigen presented in the context of an HLA-A2 molecule. In exemplary embodiments, the engineered immune cells provided herein express a native receptor, a non-native receptor or an engineered receptor (e.g., a CAR, caTCR, or eTCR) or other cell-surface ligand that binds to a tumor antigen. Examples of tumor antigens bound by the native receptor, non-native receptor or engineered receptor (e.g., a CAR, caTCR, or eTCR) or other cell-surface ligand include, but is not limited to, carbonic anhydrase 9 (CAIX), CD19, prominin-1 (CD133), CD38 antigen (CD38), CD3, GPA33, HER2/neu, GD2, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, LMP2, p53, lung resistance protein (LRP), Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, P1GF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Le$^y$) antigen, E-cadherin, V-cadherin, GPC3, EpCAM, CD4, CD8, CD21, CD23, CD46, CD80, HLA-DR, CD74, CD22, CD14, CD15, CD16, CD123, TCR gamma/delta, NKp46, KIR, CD56, DLL3, PD-1, PD-L1, CD28, CD137, CD99, GloboH, CD24, STEAP1, B7H3, Polysialic Acid, OX40, OX40-ligand, and peptide MHC complexes (with peptides derived from TP53, KRAS, MYC, EBNA1-6, PRAME, MART, tyronsinase, MAGEA1-A6, pme117, LMP2, or WT1). Exemplary engineered receptors that bind to CD19 are described in International Publication No. WO2017070608, which is incorporated by reference in its entirety.

miRNA-200c

The miR-200 family has five members: miR-200a, miR-200b, miR200c, miR-141 and miR-429, which cooperatively maintain the epithelial phenotype through direct targeting of ZEB1 and ZEB2, two important transcription factors that repress E-cadherin and other polarity factor genes. Within the family, miR200c has been shown to be a marker for epithelial-mesenchymal transition (EMT), which is an important step of cancer metastasis (Iorio, M. V., et al., *Cancer Res* 67: 8699-8707 (2007); Hu, X., et al., *Gynecol. Oncol.* 114, 457-464; Diaz-Lopez, A., et al., *Cancer Manage Res* 6: 205-216 (2014); Kinose, Y., et al., *Biomed Res Int* 2014:249393; Humphries, B. & Yang, C., *Oncotarget* 6: 6472-6498 (2015); Muralidhar, G. & Barbolina, M., *Int J Mot Sci* 16: 16833-16847 (2015); Murphy, D. A., & Courtneidge, S. A., *Nat Rev* 12: 413-426 (2011)).

The present disclosure demonstrates that miR200c overexpressing immune cells (i.e., CTLs) exhibited an increase in CTL survival, proliferation, and TNF production in vitro compared to native CTLs, without impairing their cytotoxicity. Moreover, CTLs overexpressing miR200c significantly augmented anti-tumor function in preclinical ACT models of both solid and liquid malignancies. In some embodiments, miR200c nucleic acid sequence may be derived from a vertebrate species including, but not limited to humans, primates, rodents, cows, sheep, canines, felines, zebrafish etc.

The nucleic acid sequence of the human miR200c stem-loop is set forth in SEQ ID NO: 25, as provided below:

```
NR_029779.1 Homo sapiens microRNA 200c (MIR200C),
microRNA
                                   (SEQ ID NO: 25)
CCCTCGTCTTACCCAGCAGTGTTTGGGTGCGGTTGGGAGTCTCTAATAC

TGCCGGGTAATGATGGAGG
```

The nucleic acid sequence of the murine miR200c stem-loop is set forth in SEQ ID NO: 26, as provided below:

```
NR_029792.1 Mus musculus microRNA 200c (Mir200c),
microRNA
                                   (SEQ ID NO: 26)
CCCTCGTCTTACCCAGCAGTGTTTGGGTGCTGGTTGGGAGTCTCTAATA

CTGCCGGGTAATGATGGAGG
```

The engineered immune cells disclosed herein comprise a heterologous mammalian miR200c nucleic acid sequence. In some embodiments, miR200c nucleic acid sequence may be human, primate, murine, bovine, ovine, canine, feline etc.

In some embodiments, the engineered immune cells comprise a heterologous nucleic acid sequence that is at least 80%, 85%, 90%, 95%, 96%, 97%, 98%, or 99% identical to SEQ ID NO: 25 or SEQ ID NO: 26.

Additionally or alternatively, in some embodiments, the expression levels and/or activity of miR200c in the engineered immune cell is at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, or at least 1000 times higher compared to that observed in a native immune cell, wherein the engineered immune cell is of the same lineage as the native immune cell.

EpCAM

Human epithelial cell adhesion molecule (EpCAM) is a 314 aa transmembrane glycoprotein, that contains a large extracellular domain (N-terminal), a single-spanning trans-membrane domain and a short cytoplasmic domain (C-terminal). The EpCAM gene is conserved in many species including mouse, rat and zebrafish. The EpCAM protein shows up to 81% amino acids sequence homoloyg between human and mouse (Schnell, U., et al., *Biochim Biophys Acta* 1828: 1989-2001 (2013)). Tissue distribution of EpCAM has been widely studied by immunohistochemical staining (Momburg F., et al., *Cancer Res* 47: 2883-2891 (1987)). In healthy adults, EpCAM is expressed in many kinds of epithelial tissues, mostly in organs and glands with the colon showing the highest expression. Generally, EpCAM expression is relatively high in proliferating cells and low in more differentiated cells (Martowicz A., et al., *Mol Cancer* 12: 56 (2013)). In addition, overexpression of EpCAM is observed in the majority of cancer tissues, and has been used as a prognostic marker (Went, P., et al., *Hum Pathol* 35: 122-128 (2004)).

Epithelial to Mesenchymal Transition (EMT) is a process of cell remodeling critical during embryonic development and organogenesis. It is a complex program governed by specific transcription factors, miRNA, epigenetic and post-translational regulators. During an EMT, epithelial cells lose their polarized organization and acquire migratory and invasive capabilities. Many studies have established downregulation of EpCAM during EMT (JoJovic, M., et al., *Histochem J* 30: 723-729 (1998); Santisteban, M., et al., *Cancer Res* 69: 2887-2895 (2009); Taube J., et al., *Proc Natl Acad Sci* 107: 15449-15454 (2010); Hyun K., et al., *Oncotarget* 7: 24677-24687 (2016)).

Many transcription factor binding sites within the promoter region of human EpCAM have been reported (McLaughlin P., et al., *Cancer Gene Ther* 11: 603-612). Transcription of EpCAM can be activated by TCF/β-catenin pathway via the binding of TCF-4 to two TCF binding elements in the EpCAM promoter (Yamashita T, et al., *Cancer Res* 67: 10831-10839 (2007)). Several miRNAs controlling EpCAM mRNA expression have been identified. miRNA200c was shown to induce expression of EpCAM mRNA and protein (Massoner P, et al., *Br J Cancer* 111: 955-964 (2014)). ZEB1 is an EMT-inducing transcription factor and a key regulator of the EMT factor network. ZEB1 binds to the EpCAM promoter, resulting in repression of EpCAM expression (Vannier, C., et al., *J Biol Chem* 288: 18643-18659 (2013)). It was found that miR200 family members inhibit EMT by blocking expression of the transcription factor Zeb1 (Gregory, P., et al., *Nat Cell Blot* 10: 593-601 (2008)).

The present disclosure demonstrates that EpCAM over-expressing immune cells (i.e., CTLs) exhibited an increase in CTL survival, proliferation, and TNF production in vitro compared to native CTLs, without impairing their cytotoxicity. Moreover, CTLs overexpressing EpCAM significantly augmented anti-tumor function in preclinical ACT models of both solid and liquid malignancies.

The engineered immune cells disclosed herein comprise a heterologous mammalian EpCAM nucleic acid sequence. In some embodiments, EpCAM nucleic acid sequence may be human, primate, murine, bovine, ovine, canine, feline etc.

An exemplary nucleic acid sequence of human EpCAM is set forth in SEQ ID NO: 27, as provided below:

```
>NM_002354.3 Homo sapiens epithelial cell adhesion molecule (EPCAM), mRNA
                                                      (SEQ ID NO: 27)
ACAGAGCGCTAGTCCTTCGGCGAGCGAGCACCTTCGACGCGGTCCGGGGACCCCCTCGTCGCTGTCCTCC

CGACGCGGACCCGCGTGCCCCAGGCCTCGCGCTGCCCGGCCGGCTCCTCGTGTCCCACTCCCGGCGCACG

CCCTCCCGCGAGTCCCGGGCCCCTCCCGCGCCCCTCTTCTCGGCGCGCGCGCAGCATGGCGCCCCGCAG

GTCCTCGCGTTCGGGCTTCTGCTTGCCGCGGCGACGGCGACTTTTGCCGCAGCTCAGGAAGAATGTGTCT

GTGAAAACTACAAGCTGGCCGTAAACTGCTTTGTGAATAATAATCGTCAATGCCAGTGTACTTCAGTTGG

TGCACAAAATACTGTCATTTGCTCAAAGCTGGCTGCCAAATGTTTGGTGATGAAGGCAGAAATGAATGGC

TCAAAACTTGGGAGAAGAGCAAAACCTGAAGGGGCCCTCCAGAACAATGATGGGCTTTATGATCCTGACT

GCGATGAGAGCGGGCTCTTTAAGGCCAAGCAGTGCAACGGCACCTCCATGTGCTGGTGTGTGAACACTGC

TGGGGTCAGAAGAACAGACAAGGACACTGAAATAACCTGCTCTGAGCGAGTGAGAACCTACTGGATCATC

ATTGAACTAAAACACAAAGCAAGAGAAAAACCTTATGATAGTAAAAGTTTGCGGACTGCACTTCAGAAGG

AGATCACAACGCGTTATCAACTGGATCCAAAATTTATCACGAGTATTTTGTATGAGAATAATGTTATCAC

TATTGATCTGGTTCAAAATTCTTCTCAAAAAACTCAGAATGATGTGGACATAGCTGATGTGGCTTATTAT

TTTGAAAAAGATGTTAAAGGTGAATCCTTGTTTCATTCTAAGAAAATGGACCTGACAGTAAATGGGGAAC

AACTGGATCTGGATCCTGGTCAAACTTTAATTTATTATGTTGATGAAAAAGCACCTGAATTCTCAATGCA

GGGTCTAAAAGCTGGTGTTATTGCTGTTATTGTGGTTGTGGTGATAGCAGTTGTTGCTGGAATTGTTGTG

CTGGTTATTTCCAGAAAGAAGAGAATGGCAAAGTATGAGAAGGCTGAGATAAAGGAGATGGGTGAGATGC

ATAGGGAACTCAATGCATAACTATATAATTTGAAGATTATAGAAGAAGGGAAATAGCAAATGGACACAAA

TTACAAATGTGTGTGCGTGGGACGAAGACATCTTTGAAGGTCATGAGTTTGTTAGTTTAACATCATATAT

TTGTAATAGTGAAACCTGTACTCAAAATATAAGCAGCTTGAAACTGGCTTTACCAATCTTGAAATTTGAC
```

-continued

```
CACAAGTGTCTTATATATGCAGATCTAATGTAAAATCCAGAACTTGGACTCCATCGTTAAAATTATTTAT

GTGTAACATTCAAATGTGTGCATTAAATATGCTTCCACAGTAAAATCTGAAAAACTGATTTGTGATTGAA

AGCTGCCTTTCTATTTACTTGAGTCTTGTACATACATACTTTTTTATGAGCTATGAAATAAAACATTTTA

AACTGAA
```

An exemplary nucleic acid sequence of murine EpCAM
is set forth in SEQ ID NO: 28, as provided below:

```
>NM_008532.2 Mus musculus epithelial cell adhesion molecule (Epcam), mRNA
                                                          (SEQ ID NO: 28)
GCACTTCTTCCCTCTGATGGACTGATTCTGCACGTGAGACCTGCGGCGGCGGCGGCGGCGGCTGCTGCAG

CTGCAGCTGCATGTTTCACTAGAGGAAGTTCTCGGTTTGACTTGGTATCCCTTTCGGCTTTCACGTCCAG

TCTCGTCCGTGTGTCCGCGACATCCGGTCCTTCCGGGGTACTGGAATCCCCGCCTCTGGTCCGGGACAGC

GCACACCTGGAGAGGGGGCGAGGTGGGGCGGGTGAGTCACCGCGGGCGAGCGGGCGGGTGGGCGGGCGAG

CGGAGGTGAGGGCGGGGAGGGGCGTGGCCGGCCGCCGGGGCAGCAGATCCGCAGGTCCGCTCCCGCCTCG

CCGCGCGCACAGCGCTCAGTCCGTCCGCCGCCGCGCAGCGCGACTGTCCTCCGAGCCGTCCCGCGCCGCA

CCTCCGCGAGTCGCCCTCGCCGCTCCGCGCGCAGCATGGCGGGTCCCCAGGCCCTCGCGTTCGGGCTCCT

GCTCGCGGTGGTCACAGCGACGCTGGCCGCGGCTCAGAGAGACTGTGTCTGTGACAACTACAAGCTGGCA

ACAAGTTGCTCTCTGAATGAATATGGTGAATGCCAGTGTACTTCCTATGGTACACAGAATACTGTCATTT

GCTCCAAACTGGCGTCTAAATGCTTGGCGATGAAAGCAGAAATGACTCACAGCAAGTCTGGGAGGAGGAT

AAAGCCCGAAGGGGCGATCCAGAACAACGATGGGCTGTACGACCCCGACTGCGACGAGCAGGGGCTCTTC

AAAGCCAAGCAGTGCAACGGCACCGCCACGTGCTGGTGTGTCAACACCGCCGGAGTCCGAAGAACCGACA

AGGACACGGAGATCACGTGCTCCGAGCGCGTGAGGACCTACTGGATCATCATTGAACTAAAACACAAAGA

AAGAGAAAGCCCCTACGACCATCAGAGCTTGCAGACTGCGCTTCAAGAGGCGTTCACATCTCGATATAAG

CTGAATCAGAAATTTATCAAAAACATTATGTATGAGAATAATGTTATCACCATTGATCTGATGCAAAACT

CTTCTCAGAAAACACAAGACGACGTGGACATAGCTGATGTGGCTTACTATTTTGAAAAAGATGTGAAGGG

GGAGTCCCTGTTCCATTCTTCTAAGAGCATGGACCTGAGAGTGAACGGAGAGCCGCTCGATCTGGACCCC

GGGCAGACTCTGATTTACTACGTTGATGAAAAGGCACCCGAGTTCTCCATGCAGGGCCTCACGGCCGGGA

TCATCGCTGTCATTGTGGTGGTGTCATTAGCAGTCATCGCGGGGATTGTTGTCCTGGTTATATCTACAAG

GAAGAAATCAGCAAAATATGAGAAGGCTGAGATAAAGGAGATGGGTGAGATCCACAGAGAGCTTAATGCC

TAGCCGTGCTGAGTGCTGAACTGAGGAGGGGCCGCCCGACCGGAAGTGGCAGAAGAGCTCGGACTGCAGA

TGTATAAACCTGGGGAAGATGAAGACCTGCGAAGGGTTACTGCTTTGATAGTTACTTTGTTAGTTTCACA

TTTGTAACAGTGAAATTTGTACTCGTAAATACAAGCAGCTGGACACCGGCATTACCGATCGTAAAATTAG

ACGAACGTCTTATAGGTGCAGGTCCAGTGTGGTACTCAGAACTTAGCCTGCAAAGTTAAGAGAGTTGATG

CTTATTATGACAGAGTGTGCGTCGCAAACATTCCAACAGTAGAATGCGGTGACTAGTCTCATTTTTTTTT

TTTTTTTGTGATTAAGGCTGCCCTTCTATATACCTGAGTCTTGTACATAATAAACTTTTTTTTAATGAAA

TAAAACATTTTAAAGTGAGTTTCTAAGTTTGTTTGAATCAAATTTTCCTAGCATGTGCATAATTAAGATA

ATAGATGTCTAAATGCTCTGGCACTGCTAACTGGTACAAACCTGTAATTCTGTACTTGGGAGGTAGAGGT

AGGAGGGGTTAGCGCTTCCGAGGTAGCTGCTGTGTATCTGCTCTGCCACTGACTGGCCTTGACTATCCAAC

ACCCTATCTGAAAGAAATAAAAATCAAACTT
```

An exemplary amino acid sequence of human EpCAM is set forth in SEQ ID NO: 29, as provided below:

```
NP_002345.2 epithelial cell adhesion molecule precursor [Homo sapiens]
                                                        (SEQ ID NO: 29)
MAPPQVLAFGLLLAAATATFAAAQEECVCENYKLAVNCFVNNNRQCQCTSVGAQNTVICSKLAAKCLVMK

AEMNGSKLGRRAKPEGALQNNDGLYDPDCDESGLFKAKQCNGTSMCWCVNTAGVRRTDKDTEITCSERVR

TYWIIIELKHKAREKPYDSKSLRTALQKEITTRYQLDPKFITSILYENNVITIDLVQNSSQKTQNDVDIA

DVAYYFEKDVKGESLFHSKKMDLTVNGEQLDLDPGQTLIYYVDEKAPEFSMQGLKAGVIAVIVVVVIAVV

AGIVVLVISRKKRMAKYEKAEIKEMGEMHRELNA
```

An exemplary amino acid sequence of murine EpCAM is set forth in SEQ ID NO: 30, as provided below:

```
NP_032558.2 epithelial cell adhesion molecule precursor [Mus musculus]
                                                        (SEQ ID NO: 30)
MAGPQALAFGLLLAVVTATLAAAQRDCVCDNYKLATSCSLNEYGECQCTSYGTQNTVICSKLASKCLAMK

AEMTHSKSGRRIKPEGAIQNNDGLYDPDCDEQGLFKAKQCNGTATCWCVNTAGVRRTDKDTEITCSERVR

TYWIIIELKHKERESPYDHQSLQTALQEAFTSRYKLNQKFIKNIMYENNVITIDLMQNSSQKTQDDVDIA

DVAYYFEKDVKGESLFHSSKSMDLRVNGEPLDLDPGQTLIYYVDEKAPEFSMQGLTAGIIAVIVVVSLAV

IAGIVVLVISTRKKSAKYEKAEIKEMGEIHRELNA
```

In some embodiments, the engineered immune cells comprise a heterologous nucleic acid sequence that is at least 80%, 85%, 90%, 95%, 96%, 97%, 98%, or 99% identical to SEQ ID NO: 27 or SEQ ID NO: 28, or is at least 80%, 85%, 90%, 95%, 96%, 97%, 98%, or 99% identical to a nucleic acid encoding the EpCAM polypeptide of SEQ ID NO: 29 or SEQ ID NO: 30. Additionally or alternatively, in some embodiments, the expression levels and/or activity of EpCAM in the engineered immune cell is at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, or at least 1000 times higher compared to that observed in a native immune cell, wherein the engineered immune cell is of the same lineage as the native immune cell.

Polynucleotides, Polypeptides and Analogs

Also included in the presently disclosed subject matter are EpCAM and/or miR200c polynucleotides and their corresponding polypeptides or fragments that may be modified in ways that enhance their anti-tumor activity when expressed in an engineered immune cell. The presently disclosed subject matter provides methods for optimizing an amino acid sequence or a nucleic acid sequence by producing an alteration in the sequence. Such alterations can comprise certain mutations, deletions, insertions, or post-translational modifications. The presently disclosed subject matter further comprises analogs of any naturally-occurring polypeptide of the presently disclosed subject matter. Analogs can differ from a naturally-occurring polypeptide of the presently disclosed subject matter by amino acid sequence differences, by post-translational modifications, or by both. Analogs of the presently disclosed subject matter can generally exhibit at least about 85%, about 90%, about 91%, about 92%, about 93%, about 94%, about 95%, about 96%, about 97%), about 98%, about 99% or more identity or homology with all or part of a naturally-occurring amino, acid sequence of the presently disclosed subject matter. The length of sequence comparison is at least about 5, about 10, about 15, about 20, about 25, about 50, about 75, about 100 or more amino acid residues. Again, in an exemplary approach to determining the degree of identity, a BLAST program can be used, with a probability score between $e^{-3}$ and $e^{-100}$ indicating a closely related sequence. Modifications comprise in vivo and in vitro chemical derivatization of polypeptides, e.g., acetylation, carboxylation, phosphorylation, or glycosylation; such modifications can occur during polypeptide synthesis or processing or following treatment with isolated modifying enzymes. Analogs can also differ from the naturally-occurring polypeptides of the presently disclosed subject matter by alterations in primary sequence. These include genetic variants, both natural and induced (for example, resulting from random mutagenesis by irradiation or exposure to ethanemethyl sulfate or by site-specific mutagenesis as described in Sambrook, Fritsch and Maniatis, Molecular Cloning: A Laboratory Manual (2nd ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., beta (β) or gamma (γ) amino acids.

In addition to full-length polypeptides, the presently disclosed subject matter also provides fragments of any one of the polypeptides or peptide domains of the presently disclosed subject matter. A fragment can be at least about 5, about 10, about 13, or about 15 amino acids. In some embodiments, a fragment is at least about 20 contiguous amino acids, at least about 30 contiguous amino acids, or at least about 50 contiguous amino acids. In some embodiments, a fragment is at least about 60 to about 80, about 100, about 200, about 300 or more contiguous amino acids. Fragments of the presently disclosed subject matter can be generated by methods known to those of ordinary skill in the art or can result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein. Such analogs are administered according to methods of the presently disclosed subject matter. Such analogs can exceed the physiological activity of the original polypeptide. Methods of analog design are well known in the art, and synthesis of analogs can be carried out according to such methods by modifying the chemical structures such that the resultant analogs increase the antineoplastic activity of the original polypeptide when expressed in an engineered immune cell. These chemical modifications include, but are not limited to, substituting alternative R groups and varying the degree of saturation at specific carbon atoms of a reference polypeptide. The protein analogs can be relatively resistant to in vivo degradation, resulting in a more prolonged therapeutic effect upon administration. Assays for measuring functional activity include, but are not limited to, those described in the Examples below.

In accordance with the presently disclosed subject matter, the polynucleotides encoding miR200c and/or EpCAM can be modified by codon optimization. Codon optimization can alter both naturally occurring and recombinant gene sequences to achieve the highest possible levels of productivity in any given expression system. Factors that are involved in different stages of protein expression include codon adaptability, mRNA structure, and various cis-elements in transcription and translation. Any suitable codon optimization methods or technologies that are known to ones skilled in the art can be used to modify the polynucleotides of the presently disclosed subject matter, including, but not limited to, OptimumGene™, Encor optimization, and Blue Heron.

Vectors

As used herein, a "vector" is a replicable nucleic acid from which one or more heterologous proteins or RNAs can be expressed when the vector is introduced into an appropriate host cell. The vector is used to introduce the nucleic acid encoding the polypeptide or RNA into the host cell for amplification of the nucleic acid or for expression/display of the polypeptide or RNA encoded by the nucleic acid. As used herein, a vector also includes "virus vectors" or "viral vectors." Viral vectors are engineered viruses that are operatively linked to exogenous genes to transfer (as vehicles or shuttles) the exogenous genes into cells.

Many expression vectors are available and known to those of skill in the art and can be used for nonendogenous expression of miR200c and/or EpCAM. The choice of expression vector will be influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vector in the cells. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art.

Vectors also can contain additional nucleotide sequences operably linked to the ligated nucleic acid molecule, such as, for example, an epitope tag such as for localization, e.g. a hexa-his tag (SEQ ID NO: 31) or a myc tag, hemagglutinin tag or a tag for purification, for example, a GST fusion, and a sequence for directing protein secretion and/or membrane association.

Expression of the miR200c and/or EpCAM genes can be controlled by any promoter/enhancer known in the art. Suitable bacterial promoters are well known in the art and described herein below. Other suitable promoters for mammalian cells, yeast cells and insect cells are well known in the art and some are exemplified below. Selection of the promoter used to direct expression of a heterologous nucleic acid depends on the particular application and is within the level of skill of the skilled artisan. Promoters which can be used include but are not limited to eukaryotic expression vectors containing the SV40 early promoter (Bernoist and Chambon, *Nature* 290:304-310(1981)), the promoter contained in the 3' long terminal repeat of Rous sarcoma virus (Yamamoto et al. (1980) *Cell* 22:787-797), the herpes thymidine kinase promoter (Wagner et al. (1981) *Proc. Natl. Acad. Sci. USA* 75: 1441-1445), the regulatory sequences of the metallothionein gene (Brinster et al. (1982) *Nature* 296:39-42); prokaryotic expression vectors such as the β-lactamase promoter (Jay et al. (1981) *Proc. Natl. Acad. Sci. USA* 75:5543) or the tac promoter (DeBoer et al. (1983) *Proc. Natl. Acad. Sci. USA* 50:21-25); see also "Useful Proteins from Recombinant Bacteria" (1980) in *Scientific American* 242:79-94); plant expression vectors containing the nopaline synthetase promoter (Herrera-Estrella et al. (1984) *Nature* 505:209-213) or the cauliflower mosaic virus 35S RNA promoter (Gardner et al. (1981) *Nucleic Acids Res.* 9:2871), and the promoter of the photosynthetic enzyme ribulose bisphosphate carboxylase (Herrera-Estrella et al. (1984) *Nature* 510: 115-120); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al. (1984) *Cell* 55:639-646; Ornitz et al. (1986) *Cold Spring Harbor Symp. Quant. Biol.* 50:399-409; MacDonald (1987) *Hepatology* 7:425-515); insulin gene control region which is active in pancreatic beta cells (Hanahan et al. (1985) *Nature* 515: 115-122), immunoglobulin gene control region which is active in lymphoid cells (Grosschedl et al. (1984) *Cell* 55:647-658; Adams et al. (1985) *Nature* 515:533-538; Alexander et al. (1987) *Mol. Cell Biol.* 7: 1436-1444), mouse mammary tumor virus control region which is active in testicular, breast, lymphoid and mast cells (Leder et al. (1986) *Cell* 15:485-495), albumin gene control region which is active in liver (Pinckert et al. (1987) *Genes and Devel.* 1:268-276), alpha-fetoprotein gene control region which is active in liver (Krumlauf et al. (1985) *Mol. Cell. Biol.* 5:1639-403); Hammer et al. (1987) *Science* 255:53-58), alpha-1 antitrypsin gene control region which is active in liver (Kelsey et al. (1987) *Genes and Devel.* 7:161-171), beta globin gene control region which is active in myeloid cells (Magram et al. (1985) *Nature* 515: 338-340); Kollias et al. (1986) *Cell* 5:89-94), myelin basic protein gene control region which is active in oligodendrocyte cells of the brain (Readhead et al. (1987) Cell 15:703-712), myosin light chain-2 gene control region which is active in skeletal muscle (Shani (1985) *Nature* 514:283-286), and gonadotrophic releasing hormone gene control region which is active in gonadotrophs of the hypothalamus (Mason et al. (1986) *Science* 254: 1372-1378).

In addition to the promoter, the expression vector typically contains a transcription unit or expression cassette that contains all the additional elements required for the expression of the heterologous nucleic acid, in host cells. A typical expression cassette contains a promoter operably linked to the gene sequence and signals required for efficient poly-adenylation of the transcript, ribosome binding sites and translation termination. Additional elements of the cassette can include enhancers. In addition, the cassette typically contains a transcription termination region downstream of the structural gene to provide for efficient termination. The termination region can be obtained from the same gene as the promoter sequence or can be obtained from different genes.

Some expression systems have markers that provide gene amplification such as thymidine kinase and dihydrofolate reductase. Alternatively, high yield expression systems not involving gene amplification are also suitable, such as using a baculovirus vector in insect cells, with a nucleic acid sequence encoding a polypeptide under the direction of the polyhedron promoter or other strong baculovirus promoter.

Any methods known to those of skill in the art for the insertion of DNA fragments into a vector can be used to construct expression vectors containing a nucleic acid encoding any of the genes disclosed herein. These methods can include in vitro recombinant DNA and synthetic techniques and in vivo recombinants (genetic recombination). The insertion into a cloning vector can, for example, be accomplished by ligating the DNA fragment into a cloning vector which has complementary cohesive termini. If the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can contain specific chemically synthesized nucleic acids encoding restriction endonuclease recognition sequences.

Exemplary plasmid vectors useful to produce the transcripts or polypeptides provided herein contain a strong promoter, such as the HCMV immediate early enhancer/promoter or the MHC class I promoter, an intron to enhance processing of the transcript, such as the HCMV immediate early gene intron A, and a polyadenylation (poly A) signal, such as the late SV40 polyA signal.

Genetic modification of engineered immune cells (e.g., T cells, NK cells) can be accomplished by transducing a substantially homogeneous cell composition with a recombinant DNA or RNA construct. The vector can be a retroviral vector (e.g., gamma retroviral), which is employed for the introduction of the DNA or RNA construct into the host cell genome. For example, a polynucleotide encoding EpCAM and/or miR200c can be cloned into a retroviral vector and expression can be driven from its endogenous promoter, from the retroviral long terminal repeat, or from an alternative internal promoter.

Non-viral vectors or RNA can be used as well. Random chromosomal integration, or targeted integration (e.g., using a nuclease, transcription activator-like effector nucleases (TALEN5), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide miR200c and/or EpCAM overexpressing cells, a retroviral vector can be employed for transduction. However, any other suitable viral vector or non-viral delivery system can be used for genetic modification of cells. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller et al. (1985) *Mol. Cell. Biol.* 5:431-437); PA317 (Miller et al. (1986) *Mol. Cell. Biol.* 6:2895-2902); and CRIP (Danos et al. (1988) *Proc. Natl. Acad. Sci. USA* 85:6460-6464). Non-amphotropic particles are suitable too, e.g., particles pseudo-typed with VSVG, RD114 or GALV envelope and any other known in the art.

Possible methods of transduction also include direct co-culture of the cells with producer cells, e.g., by the method of Bregni et al. (1992) *Blood* 80: 1418-1422, or culturing with viral supernatant alone or concentrated vector stocks with or without appropriate growth factors and polycations, e.g., by the method of Xu et al. (1994) *Exp. Hemat.* 22:223-230; and Hughes et al. (1992) *J. Clin. Invest.* 89: 1817.

Transducing viral vectors can be used to express a co-stimulatory ligand and/or secretes a cytokine (e.g., 4-1BBL and/or IL-12) in an engineered immune cell. In some embodiments, the chosen vector exhibits high efficiency of infection and stable integration and expression (see, e.g., Cayouette et al. (1997) *Human Gene Therapy* 8:423-430; Kido et al. (1996) *Current Eye Research* 15:833-844; Bloomer et al. (1997) *Journal of Virology* 71:6641-6649; Naldini et al. (1996) Science 272:263 267; and Miyoshi et al. (1997) *Proc. Natl. Acad. Sci. U.S.A.* 94: 10319). Other viral vectors that can be used include, for example, adeno-viral, lentiviral, and adeno-associated viral vectors, vaccinia virus, a bovine papilloma virus, or a herpes virus, such as Epstein-Barr Virus (also see, for example, the vectors of Miller (1990) *Human Gene Therapy* 15-14, Friedman (1989) *Science* 244: 1275-1281; Eglitis et al. (1988) *Bio-Techniques* 6:608-614; Tolstoshev et al. (1990) *Current Opinion in Biotechnology* 1:55-61; Sharp (1991) *The Lancet* 337: 1277-1278; Cornetta et al. (1987) *Nucleic Acid Research and Molecular Biology* 36:311-322; Anderson (1984) *Science* 226:401-409; Moen (1991) *Blood Cells* 17:407-416; Miller et al. (1989) *Biotechnology* 7:980-990; Le Gal La Salle et al. (1993) *Science* 259:988-990; and Johnson (1995) *Chest* 107:77S-83S). Retroviral vectors are particularly well developed and have been used in clinical settings (Rosenberg et al. (1990) *N. Engl. J. Med* 323:370; Anderson et al., U.S. Pat. No. 5,399,346).

In certain non-limiting embodiments, the vector expressing miR200c and/or EpCAM is a retroviral vector, e.g., an oncoretroviral vector. In some instances, the retroviral vector is a SFG retroviral vector or murine stem cell virus (MSCV) retroviral vector. In certain non-limiting embodiments, the vector expressing a miR200c and/or EpCAM nucleic acid sequence is a lentiviral vector. In certain non-limiting embodiments, the vector expressing a miR200c and/or EpCAM nucleic acid sequence is a transposon vector.

Non-viral approaches can also be employed for the expression of a protein in cell. For example, a nucleic acid molecule can be introduced into a cell by administering the nucleic acid in the presence of lipofection (Feigner et al. (1987) *Proc. Nat'l. Acad. Sci. U.S.A.* 84:7413; Ono et al. (1990) *Neuroscience Letters* 17:259; Brigham et al. (1989) *Am. J. Med. Sci.* 298:278; Staubinger et al. (1983) *Methods in Enzymology* 101:512), asialoorosomucoid-polylysine conjugation (Wu et al. (1988) *Journal of Biological Chemistry* 263: 14621; Wu et al. (1989) *Journal of Biological*

*Chemistry* 264: 16985), or by micro-injection under surgical conditions (Wolff et al. (1990) *Science* 247: 1465). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g., Zinc finger nucleases, meganucleases, or TALE nucleases). Transient expression can be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g., the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

Engineered Immune Cells

The presently disclosed subject matter provides engineered immune cells that overexpress miR200c and/or EpCAM. In some embodiments, the engineered immune cells may further comprise an engineered receptor (e.g., a CAR, caTCR, or eTCR) or other ligand that comprises an extracellular antigen-binding domain, a transmembrane domain and an intracellular domain, where the extracellular antigen-binding domain specifically binds a tumor antigen, including a tumor receptor or ligand. In certain embodiments, immune cells can be transduced with a vector comprising nucleic acid sequences that encode miR200c and/or EpCAM.

The presently disclosed subject matter also provides methods of using such cells for the treatment of a tumor. The engineered immune cells of the presently disclosed subject matter can be cells of the lymphoid lineage or myeloid lineage. Examples of myeloid cells include but are not limited to, mast cells, monocytes, macrophages, dendritic cells, eosinophils, neutrophils, basophils. The lymphoid lineage, comprising B, T, and natural killer (NK) cells, provides for the production of antibodies, regulation of the cellular immune system, detection of foreign agents in the blood, detection of cells foreign to the host, and the like. Non-limiting examples of immune cells of the lymphoid lineage include T cells, Natural Killer (NK) cells, embryonic stem cells, and pluripotent stem cells (e.g., those from which lymphoid cells can be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, T helper cells, cytotoxic T cells, memory T cells (including central memory T cells, stem-cell-like memory T cells (or stem-like memory T cells), and two types of effector memory T cells: e.g., $T_{EM}$ cells and TEMRA cells, Regulatory T cells (also known as suppressor T cells), Natural killer T cells, Mucosal associated invariant T cells, and γδ T cells. Cytotoxic T cells (CTL or killer T cells) are a subset of T lymphocytes capable of inducing the death of infected somatic or tumor cells.

Natural killer (NK) cells can be lymphocytes that are part of cell-mediated immunity and act during the innate immune response. NK cells do not require prior activation in order to perform their cytotoxic effect on target cells.

The engineered immune cells of the presently disclosed subject matter can express non-endogenous levels of miR200c and/or EpCAM for the treatment of cancer, e.g., for treatment of solid tumor. Such engineered immune cells can be administered to a subject (e.g., a human subject) in need thereof for the treatment of cancer. In some embodiments, the immune cell is a lymphocyte, such as a T cell, a B cell or a natural killer (NK) cell. In certain embodiments, the engineered immune cell is a T cell. The T cell can be a CD4$^+$ T cell or a CD8$^+$ T cell. In certain embodiments, the T cell is a CD4$^+$ T cell. In certain embodiments, the T cell is a CD8$^+$ T cell.

The presently disclosed engineered immune cells of the present technology may further include at least one recombinant or exogenous co-stimulatory ligand. For example, the presently disclosed engineered immune cells can be further transduced with at least one co-stimulatory ligand, such that the engineered immune cells co-expresses or is induced to co-express miR200c and/or EpCAM and the at least one co-stimulatory ligand. Co-stimulatory ligands include, but are not limited to, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. TNF superfamily members include, without limitation, nerve growth factor (NGF), CD40L (CD40L)/CD 154, CD137L/4-1BBL, TNF-a, CD134L/OX40L/CD252, CD27L/CD70, Fas ligand (FasL), CD30L/CD153, tumor necrosis factor beta (TNFP)/lymphotoxin-alpha (LTa), lymphotoxin-beta O-Tβ), CD257/B cell-activating factor (B AFF)/Bly s/THANK/Tall-1, glucocorticoid-induced TNF Receptor ligand (GITRL), and T F-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, but are not limited to, CD80 and CD86, both ligands for CD28, PD-L1/(B7-H1) that ligands for PD-1. In certain embodiments, the at least one co-stimulatory ligand is selected from the group consisting of 4-1BBL, CD80, CD86, CD70, OX40L, CD48, TNFRSF14, PD-L1, and combinations thereof.

Furthermore, the presently disclosed engineered immune cells can further comprise at least one exogenous cytokine. For example, a presently disclosed engineered immune cell can be further transduced with at least one cytokine, such that the engineered immune cells secrete the at least one cytokine as well as express miR200c and/or EpCAM. In certain embodiments, the at least one cytokine is selected from the group consisting of IL-2, IL-3, IL-6, IL-7, IL-11, IL-12, IL-15, IL-17, and IL-21. In certain embodiments, the cytokine is IL-12.

The engineered immune cells can be generated from peripheral donor lymphocytes, e.g., those disclosed in Sadelain, M., et al., *Nat Rev Cancer* 3:35-45 (2003), in Morgan, R. A. et al. (2006) *Science* 314: 126-129, in Panelli et al. (2000) *J Immunol* 164:495-504; Panelli et al. (2000) *J Immunol* 164:4382-4392 (2000), and in Dupont et al. (2005) *Cancer Res* 65:5417-5427; Papanicolaou et al. (2003) *Blood* 102:2498-2505. The engineered immune cells (e.g., T cells) can be autologous, non-autologous (e.g., allogeneic), or derived in vitro from engineered progenitor or stem cells.

In certain embodiments, the presently disclosed engineered immune cells (e.g., T cells) expresses from about 1 to about 5, from about 1 to about 4, from about 2 to about 5, from about 2 to about 4, from about 3 to about 5, from about 3 to about 4, from about 4 to about 5, from about 1 to about 2, from about 2 to about 3, from about 3 to about 4, or from about 4 to about 5 vector copy numbers per cell of a miR200c and/or EpCAM heterologous nucleic acid.

For example, the higher the non-endogenous levels of miR200c and/or EpCAM in an engineered immune cell, the greater cytotoxicity and/or cytokine production the engineered immune cell exhibits. Additionally, or alternatively, the cytotoxicity and cytokine production of a presently disclosed engineered immune cell (e.g., T cell) are proportional to the expression level of miR200c and/or EpCAM in the immune cell.

The unpurified source of immune cells can be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-immune cell initially. Monoclonal antibodies are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. In some embodiments, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g., plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). In some embodiments, the cells are collected in a medium comprising 2% fetal calf serum (FCS) or 0.2% bovine serum albumin (BSA) or any other suitable, preferably sterile, isotonic medium.

In some embodiments, the engineered immune cells comprise one or more additional modifications. For example, in some embodiments, the engineered immune cells comprise and express (is transduced to express) a chimeric co-stimulatory receptor (CCR). CCR is described in Krause et al. (1998) *J. Exp. Med.* 188(4):619-626, and US20020018783, the contents of which are incorporated by reference in their entireties. CCRs mimic co-stimulatory signals, but unlike, engineered receptors, do not provide a T-cell activation signal, e.g., CCRs lack a CD3 polypeptide. CCRs provide co-stimulation, e.g., a CD28-like signal, in the absence of the natural co-stimulatory ligand on the antigen-presenting cell. A combinatorial antigen recognition, i.e., use of a CCR in combination with an engineered receptor, can augment T-cell reactivity against the dual-antigen expressing T cells, thereby improving selective tumor targeting.

In some embodiments, the engineered immune cells are further modified to suppress expression of one or more genes. In some embodiments, the engineered immune cells are further modified via genome editing. Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20050064474; 20060063231; 201000218264; 20120017290; 20110265198; 20130137104; 20130122591; 20130177983 and 20130177960, the disclosures of which are incorporated by reference in their entireties. These methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). Cleavage can occur through the use of specific nucleases such as engineered zinc finger nucleases (ZEN), transcription-activator like effector nucleases (TALEN5), or using the CRISPR/Cas system with an engineered crRNA/tracr RNA ('single guide RNA') to guide specific cleavage. In some embodiments, the engineered immune cells are modified to disrupt or reduce expression of an endogenous T-cell receptor gene (see, e.g. WO 2014153470, which is incorporated by reference in its entirety). In some embodiments, the engineered immune cells are modified to result in disruption or inhibition of PD1, PDL-1 or CTLA-4 (see, e.g. U.S. Patent Publication 20140120622), or other immunosuppressive factors known in the art (Wu et al. (2015) *Oncoimmunology* 4(7): e1016700, Mahoney et al. (2015) *Nature Reviews Drug Discovery* 14, 561-584).

Administration

Engineered immune cells expressing EpCAM or miR200c of the presently disclosed subject matter can be provided systemically or directly to a subject for treating cancer. In certain embodiments, engineered immune cells are directly injected into an organ of interest. Additionally or alternatively, the engineered immune cells are provided indirectly to the organ of interest, for example, by administration into the circulatory system (e.g., the tumor vasculature) or into the tissue of interest (e.g., solid tumor). Expansion and differentiation agents can be provided prior to, during or after administration of cells and compositions to increase production of the engineered immune cells either in vitro or in vivo.

Engineered immune cells of the presently disclosed subject matter can be administered in any physiologically acceptable vehicle, systemically or regionally, normally intravascularly, intraperitoneally, intrathecally, or intrapleurally, although they may also be introduced into bone or other convenient site where the cells may find an appropriate site for regeneration and differentiation (e.g., thymus). In certain embodiments, at least $1 \times 10^5$ cells can be administered, eventually reaching $1 \times 10^{10}$ or more. In certain embodiments, at least $1 \times 10^6$ cells can be administered. A cell population comprising engineered immune cells can comprise a purified population of cells. Those skilled in the art can readily determine the percentage of engineered immune cells in a cell population using various well-known methods, such as fluorescence activated cell sorting (FACS). The ranges of purity in cell populations comprising engineered immune cells can be from about 50% to about 55%, from about 55% to about 60%, about 60% to about 65%, from about 65% to about 70%, from about 70% to about 75%, from about 75% to about 80%, from about 80% to about 85%; from about 85% to about 90%, from about 90% to about 95%, or from about 95 to about 100%. Dosages can be readily adjusted by those skilled in the art (e.g., a decrease in purity may require an increase in dosage). The engineered immune cells can be introduced by injection, catheter, or the like. If desired, factors can also be included, including, but not limited to, interleukins, e.g., IL-2, IL-3, IL 6, IL-11, IL-7, IL-12, IL-15, IL-21, as well as the other interleukins, the colony stimulating factors, such as G-, M- and GM-CSF, interferons, e.g., γ-interferon.

In certain embodiments, compositions of the presently disclosed subject matter comprise pharmaceutical compositions comprising engineered immune cells overexpressing EpCAM or miR200c with a pharmaceutically acceptable carrier. Administration can be autologous or non-autologous. For example, engineered immune cells expressing EpCAM and/or miR200c and compositions comprising the same can be obtained from one subject, and administered to the same subject or a different, compatible subject. Peripheral blood derived T cells of the presently disclosed subject matter or their progeny (e.g., in vivo, ex vivo or in vitro derived) can be administered via localized injection, including catheter administration, systemic injection, localized injection, intravenous injection, or parenteral administration. When administering a pharmaceutical composition of the presently disclosed subject matter (e.g., a pharmaceutical composition comprising engineered immune cells overexpressing EpCAM or miR200c), it can be formulated in a unit dosage injectable form (solution, suspension, emulsion).

Formulations

Engineered immune cells over-expressing EpCAM or miR200c and compositions comprising the same can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions of the presently disclosed subject matter, e.g., a composition comprising engineered immune cells, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the presently disclosed subject matter, however, any vehicle, diluent, or additive used would have to be compatible with the engineered immune cells of the presently disclosed subject matter.

The compositions can be isotonic, i.e., they can have the same osmotic pressure as blood and lacrimal fluid. The desired isotonicity of the compositions of the presently disclosed subject matter may be accomplished using sodium chloride, or other pharmaceutically acceptable agents such as dextrose, boric acid, sodium tartrate, propylene glycol or other inorganic or organic solutes. Sodium chloride is suitable particularly for buffers containing sodium ions.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the engineered immune cells as described in the presently disclosed subject matter. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of the engineered immune cells of the presently disclosed subject matter is the quantity of cells necessary to achieve an optimal effect. The quantity of cells to be administered will vary for the subject being treated. In certain embodiments, from about $10^2$ to about $10^{12}$, from about $10^3$ to about $10^{11}$, from about $10^4$ to about $10^{10}$, from about $10^5$ to about $10^9$, or from about $10^6$ to about $10^8$ engineered immune cells of the presently disclosed subject matter are administered to a subject. More effective cells may be administered in even smaller numbers. In some embodiments, at least about $1 \times 10^8$, about $2 \times 10^8$, about $3 \times 10^8$, about $4 \times 10^8$, about $5 \times 10^8$, about $1 \times 10^9$, about $5 \times 10^9$, about $1 \times 10^{10}$, about $5 \times 10^{10}$, about $1 \times 10^{11}$, about $5 \times 10^{11}$, about $1 \times 10^{12}$ or more engineered immune cells of the presently disclosed subject matter are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art. Generally, engineered immune cells are administered at doses that are nontoxic or tolerable to the patient.

The skilled artisan can readily determine the amount of cells and optional additives, vehicles, and/or carrier in compositions to be administered in methods of the presently disclosed subject matter. Typically, any additives (in addition to the active cell(s) and/or agent(s)) are present in an amount of from about 0.001% to about 50% by weight) solution in phosphate buffered saline, and the active ingredient is present in the order of micrograms to milligrams, such as from about 0.0001 wt % to about 5 wt %, from about 0.0001 wt % to about 1 wt %, from about 0.0001 wt % to about 0.05 wt %, from about 0.001 wt % to about 20 wt %, from about 0.01 wt % to about 10 wt %, or from about 0.05 wt % to about 5 wt %. For any composition to be administered to an animal or human, and for any particular method of administration, toxicity should be determined, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Therapeutic Uses of the Engineered Immune Cells of the Present Technology

For treatment, the amount of the engineered immune cells provided herein administered is an amount effective in producing the desired effect, for example, treatment of a cancer or one or more symptoms of a cancer. An effective amount can be provided in one or a series of administrations of the engineered immune cells provided herein. An effective amount can be provided in a bolus or by continuous perfusion. For adoptive immunotherapy using antigen-specific T cells, cell doses in the range of about $10^6$ to about $10^{10}$ are typically infused. The engineered immune cells of the presently disclosed subject matter can be administered by any methods known in the art, including, but not limited to, pleural administration, intravenous administration, subcutaneous administration, intranodal administration, intratumoral administration, intrathecal administration, intrapleural administration, intraperitoneal administration, and direct administration to the thymus. In certain embodiments, the engineered immune cells and the compositions comprising thereof are intravenously administered to the subject in need. Methods for administering cells for adoptive cell therapies, including, for example, donor lymphocyte infusion and engineered T cell therapies, and regimens for administration are known in the art and can be employed for administration of the engineered immune cells provided herein.

The presently disclosed subject matter provides various methods of using the engineered immune cells (e.g., T cells) provided herein, overexpressing miR200c and/or EpCAM. In some embodiments, the engineered immune cell is a CAR, caTCR, or eTCR. For example, the presently disclosed subject matter provides methods of reducing tumor burden in a subject. In one non-limiting example, the method of reducing tumor burden comprises administering an effective amount of the presently disclosed engineered immune cells to the subject, thereby inducing tumor cell death in the subject.

The presently disclosed engineered immune cells can reduce the number of tumor cells, reduce tumor size, and/or eradicate the tumor in the subject. In certain embodiments, the method of reducing tumor burden comprises administering an effective amount of engineered immune cells to the subject, thereby inducing tumor cell death in the subject. Non-limiting examples of suitable tumors include adrenal cancers, bladder cancers, blood cancers, bone cancers, brain cancers, breast cancers, carcinoma, cervical cancers, colon cancers, colorectal cancers, corpus uterine cancers, ear, nose and throat (ENT) cancers, endometrial cancers, esophageal cancers, gastrointestinal cancers, head and neck cancers, Hodgkin's disease, intestinal cancers, kidney cancers, larynx cancers, acute and chronic leukemias, liver cancers, lymph node cancers, lymphomas, lung cancers, melanomas, mesothelioma, myelomas, nasopharynx cancers, neuroblastomas, non-Hodgkin's lymphoma, oral cancers, ovarian cancers, pancreatic cancers, penile cancers, pharynx cancers, prostate cancers, rectal cancers, sarcoma, seminomas, skin cancers, stomach cancers, teratomas, testicular cancers, thyroid cancers, uterine cancers, vaginal cancers, vascular tumors, and metastases thereof. In some embodiments, the cancer is a relapsed or refractory cancer. In some embodiments, the cancer is resistant to one or more cancer therapies, e.g., one or more chemotherapeutic drugs.

The presently disclosed subject matter also provides methods of increasing or lengthening survival of a subject having a neoplasia (e.g., a tumor). In one non-limiting example, the method of increasing or lengthening survival of a subject having neoplasia (e.g., a tumor) comprises administering an effective amount of the presently disclosed engineered immune cell to the subject, thereby increasing or lengthening survival of the subject. The presently disclosed subject matter further provides methods for treating or preventing a neoplasia (e.g., a tumor) in a subject, comprising administering the presently disclosed engineered immune cells to the subject.

Cancers whose growth can be inhibited using the engineered immune cells of the presently disclosed subject matter comprise cancers typically responsive to immunotherapy. Non-limiting examples of cancers for treatment include multiple myeloma, neuroblastoma, glioma, acute myeloid leukemia, colon cancer, pancreatic cancer, thyroid cancer, small cell lung cancer, and NK cell lymphoma. In certain embodiments, the cancer is multiple myeloma.

Additionally, the presently disclosed subject matter provides methods of increasing immune-activating cytokine production in response to a cancer cell or virally infected cell in a subject. In one non-limiting example, the method comprises administering the presently disclosed engineered immune cell to the subject. The immune-activating cytokine can be granulocyte macrophage colony stimulating factor (GM-CSF), IFNα, IFN-β, IFN-γ, TNF-a, IL-2, IL-3, IL-6, IL-11, IL-7, IL-12, IL-15, IL-21, interferon regulatory factor 7 (IRF7), and combinations thereof.

Suitable human subjects for therapy typically comprise two treatment groups that can be distinguished by clinical criteria. Subjects with "advanced disease" or "high tumor burden" are those who bear a clinically measurable tumor (e.g., multiple myeloma). A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in the presently disclosed subject matter is administered to these subjects to elicit an anti-tumor response, with the objective of palliating their condition. Ideally, reduction in tumor mass occurs as a result, but any clinical improvement constitutes a benefit. Clinical improvement comprises decreased risk or rate of progression or reduction in pathological consequences of the tumor (e.g., multiple myeloma).

A second group of suitable subjects is known in the art as the "adjuvant group." These are individuals who have had a history of neoplasia (e.g., multiple myeloma), but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor (e.g., multiple myeloma) has invaded neighboring tissues, or who show involvement of lymph nodes. Another group has a genetic predisposition to neoplasia (e.g., multiple myeloma) but has not yet evidenced clinical signs of neoplasia (e.g., multiple myeloma). For instance, women testing positive for a genetic mutation associated with breast cancer, but still of childbearing age, can wish to receive one or more of the compositions described herein in treatment prophylactically to prevent the occurrence of neoplasia until it is suitable to perform preventive surgery.

The subjects can have an advanced form of disease (e.g., multiple myeloma), in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Further modification can be introduced to the miR200c and/or EpCAM over-expressing engineered immune cells (e.g., T cells) to avert or minimize the risks of immunological complications (known as "malignant T-cell transformation"), e.g., graft versus-host disease (GvHD), or when healthy tissues express the same target antigens as the tumor cells, leading to outcomes similar to GvHD. Modification of the engineered immune cells can include engineering a suicide gene into the miR200c and/or EpCAM over-expressing T cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T cell elimination by administering anti-EGFR monoclonal antibody (e.g., cetuximab). The suicide gene can be included within the vector comprising nucleic acids encoding miR200c and/or EpCAM. A presently disclosed engineered immune cell (e.g., a T cell) incorporated with a suicide gene can be pre-emptively eliminated at a given time point post T cell infusion, or eradicated at the earliest signs of toxicity.

Combination Therapy

The compositions of the present technology may be employed in conjunction with other therapeutic agents useful in the treatment of cancers. For example, the miR200c and/or EpCAM over-expressing engineered immune cells of the present technology may be separately, sequentially or simultaneously administered with at least one additional therapeutic agent. Examples of additional therapeutic agents include, but are not limited to, antiangiogenic agents, alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents and targeted biological therapy agents (e.g., therapeutic peptides described in US 6306832, WO 2012007137, WO 2005000889, WO 2010096603 etc.). In some embodiments, the at least one additional therapeutic agent is a chemotherapeutic agent. Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), bevacizumab, oxaliplatin, melphalan, etoposide, mechlorethamine, bleomycin, microtubule poisons, annonaceous acetogenins, or combinations thereof.

Other examples of additional therapeutic agents include, but are not limited to, immune checkpoint inhibitors, monoclonal antibodies that specifically target tumor antigens, cell-mediated immunotherapy (e.g., T cell therapy), immune activating agents (e.g., interferons, interleukins, cytokines), oncolytic virus therapy and cancer vaccines. Examples of immune checkpoint inhibitors include immuno-modulating/stimulating antibodies such as an anti-PD-1 antibody, an anti-PD-L1 antibody, an anti-PD-L2 antibody, an anti-CTLA-4 antibody, an anti-TIM3 antibody, an anti-4-1BB antibody, an anti-CD73 antibody, an anti-GITR antibody, and an anti-LAG-3 antibody. Specific immuno-modulating/stimulating antibodies include ipilimumab, Nivolumab, Pembrolizumab, Atezolizumab, Avelumab, and Durvalumab. Additionally or alternatively, in some embodiments, the monoclonal antibodies that specifically target tumor antigens bind to one or more targets selected from among CD3, GPA33, HER2/neu, GD2, MUC16, MAGE-1, MAGE-3, BAGE, GAGE-1, GAGE-2, MUM-1, CDK4, N-acetylglucosaminyltransferase, p15, gp75, beta-catenin, ErbB2, cancer antigen 125 (CA-125), carcinoembryonic antigen (CEA), RAGE, MART (melanoma antigen), MUC-1, MUC-2, MUC-3, MUC-4, MUC-5ac, MUC-16, MUC-17, tyrosinase, Pmel 17 (gp100), GnT-V intron V sequence (N-acetylglucoaminyltransferase V intron V sequence), Prostate cancer psm, PRAME (melanoma antigen), β-catenin, EBNA (Epstein-Barr Virus nuclear antigen) 1-6, LMP2, p53, lung resistance protein (LRP), Bcl-2, prostate specific antigen (PSA), Ki-67, CEACAM6, colon-specific antigen-p (CSAp), HLA-DR, CD40, CD74, CD138, EGFR, EGP-1, EGP-2, VEGF, P1GF, insulin-like growth factor (ILGF), tenascin, platelet-derived growth factor, IL-6, CD20, CD19, PSMA, CD33, CD123, MET, DLL4, Ang-2, HER3, IGF-1R, CD30, TAG-72, SPEAP, CD45, L1-CAM, Lewis Y (Le$^y$) antigen, E-cadherin, V-cadherin, GPC3, EpCAM, DLL3, PD-1, PD-L1, CD28, CD137, CD99, GloboH, CD24, STEAP1, B7H3, Polysialic Acid, OX40, OX40-ligand, or other peptide MHC complexes (e.g., with peptides derived from TP53, KRAS, MYC, EBNA1-6, PRAME, MART, tyronsinase, MAGEA1-A6, pmel17, LMP2, or WT1). Examples of immune activating agents include, but are not limited to, interferon α, interferon β, interferon γ, complement C5a, IL-2, TNFalpha, CD40L, IL12, IL-23, IL15, IL17, CCL1, CCL11, CCL12, CCL13, CCL14-1, CCL14-2, CCL14-3, CCL15-1, CCL15-2, CCL16, CCL17, CCL18, CCL19, CCL19, CCL2, CCL20, CCL21, CCL22, CCL23-1, CCL23-2, CCL24, CCL25-1, CCL25-2, CCL26, CCL27, CCL28, CCL3, CCL3L1, CCL4, CCL4L1, CCL5, CCL6, CCL7, CCL8, CCL9, CCR10, CCR2, CCR5, CCR6, CCR7, CCR8, CCRL1, CCRL2, CX3CL1, CX3CR, CXCL1, CXCL10, CXCL11, CXCL12, CXCL13, CXCL14, CXCL15, CXCL16, CXCL2, CXCL3, CXCL4, CXCL5, CXCL6, CXCL7, CXCL8, CXCL9, CXCL9, CXCR1, CXCR2, CXCR4, CXCR5, CXCR6, CXCR7 and XCL2.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

Articles of Manufacture and Kits

The presently disclosed subject matter provides kits for the treatment or prevention of a disease, such as neoplasia (e.g., solid tumor). In certain embodiments, the kit comprises a therapeutic or prophylactic composition containing an effective amount of an engineered immune cell comprising a vector that overexpresses miR200c and/or EpCAM. In some embodiments, the engineered immune cell is a CAR, caTCR, or eTCR. In particular embodiments, the engineered immune cell further expresses at least one co-stimulatory ligand.

If desired, the engineered immune cell can be provided together with instructions for administering the engineered immune cell to a subject having or at risk of developing a neoplasia (e.g., solid tumor). The instructions will generally include information about the use of the composition for the treatment or prevention of a neoplasia (e.g., solid tumor). In other embodiments, the instructions include at least one of the following: description of the therapeutic agent; dosage schedule and administration for treatment or prevention of a neoplasia (e.g., solid tumor) or symptoms thereof; precautions; warnings; indications; counter-indications; overdose information; adverse reactions; animal pharmacology; clinical studies; and/or references. The instructions can be printed directly on the container (when present), or as a label applied to the container, or as a separate sheet, pamphlet, card, or folder supplied in or with the container.

Also provided herein are kits for use in the manufacture of an engineered immune cell that overexpresses miR200c and/or EpCAM. In certain embodiments, the kit comprises a vector encoding miR200c and/or EpCAM. Additionally or alternatively, in some embodiments, the kit further comprises a vector encoding an engineered T-cell receptor (TCR) or other cell-surface ligand that binds to a target antigen, such as a tumor antigen or viral protein.

In some embodiments, the kits provided herein comprise a sterile container, such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In some embodiments, the sterile container contains a therapeutic or prophylactic vaccine.

EXAMPLES

Example 1: Materials and Methods

Mice

The animal and protocols used for this study were approved by the Institutional Animal Care and Use Committee of Memorial Sloan Kettering Cancer Center. C57BL/6J mice, CD45.1$^+$ congenic mice (B6.SJL-Ptprc$^a$Pepc$^b$/Boy), OT1 TCR transgenic mice, Rosa26-Cas9 knockin mice, and NSG mice (NOD.Cg-Prkdc$^{scid}$Il2rg$^{tm Wjl}$/SzJ) were obtained from Jackson Laboratory, Bar Harbor, ME. Pmel TCR transgenic mice and Ahr$^{-/-}$ mice were obtained from Dr. Jedd Wolchok (MSKCC) and Dr. Jayanta Chaudhuri (MSKCC), respectively. Ahr$^{-/-}$ mice were crossed with OT1 mice to generate Ahr$^{-/-}$ OT1 and Ahr$^{+/-}$ OT1 mice. OT1 mice and Rosa26-Cas9 knockin mice were crossed to generate OT1 Cas9 mice for in vitro CRISPR/Cas9.

Cells

Primary OT1 CTLs were cultured by mixing of T cells from TCR OT1 transgenic mice at 37° C. with feeder cells (irradiated splenocytes from C57BL/6J mice) and 100 nM OVA (SIINFEKL (SEQ ID NO: 1), GenScript, Piscataway, NJ) in complete RPMI medium (RPMI1640 supplemented with 10% (vol/vol) FCS, 10 mM HEPES (Invitrogen, Carlsbad, CA), 2 mM L-glutamine (Invitrogen, Carlsbad, CA), 1× non-essential amino acids (Invitrogen, Carlsbad, CA), 1 mM sodium pyruvate (Invitrogen, Carlsbad, CA) and 50 μM 2-mercaptoethanol (Sigma-Aldrich, St. Louis, MO)). 30 IU/ml IL-2 was added to the medium after 24 hours and the cells split into complete RPMI plus 30 IU/ml IL-2 as necessary for the next 6 days. Pmel CTLs were generated using the same protocol except that 100 nM gp100 peptide (EGSRNQDWL (SEQ ID NO: 2), GenScript, Piscataway, NJ) was applied instead of OVA. B16F10 cells and MO4 cells (B16F10 cells expressing ovalbumin protein) were grown in RPMI containing 10% (vol/vol) FCS. EL4 and NALM6 cells were cultured in complete RPMI. NALM6 cells were transduced with firefly luciferase-GFP as described (Zhao, Z., et al., Cancer Cell, 28: 415-428 (2015)). Phoenix E cells were grown in DMEM containing 10% (vol/vol) FCS. Human T cells were purified from blood samples obtained from healthy volunteers under an institutional review board approved protocol. PBMC were isolated by density gradient centrifugation over Ficoll (CORNING, Corning, NY), washed in phosphate buffered saline (PBS), and resuspended in complete RPMI. To selectively expand T cells, 2 µg/ml PHA (Invitrogen, Carlsbad, CA) was added to the PBMCs and, 24 hours later, the culture medium was supplemented with 5 ng/ml rhIL7 and 5 ng/ml rhIL-15 (both from Peprotech, Rocky Hill, New Jersey).

Constructs

The retroviral miR library has been described by Mavrakis, K. J., et al., *Nat Genet* 43: 673-678 (2011). To express miR200c, miR16, and miRScr individually, stem-loop sequences from miRBase (http://www.mirbase.org/) were subcloned into the LEPG retroviral expression vector as described by Fellmann, C., et al., *Cell Rep* 5, 1704-1713 (2013) using either the EcoRI and XhoI sites. gRNAs constructs targeting Zeb 1 and EpCAM were generated in a two-step manner. First, gRNAs were assembled in the LentiGuide-Puro vector using the following oligos: Zeb 1 gRNA #1, sense oligo 5'-caccgACCTGCCCGTATTGTGATAG-3' (SEQ ID NO: 3); antisense oligo 5'-AAACCTATCACAATACGGGCAGGTC-3' (SEQ ID NO: 4); Zeb 1 gRNA #4, sense oligo 5'-caccgGTACCGCCATGAGAAGAACG-3' (SEQ ID NO: 5); antisense oligo 5'-AAACCGTTCTTCTCATGGCGGTACC-3' (SEQ ID NO: 6); Zeb1 gRNA #6 sense oligo 5'-caccgGGGGCGGTGCCAAGAACTGC-3' (SEQ ID NO: 7); antisense oligo 5'-AAACGCAGTTCTTGGCACCGCCCCC-3' (SEQ ID NO: 8); EpCAM gRNA sense oligo 5'-caccgGAATGCCAGTGTACTTCCTA-3' (SEQ ID NO: 9); antisense oligo 5'-AAACTAGGAAGTACACTGGCATTCC-3' (SEQ ID NO: 10); Non-targeting gRNA sense oligo 5'-caccgACGTGGGGACATATACGTGT-3' (SEQ ID NO: 11); antisense oligo 5'-AAACACACGTATATGTCCCCACGTC-3' (SEQ ID NO: 12). Then, the gRNA coding sequence, together with the upstream U6 promoter, was PCR amplified with the following oligos: LMP BamHI F2 5'-TTTTTGGATCCTAGTAGGAGGCTTGGTAG-3' (SEQ ID NO: 13) and LMP EcoRI R2 5'-TTTTTGAATTCTGTCTACTATTCTTTCCC-3' (SEQ ID NO: 14). The resulting fragments were digested with BamHI and EcoRI and ligated into the LEPG retroviral expression vector previously digested with EcoRI and BglII. For combined expression of miR200c and gRNA against EpCAM, the Gibson method was used to subclone U6-gRNA fragment into the LEPG-miR200c vector downstream of the GFP gene. For retroviral expression of EpCAM protein, the full length coding sequence of mouse EpCAM was subcloned into a pMSCV based retroviral vector upstream and in frame with GFP as described by Quann, E. J., et al., *Nat Immunol* 10, 627-635 (2009). The following primers were used: EpCAM-GFP, Forward-1 5'-TACAATACTCGAGATGGCGGGTCCCCAGGCCCTC-3' (SEQ ID NO: 15) and Reverse-1 5'-ATAGTTTAGCGGCCGCGGCATTAAGCTCTCTGTGGA-3' (SEQ ID NO: 16); For retroviral expression of AhR, the full length coding sequence of mouse AhR was subcloned into pMSCV-PIG (gift from Scott Lowe, Addgene #18751) using the Gibson method. The following primers were used: forward 5'-AGGCGCCGGAATTAGATCTCATGAGCAGCGGCGCCAACATC-3' (SEQ ID NO: 17), and reverse 5'-CGCCTCCCCTACCCGGTAGTCAACTCTGCACCTTGCTTAG-3' (SEQ ID NO: 18). miR sponge constructs were designed and tested as described by Kluiver, J., et al., *PloS One* 7: e29275 (2012). Multiple high affinity miRNA antisense binding sites (MBS) targeting miR200c and miRScr were generated using the following oligos:

```
miR200c_Sense:
                                        (SEQ ID NO: 19)
5'-GTCCCTCCATCATTATTAGCAGTATTAAATTTCCATCATTATTAGC
AGTATTAG-3';

miR200c_Antisense:
                                        (SEQ ID NO: 20)
5'-GACCCTAATACTGCTAATAATGATGGAAATTTAATACTGCTAATAA
TGATGGAGG-3';

miR_scramble_sense:
                                        (SEQ ID NO: 21)
5'-GTCCCCTACCTGCACTCCGATGCTCTGTTATCTACCTGCACTCCGA
TGCTCTGGG-3';

miR_scramble_Antisense:
                                        (SEQ ID NO: 22)
5'-GACCCCAGAGCATCGGAGTGCAGGTAGATAACAGAGCATCGGAGTG
CAGGTAGG-3'.
```

For retroviral expression in T cells, MBS sequences were subcloned into pMSCV PIG as even multiples. CD19CAR experiments utilized an SFG vector encoding anti-CD19-1928z-CAR and CD271 separated by a P2A sequence as described by Zhao, Z., et al., *Cancer Cell* 28: 415-428 (2015). For combined expression of human CD19CAR and EpCAM, the Gibson method was used to replace the CD271 gene with the full-length coding sequence of EpCAM. For retroviral expression of GD2CAR in mouse T cells, an SFG retroviral plasmid containing the murine anti-CD19-1928z CAR fused to GFP was modified by the Gibson method so that the anti-CD19 scFv portion of the CAR was replaced with an scFv derived from the GD2 specific hu3F8 antibody as described by Cheung, N. K., et al., Cancer Res 45: 2642-2649 (1985). For combined expression of GD2CAR and mouse EpCAM, the linker-GFP portion of the GD2CAR fusion construct was replaced, by Gibson cloning, with the P2A and EpCAM coding sequences. The newly assembled GD2CAR-P2A-EpCAM cassette was PCR amplified and transferred into the pMSCV-PIG plasmid. For combined expression of GD2CAR and miR200c, Gibson cloning was used to insert miR200c, under the control of a U6 promoter, into pMSCV-PIG downstream of the GFP cassette. The GD2CAR coding sequence was then inserted into the standard multicloning site.

Retroviral Transduction

For transduction of OT1 and Pmel 1 T cells, Phoenix E cells were transfected with expression vectors together with packaging plasmids (pCL-Eco) using the calcium phosphate method. Viral supernatants and polybrene (4 µg/ml) were added to OT1 or Pmel1 T cell blasts 2 days after primary peptide stimulation in 6-well plates. The plates were centrifuged at 1400×g at 35° C. for 2 hours. T cells were then split 1:3 in complete RPMI containing 30 IU/ml IL-2. To generate virus for transduction of human T cells, viral vectors were stably transfected into gpg29 fibroblasts (H29) as described by Gong, M. C., et al., *Neoplasia* 1: 123-127 (1999). Human T cells were activated with PHA for 48 hours and then transduced with retroviral supernatants by centrifugation on retronectin (Takara, Kusatsu, Shiga, Japan)-coated plates. Cells were used for validation and ACT experiments 7 days after PHA activation.

Sponge Validation miR sponge sequences were cloned into the 3' UTR of the Firefly luc2 gene in the pGL4.1 vector (Promega, Madison, WI). 293T cells stably transduced with miR200c or miRScr were transiently transfected (using PEI MAX, Polysciences, esm Inc., Warrington, PA) with the luc2-miR sponge construct and a control vector expressing Renilla luciferase. 24 hours later, lysates were prepared and assessed for both Firefly and Renilla luciferase activity using the Dual Luciferase Reporter Kit (Promega, Madison, WI). The luciferase activity was standardized by Firefly/Renilla.

Tumor Models

OT1-B16OVA: $2 \times 10^5$ B16OVA cells were injected into C57BL/6J mice and allowed to grow for 6 days. Then, tumor-bearing mice were subjected to sublethal irradiation (600cGy) using an animal Cesium irradiator (Gammacell) to facilitate T cell engraftment. The following day, $10^5$ OT1 CTLs were injected i.v., after which tumor size was measured by metric caliper every 2-3 days for up to 4 weeks. CD45.1$^+$ congenic mice were as recipients in certain experiments to facilitate identification of OT1 CTLs in tumors and other organs. In certain experiments, 200 µg/ml anti-PD1 antibody (clone RMP1-14) or isotype control antibody were injected intraperitoneally into recipient mice on the day of CTL injection and twice a week thereafter for the duration of the experiment.

Pmel 1-B16: $5 \times 10^5$ B16 cells were injected into C57BL/6J mice and allowed to grow for 6 days. Then, tumor-bearing mice were subjected to sublethal irradiation (600cGy) using an animal Cesium irradiator (Gammacell) to facilitate T cell engraftment. The following day, $5 \times 10^5$ Pmel 1 CTLs were injected i.v., after which tumor size was measured by metric caliper every 2-3 days for up to 4 weeks.

GD2CAR-EL4: Because EL4 cells are particularly radiation sensitive, C57BL/6J recipient mice were sublethally irradiated (600cGy) one day before s.c. injection of $5 \times 10^5$ EL4 cells. Tumors were allowed to grow for 1 week, and the $5 \times 10^5$ GD2CAR CTLs were injected i.v. Tumor size was measured by metric caliper every 3 days for up to 4 weeks.

CD19CAR-NALM6: 7-8 week old NSG mice were injected i.v. with $5 \times 10^5$ FFLuc-GFP-NALM6 cells, followed by i.v. injection of $1 \times 10^5$ CAR T cells four days later. Animal bioluminescence imaging was performed weekly in the MSKCC Animal Imaging Core Facility. Data were processed and analyzed using the Xenogen IVIS Imaging System with Living Image software (Xenogen, Alameda, CA). Tumor burden was assessed as previously described by Zhao, Z., et al., *Cancer Cell* 28: 415-428 (2015).

Cell Extraction from Mouse Tissue

Prior to organ collection, mice were perfused with 10 ml PBS with 2 mM EDTA. Spleens were crushed over 70 µm strainers, and isolated cell suspensions were cleared of red blood cells using ammonium-chloride-potassium (ACK) lysing buffer. B16 tumor tissues were mechanically dissociated using metal mesh and filtered through a 70 µm strainer. The resulting cells were resuspended in 15 ml Hanks buffered saline solution (HB SS, without Mg$^{2+}$/Ca$^{2+}$) with 3% FCS. After adding 20 U/ml heparin and 8 ml 100% Percoll (Sigma-Aldrich, St. Louis, MO), samples were centrifuged at 600×g for 10 minutes at 4° C. The pellet was treated with ACK buffer and washed into HBSS. Liver, kidney, and lungs were dissociated with scissors and digested with Collagenase D (1 mg/ml; MilliporeSigma, Burlington, MA) in HBSS (with Mg$^{2+}$/Ca$^{2+}$) for 20 minutes at 37° C. Samples were then mechanically disrupted, filtered through a 70 µm strainer, and resuspended in 15 ml cold HBSS (without Mg$^{2+}$/Ca$^{2+}$) with 3% FCS. After adding 20 U/ml heparin and 8 ml 100% Percoll, samples were centrifuged at 600×g for 10 minutes at 4° C. Cell pellets were resuspended in 10 ml HBSS (without Mg$^{2+}$/Ca$^{2+}$) with 3% FCS, and placed over 60% Percoll carefully. After additional centrifugation at 600×g for 10 minutes at 4° C., the middle band of cells was collected, washed in HBSS, and maintained in HB SS (without Mg$^{2+}$/Ca$^{2+}$) with 3% FCS prior to use. For bone marrow cell isolation, leg bones were grinded and the resulting sample filtered through a 70 µm strainer. Red blood cells in pellets were cleared using ACK buffer, and the remaining cells washed into HBSS (without Mg$^{2+}$/Ca$^{2+}$) with 3% FCS.

In Vitro Killing, Degranulation, and Conjugate Formation

EL4 target cells were labeled with CellTrace Violet (CTV), loaded with increasing amounts of OVA peptide and mixed 1:1 with transduced OT1 CTLs (GFP$^+$) in a 96-well V-bottomed plates. To assess killing specific lysis of CTV+ target cells was determined by flow cytometry after 4-5 h incubation at 37° C., as described by Purbhoo, M. A., et al., *Nat Immunol* 5: 524-530 (2004). To assess degranulation, 2 µg/ml fluorescently conjugated anti-Lamp1 antibody was included in the CTL-EL4 cocultures and after 2 hours at 37° C., Lamp1 staining was quantified by flow cytometry. To assess conjugation, CTV-stained, OVA-loaded EL4 cells were suspended in Hanks' balanced salt solution (HBSS) with 5% FBS and mixed 1:1 with GFP$^+$ transduced OT1 CTLs. Cells were centrifuged at 20×g for 3 minutes, incubated at 37° C. for 20 minutes, fixed with 4% paraformaldehyde (PFA), and then analyzed by flow cytometry. % conjugation was calculated as (CTV$^+$GFP$^+$)/GFP$^+$. For B16OVA killing, B16OVA cells were seeded $10^5$ per well in 24-well plates and after 24 hours, OT1 CTLs were added at various E:T ratios to each well. After 5 h incubation at 37° C., cell death was quantified by LDH (lactate dehydrogenase) release using an LDH quantification kit (Clontech). Cytotoxicity, degranulation, and conjugate formation assays were performed in triplicate.

In Vitro Proliferation and Survival

To quantify TCR-induced proliferation, OT1 CTLs were labeled with CTV (Invitrogen, Carlsbad, CA) and mixed with OVA-loaded, irradiated C57BL/6 splenocytes. CTV dilution was assessed on a daily basis by flow cytometry. To measured survival, OT1 CTLs (7 days after initial peptide stimulation) were transferred into complete RPMI lacking IL-2 at $1 \times 10^5$ cells/ml. Survival was measured by DAPI (Fisher, Hampton, NH) exclusion after 24 or 48 h. To quantify apoptosis, samples were incubated in 500 nM CellEvent™ Caspase 3/7 detection reagent (Thermofisher), together with antibodies for cell surface markers, for 30 min at 37° C., followed by flow cytometry. For in vitro cell death assays, CTLs were either cultured in standard complete RPMI with 30 IU/ml IL2 for 48 h or transferred to complete RPMI with 5 ng/ml IL7 and cultured for 48 h. Treatment with 2 µM staurosporine or 2 ng/ml FasL was carried out in complete RPMI with 30 IU/ml IL2. Staurosporine- and FasL-induced Caspase 3/7 activation was evaluated after 4 h and 48 h, respectively.

Flow Cytometric Analysis of Transcription Factors and Cytokines

Cell suspensions were first stained for surface markers (e.g. CD45.2 and CD8) and then fixed and stained for TCF1 (clone C63C9), T-bet (clone 4B10), Eomes (clone Dan11mag), Blimp1 (clone 5E7), and Ki67 (clone B56) using the Foxp3/Transcription Factor Staining Buffer Kit (Tonbo Biosciences, San Diego, CA) according to manufacturer instructions. To assess IFNγ and TNF production, live cell suspensions were stimulated by plate bound anti-CD3ε (1 µg/ml coating concentration; 145-2C11; BioXCell) and anti-CD28 (1 µg/ml coating concentration; 37.51; BioX-Cell) or PMA/Ionomycin (20 ng/ml and 1 µg/ml, respectively) for 2 hours in 37° C., after which GolgiPlug™ was added and the cells incubated for an additional 4 hours in 37° C. After staining for surface markers, samples were fixed with IC Fixation Buffer (eBioscience, San Diego, CA), treated with permeabilization buffer (eBioscience, San Diego, CA), and stained with fluorescently labeled anti-IFNγ (clone XMG1.2) and anti-TNF (clone MP6-XT22) antibodies, followed by flow cytometric analysis.

Trogocytosis Assay

To measure trogocytosis (e.g. FIG. 1C) EL4 target cells were stained with CellVue Maroon (eBioscience, San Diego, CA), loaded with various doses of OVA for 45 minutes at 37° C., and then mixed 1:1 with OT1 CTLs. After 1-2 hours at 37° C., CellVue Maroon transfer to CTLs was quantified by flow cytometry. For miR library screening (FIG. 1A), EL4 cells were stained separately with CellVue Maroon, PKH26 (Sigma-Aldrich, St. Louis, MO), or EZ-Link Silfo-NHS-LC-Biotin (Fisher Scientific, Waltham, MA), and then loaded with 100 nM OVA (no OVA as negative control to set gate). An equal mixture of CellVue Maroon⁺, PKH26⁺, and biotinylated EL4 cells were then mixed 1:1 with OT1 CTLs (GFP⁺) expressing 1 of 5 miR pools (60 miRs per pool). After a 1.5-2 hours incubation at 37° C., samples were stained with streptavidin-Pacific Blue (to label biotinylated material) and FACS sorted. Total GFP⁺ cells, GFP⁺ CellVue Maroon⁺ PKH26⁺ Pacific Blue⁺ (trogocytosis⁺) cells, and GFP⁺ CellVue Maroon⁻ PKH26⁻ Pacific Blue⁻ (trogocytosis⁻) cells were isolated and subjected to DNA extraction using the Genomic DNA Purification Kit (Promega, Madison, WI). The miR expression cassettes (200-300 bp each) were then PCR-amplified using oligos Forward: ACCGGTAGGCCTCGTACGCTTA (SEQ ID NO: 23) and Reverse: TCCACAGGGTCGACCACTG (SEQ ID NO: 24), followed by lumina Next Generation Sequencing analysis (MiSeq PE300) at the Integrated Genomics Operation (IGO) at MSKCC. miRNA reads were identified by adapter sequences using a fuzzy match that allowed up to 2 mismatches. In a typical deep sequencing run, 26-28% of the read counts corresponded to miRs. Only miRs with read counts≥50 were considered as potential candidates. miRs associated with trogocytosis$^{hi}$ and trogocytosis$^{lo}$ populations were identified using the enrichment ratio (counts in trogocytosis$^{hi}$)/(counts in trogocytosis$^{lo}$). 11 trogocytosis$^{hi}$ and 5 trogocytosis$^{lo}$ candidates were analyzed in a secondary cytotoxicity screen using antigen-loaded EL4 cells as targets. Subsequently, miR200c and miR16 were subjected to more in depth analysis.

Histology

B16OVA tumors were cleared of excess liquid and embedded in O.C.T Compound (Fisher Healthcare, Waltham, MA) on dry ice. 10 µm sections were cut using a Cryostat (Leica CM1900) and adsorbed onto glass. After drying, tissue was fixed in 4% PFA for 15 minutes, washed in PBS containing 0.1% Tween20 (Fisher Scientific, Waltham, MA) for 10 minutes, blocked with 5% Bovine serum albumin (BSA) in PBS, and stained with DAPI and antibodies against CD45.2 (clone 104.2) and CD31 (clone MEC13.3) for 2 h at 4° C. After washing, slides were sealed by ProLong Gold Antifade Mountant (Fisher Scientific, Waltham, MA), scanned on a Pannoramic Scanner device (3DHistech, Budapest, Hungary), and analyzed using Case-Viewer 2.2 software (3DHistech, Budapest, Hungary). CTL infiltration of tumors was quantified in ImageJ by counting the CD45+ cells in each section using the Analyze Particles function after gray-scaling and intensity thresholding.

Western Blot

Cell pellets were solubilized in lysis buffer (50 mM tris-HCl pH 7.5, 150 mM NaCl, 10 mM sodium pyrophosphate, 1 mM phenylmethylsulfonyl fluoride (PMSF), 1 mM sodium orthovanadate, 2 mM sodium fluoride, 0.5% Triton X-100, and protease inhibitor cocktail (Roche, Basel, Switzerland), nuclei were removed by centrifugation at 16,000×g for 10 minutes, and then samples were boiled in SDS sample buffer. To assess β-catenin expression, cells were boiled directly in SDS sample buffer and supernatants analyzed after centrifugation at 16,000×g for 10 minutes. Samples were resolved by SDS-PAGE, transferred to nitrocellulose membranes, and blocked with 5% BSA in PBS. After incubation with primary and fluorescently conjugated secondary antibodies, blots were imaged using an Odyssey Infrared Imaging System (LI-COR Biosciences, Lincoln, NE). The following primary antibodies were used: Bc12 (clone D17C4), Zeb1 (clone 3G6), AhR (clone FF3399), β-catenin (clone 14/Beta-Catenin), actin (clone AC-15).

RNA-seq Sample and Gene Enrichment Analysis

RNA from three biological replicate samples of miRScr and miR200c OT1 CTLs was extracted using TRIzol (Invitrogen, Carlsbad, CA) and stored at −80° C. for downstream RNA-seq analysis. RNA quality control and sequencing was performed at the MSKCC Integrated Genomics Operation (IGO) following the Illumina protocol (Illumina, San Diego, CA). RNA-seq reads were aligned to the mouse reference genome (GRCm38) using STAR and summarized as counts per gene or transcript. The counts were normalized by filtering lowly expressed genes and applying a log-transformation was applied to stabilize variance as described by McCarthy, D. J., et al., *Nucleic Acids Res* 40: 4288-4297 (2012) and by Love, M. I et al., *Genome Biol* 15: 550 (2014). After data normalization, differential gene expression was analyzed using the Limma pipeline as described by Ritchie, M. E., et al., *Nucleic Acids Res* 43: e47 (2015). GSEA analysis, as described by Subramanian, A., et al., *Proc Natl Acad Sci USA* 102: 15545-15550 (2005), was performed using minimum and maximum gene set sizes of 15 and 500, respectively, and 1000 permutations.

Statistical Analysis

Figures show representative experiments. Statistical analyses were carried out using either representative experiments or pooled data as indicated. Statistical tests for differential gene expression and GSEA were performed using Limma and GSEA software, respectively. All other statistical analyses were carried out using GraphPad Prism. Details for each type of statistical test (e.g. Student's t test, ANOVA, Log-rank) may be found in the figure legends. Unless otherwise stated, error bars denote SEM.

Example 2: A Functional Screen for miR Modulators of CTL Cytotoxicity

The present Example describes studies demonstrating that ectopic expression of microRNA-200c (miR200c) markedly enhanced the anti-tumor activity of CD8⁺ cytotoxic T lymphocytes (CTLs).

To identify strategies for improving anti-tumor ACT, an unbiased screen of miRs for genetic modifications that alter CTL functionality was performed. CTL-mediated killing is often accompanied by the exchange of cell surface material between the CTL and the target cell, a process known as trogocytosis. Trogocytosis, which scales with cytotoxic activity, was used as a proxy for identifying the most lethal CTLs in a population (FIG. 1A). Murine CTLs bearing the OT1 T cell receptor (TCR), which is specific for the ovalbumin$_{257-264}$ peptide presented by the class I MHC protein H2-K$^b$, were retrovirally transduced with one of five miR pools and then incubated with OVA-loaded EL4 target cells bearing one of three different membrane stains. After two hours, CTLs bearing fluorescent label from all three kinds of targets (the "best" killers) and CTLs that had not acquired any stain (the "worst" killers) were sorted and subjected to deep sequencing to identify miRs that were enriched in either the trogocytosis hi or the trogocytosis$^{lo}$ sub sets.

Figure 1B:
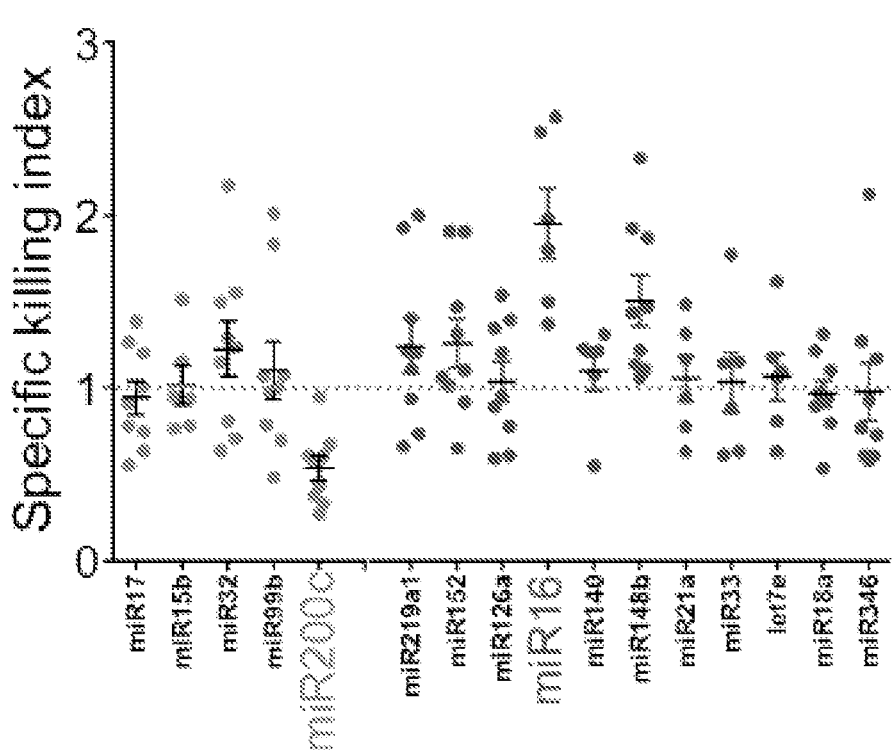
Figure 1C:
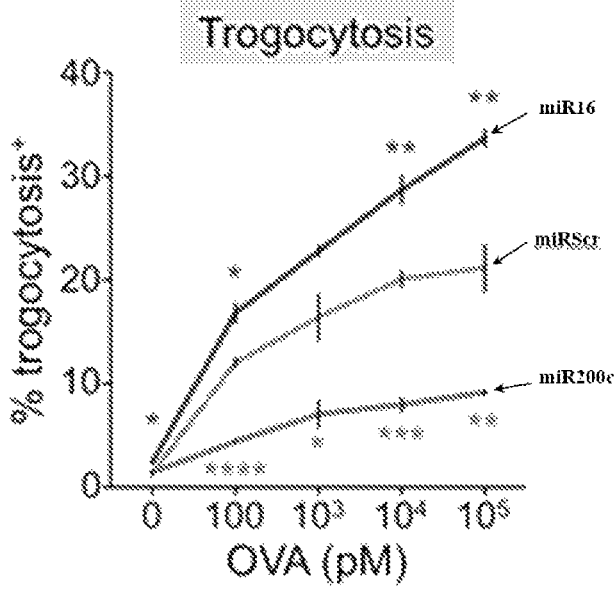
Figure 1D:
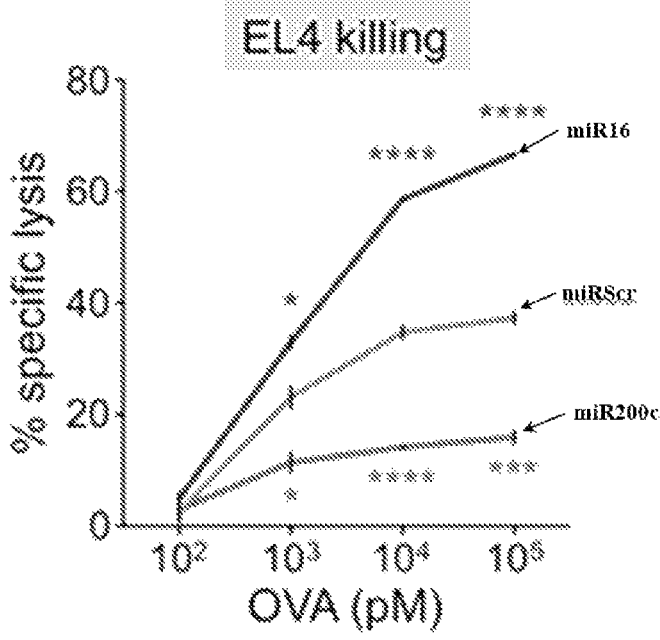
Figure 1E:
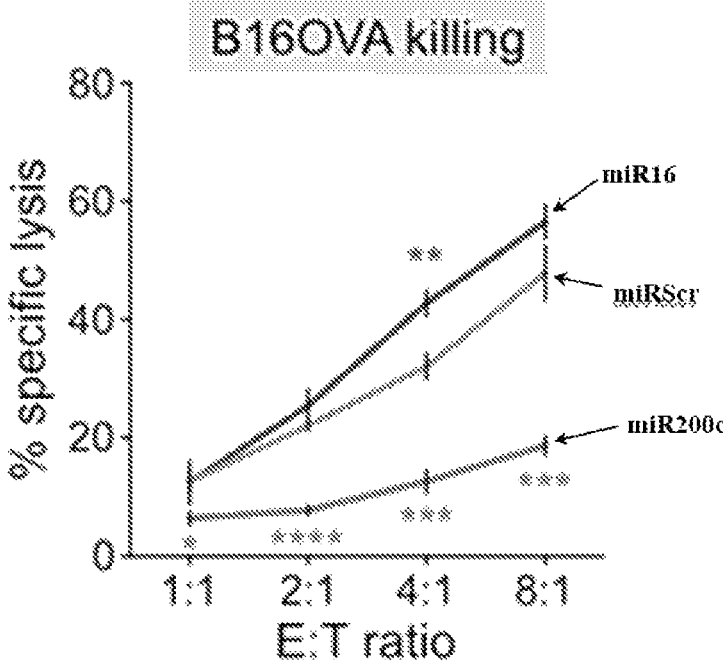
Figure 1F:
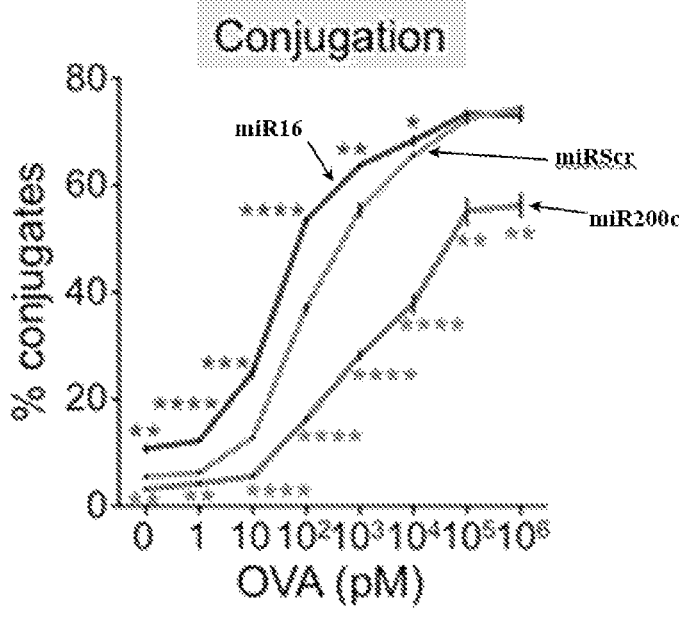
Figure 1G:
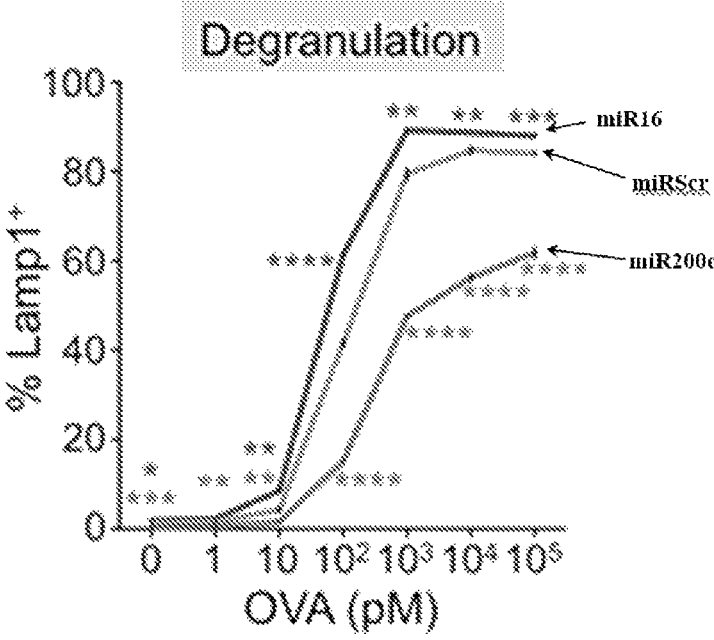

In this manner, miRs that reproducibly altered cytotoxic responses in vitro were identified. Two candidates, miR16 (trogocytosis$^{hi}$) and miR200c (trogocytosis$^{lo}$), were selected for further analysis (FIGS. 1B-1C). CTLs transduced with miR16 (miR16 CTLs) killed both adherent (B16 melanoma) and non-adherent (EL4 lymphoma) target cells more effectively than control CTLs expressing a scrambled miR (miRScr CTLs), while CTLs overexpressing miR200c (miR200c CTLs) exhibited reduced cytotoxicity in both assays (FIGS. 1D-1E). Two cell biological events associated with killing, i.e., the formation of CTL-target cell conjugates and the release of cytotoxic proteins, also called degranulation, were examined. Both responses were enhanced by miR16 and suppressed by miR200c (FIGS. 1F-1G), consistent with the observed cytotoxicity phenotypes.

Example 3: miR200c Enhances CTL Anti-tumor Activity In Vivo

Figure 2A:
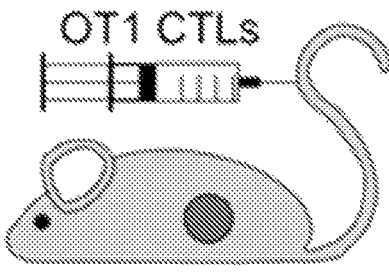
FIGS. 2A-2C show that miR200c enhances CTL persistence. Mice bearing subcutaneous (s.c.) B16OVA (FIG. 2A), B16 (FIG. 2B), or EL4 (FIG. 2C) tumors were injected with OT1 (FIG. 2A) or Pmel 1 (FIG. 2B) CTLs expressing the indicated miRs or OT1 CTLs expressing the indicated miRs together with GD2CAR (FIG. 2C). An additional group received vehicle control (PBS). Above, schematic diagrams of each model. Middle, mean tumor volume plotted against time. Below, Kaplan-Meier plots showing overall survival. n=5 for A, n=10 for B, n=10 for C.
Figure 2A:
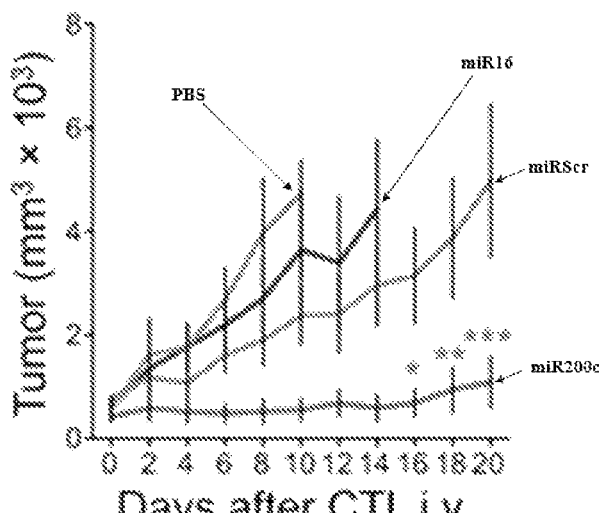
Figure 2A:
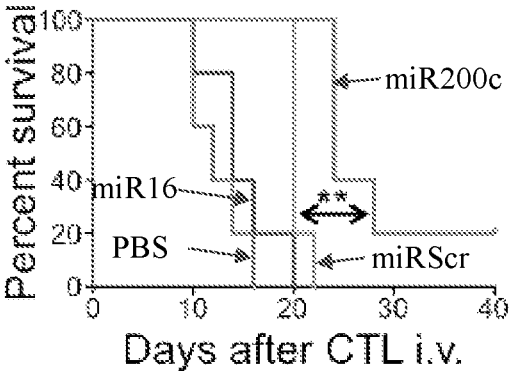
Figure 9A:
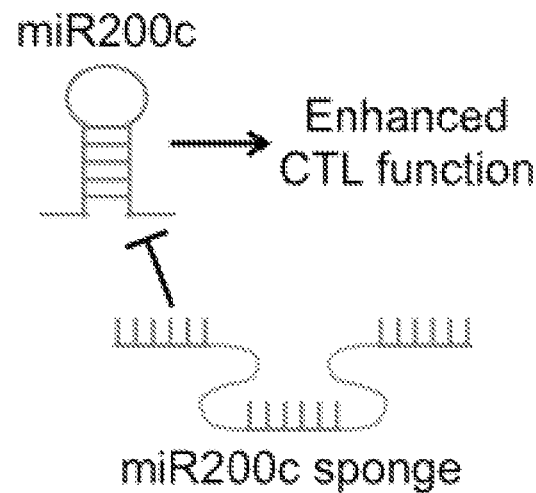
FIGS. 9A-9D show that a miR200c sponge reverses the miR200c CTL phenotype. Related to FIGS. 2A-2D.
Figure 9B:
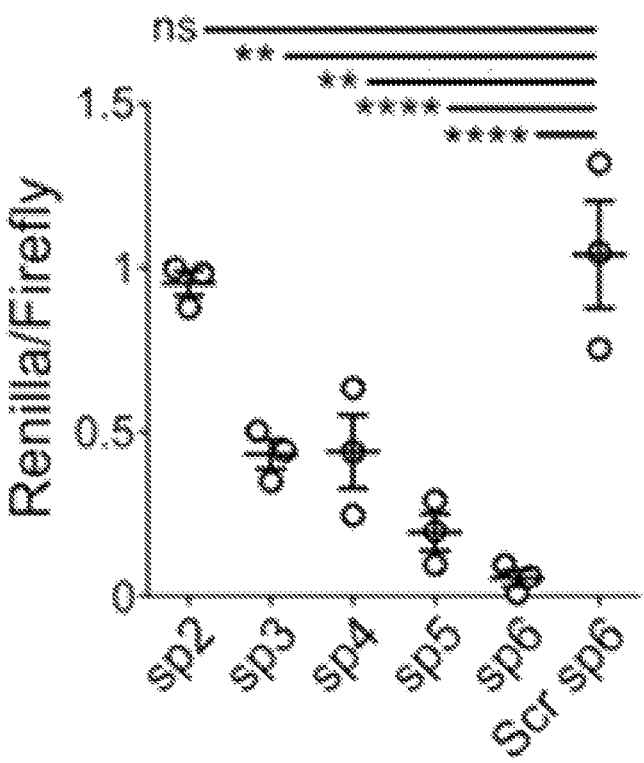
Figure 9C:
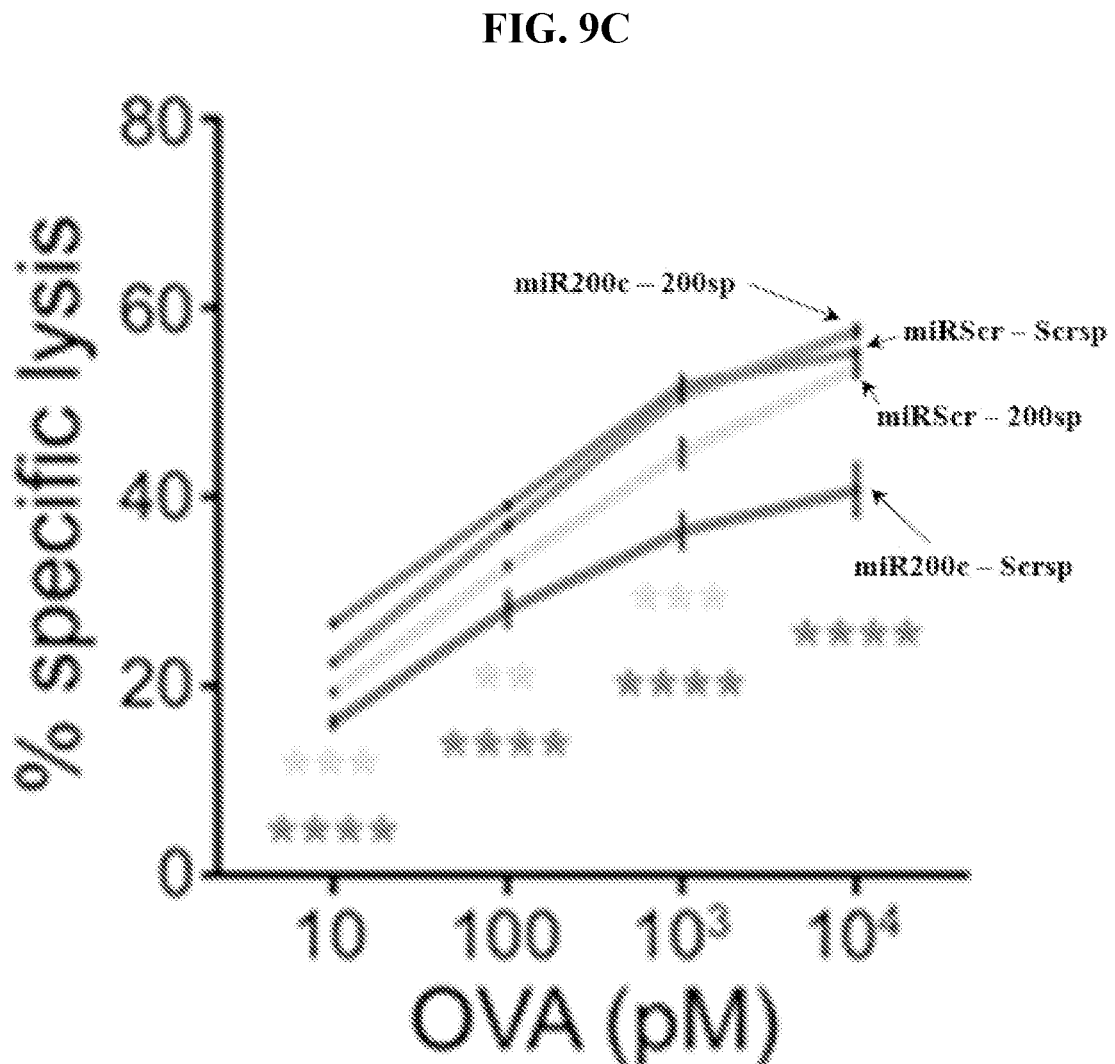
Figure 9D:
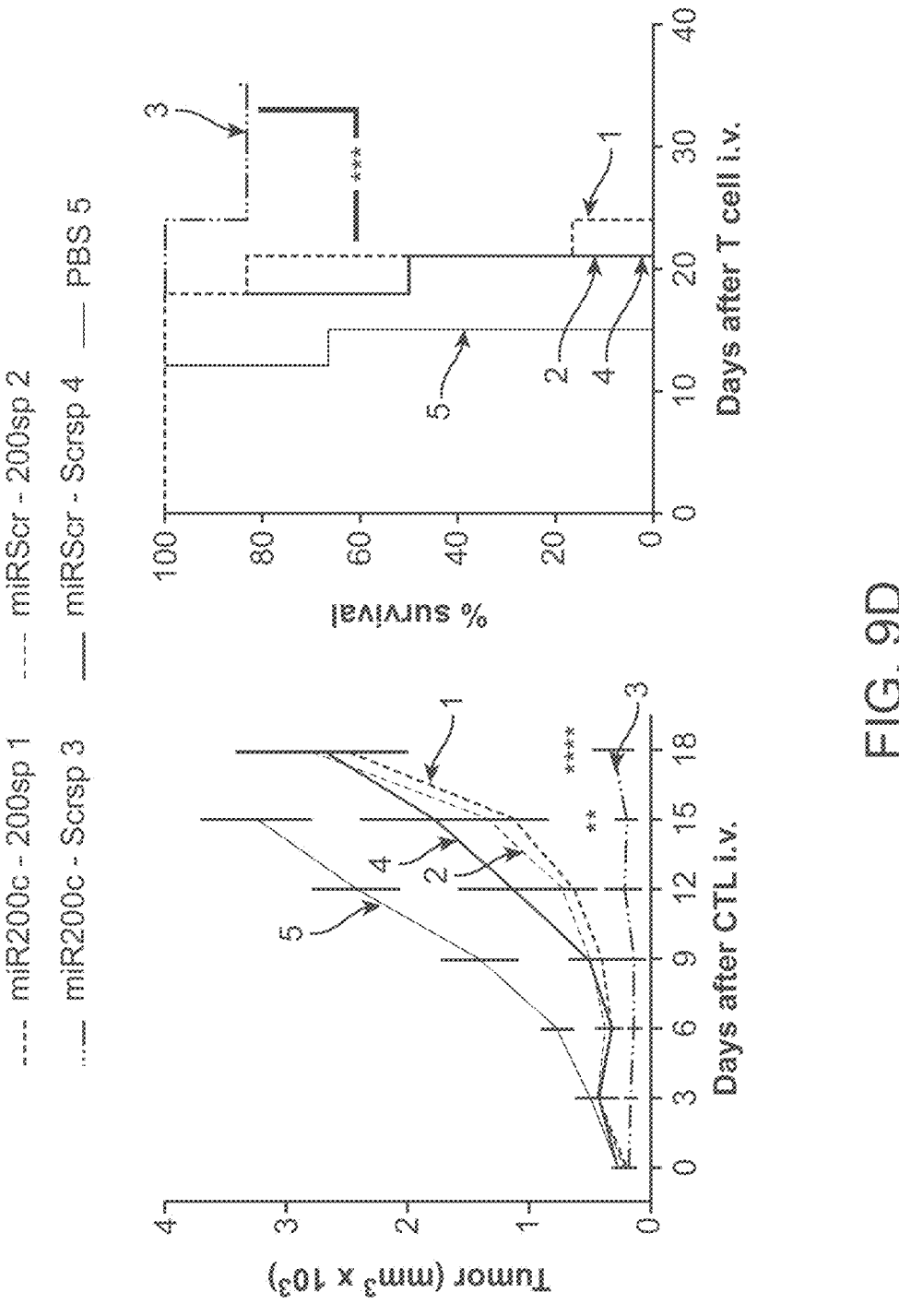

Next, an established ACT model was used to examine miR16 and miR200c's effects on CTLs' in vivo function. B16 melanoma cells expressing ovalbumin (B16OVA) were implanted subcutaneously in C57BL/6 recipient mice and allowed to form tumors. A week later, the mice were sublethally irradiated to facilitate T cell engraftment and then injected with in vitro differentiated OT1 CTLs overexpressing miR16, miR200c, or miRScr (FIG. 2A). OT1 CTLs typically delay, but do not prevent, tumor outgrowth in this model. Surprisingly, overexpression of miR16, which induced strong cancer cell killing in vitro, failed to improve anti-tumor responses relative to miRScr (FIG. 2A). Conversely, miR200c profoundly enhanced tumor suppression (FIG. 2A), in stark contrast to its inhibitory effects on cytotoxicity in vitro (FIGS. 1D-1E). To assess the specificity of this surprising anti-tumor phenotype, a "sponge" RNA construct that abrogated the activity of miR200c was developed (FIGS. 9A-9B). Coexpression of this sponge reversed the effects of miR200c on in vitro cytotoxicity and in vivo B16OVA tumor growth (FIGS. 9C-9D), indicating that these phenotypes did indeed result from miR200c dependent gene regulation.

Figure 2B:
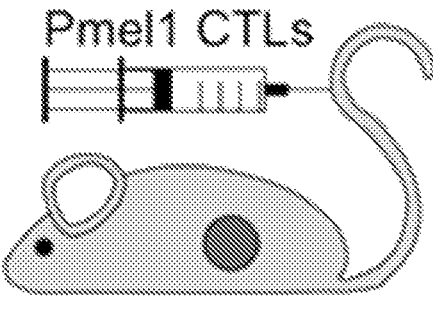
Figure 2B:
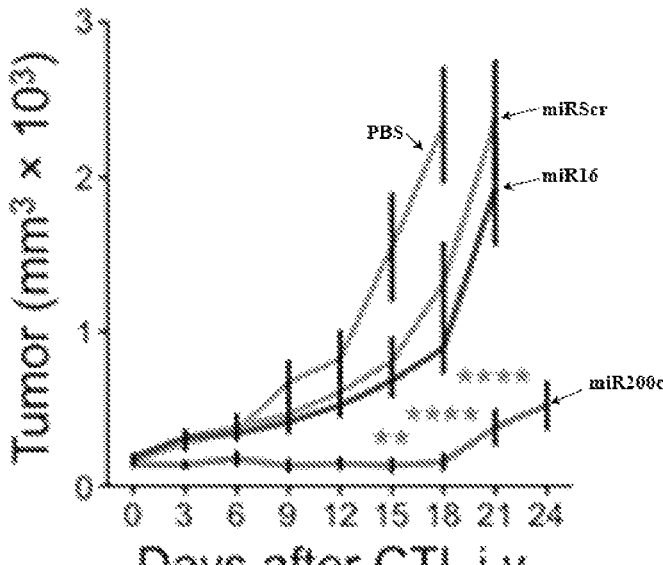
Figure 2B:
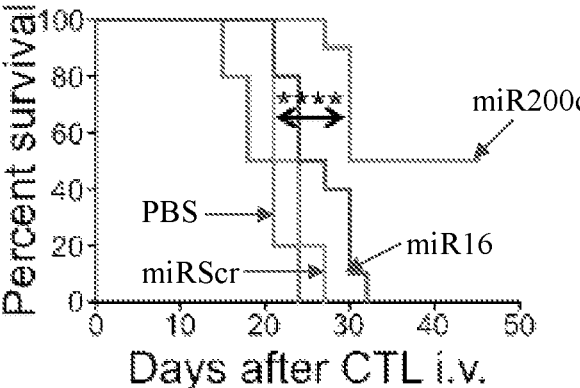
Figure 2C:
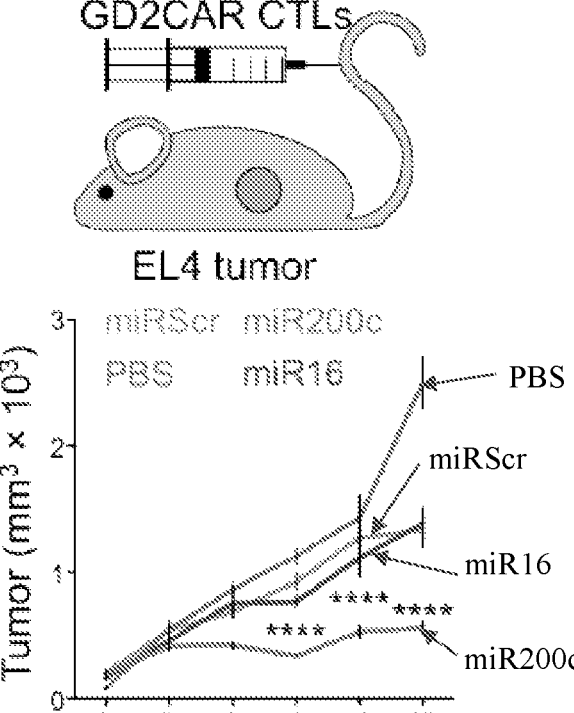
Figure 2C:
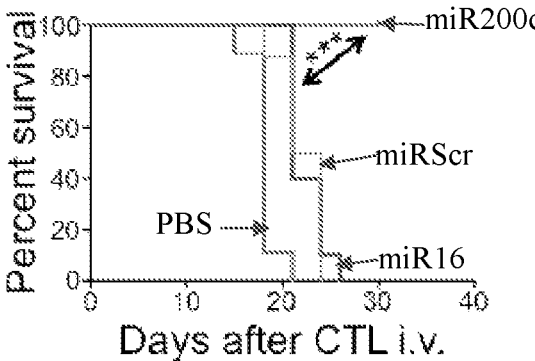

The OT1 TCR binds its cognate antigen with unusually high affinity, raising the possibility that the effects of miR200c on ACT might not apply to T cells with more typical TCRs. To address this issue, ectopic miR200c and miR16 expression was applied to a second ACT system in which B16 tumor-bearing mice were treated with CTLs expressing the Pmel 1 TCR, which recognizes an endogenous melanoma antigen (FIG. 2B). miR200c, but not miR16, significantly improved anti-tumor responses in this model, demonstrating that the capacity of miR200c to augment ACT was not restricted to the OT1 TCR. The ability of miR200c to improve CAR-driven ACT was investigated using a model where CTLs expressing a CAR against the glycolipid tumor antigen GD2 were used to treat mice bearing subcutaneous tumors of GD2+ EL4 cells (FIG. 2C). miR200c CTLs outperformed both miR16 and miRScr CTLs in this system, as well, indicating that the approach is applicable to both CAR- and TCR-driven ACT.

Figure 2D:
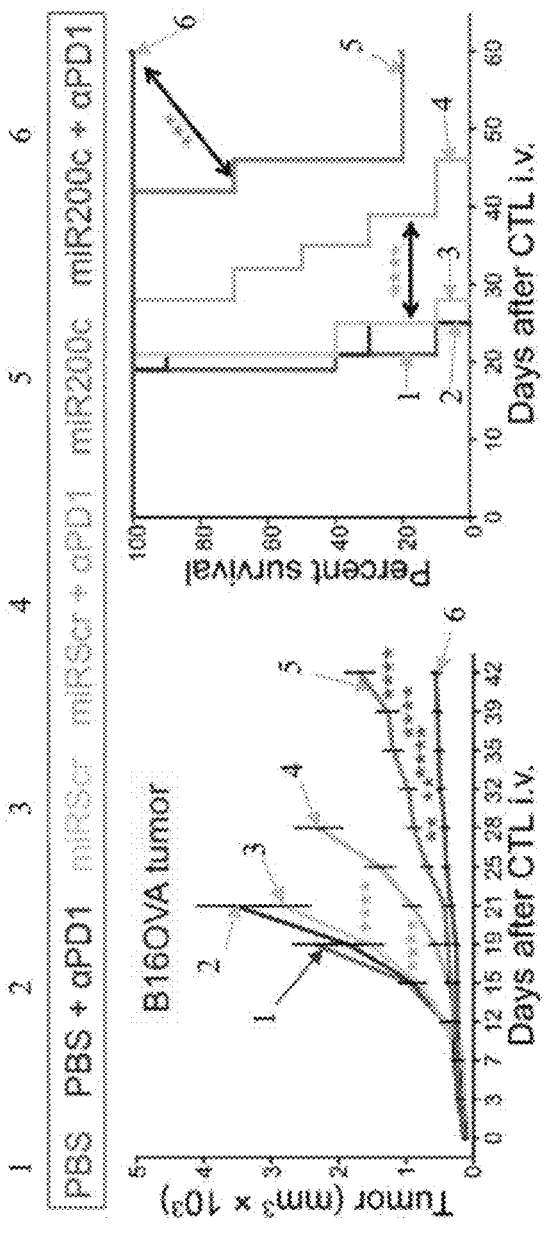
FIG. 2D shows that miR200c enhances anti-tumor function. Mice bearing s.c. B16OVA tumors were injected with OT1 CTLs expressing the indicated miRs and treated with either anti-PD1 antibody (αPD1) or isotype control. Mean tumor volume is plotted on the left, with survival on the right. n=10. All error bars denote SEM. *, , *, and **** indicate P≤0.05, P≤0.01, P≤0.001, and P≤0.0001, respectively, calculated by 2way ANOVA for tumor growth curves and Log-rank test for survival plots.

Finally, experiments were performed to determine whether miR200c overexpression could combine effectively with immune checkpoint blockade (ICB), a class of antibody-based therapies targeting inhibitory lymphocyte immunoreceptors such as PD1. Mice bearing B16OVA tumors were injected with miR200c or miRScr OT1 T cells and then treated biweekly with anti-PD1 or isotype control antibodies. PD1 blockade enhanced the anti-tumor efficacy of both miR200c and miRScr CTLs (FIG. 2D). The combination of miR200c and anti-PD1 was remarkably effective, profoundly suppressing tumor growth and extending the survival of all treated mice past 60 days. Collectively, these results demonstrate that miR200c boosts therapeutic T cell function in a variety of contexts and combines additively with ICB.

Example 4: miR200c Augments CTL Engraftment and Persistence In Vivo

The reduced killing potential of miR200c CTLs implied that their enhanced in vivo functionality might be caused by phenotypic changes unrelated to cytotoxicity. Accordingly, the tissue localization and persistence of these cells were examined after transfer into tumor bearing mice.

Figure 3A:
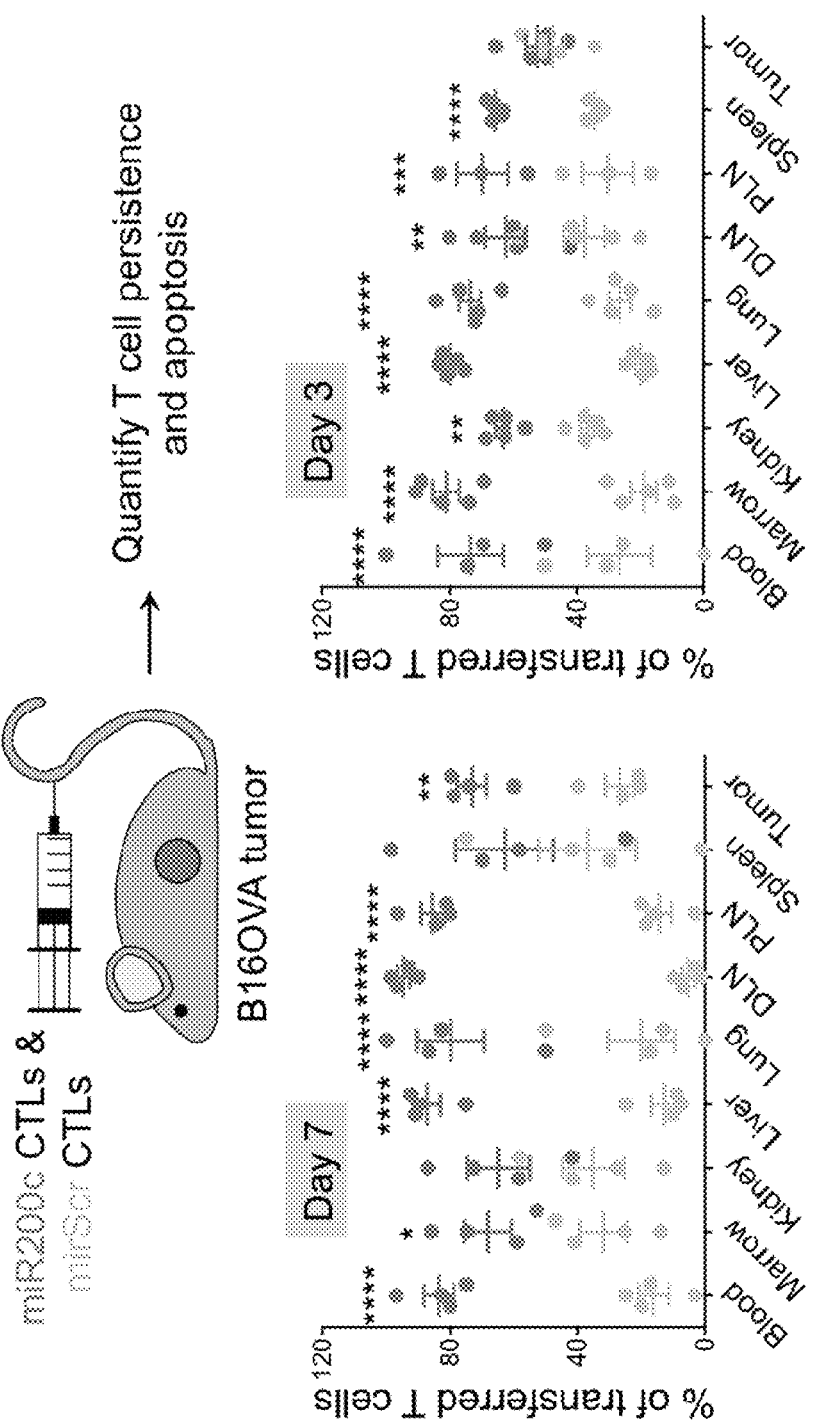
FIGS. 3A-3C show that shows miR200c promotes CTL survival and effector function. For FIG. 3A, a 1:1 mixture of miR200c and miRScr OT1 CTLs was transferred into B16OVA tumor bearing mice. After 3 and 7 days, CTLs were extracted from various organs and analyzed by flow cytometry. Above, schematic diagram of the experiment. Below, graphs showing miR200c and miRScr CTL persistence in various organs after 7 (left) and 3 (right) days. n≥3 per group. For FIG. 3B, mice bearing s.c. B16OVA tumors were injected with either miR200c (red) or miRScr (cyan) OT1 CTLs. After 3 days, OT1 CTLs were extracted from the indicated organs and assessed for caspase activity using CellEvent Caspase 3/7.
Figure 10A:
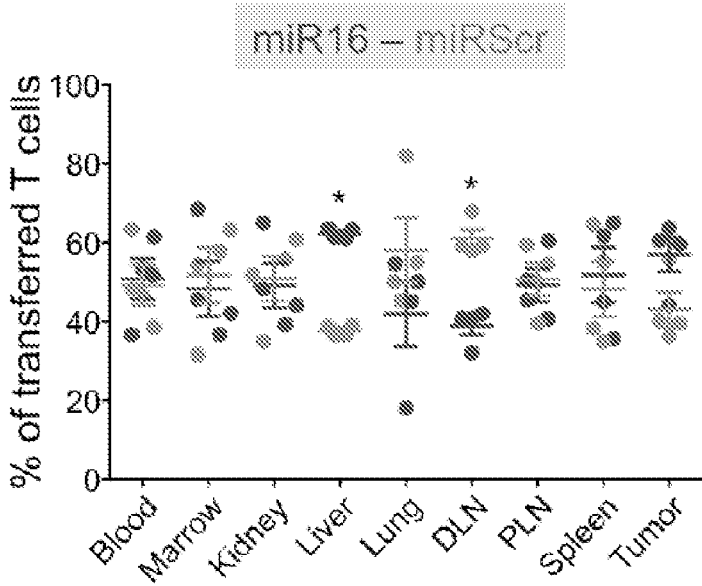
FIGS. 10A-10C show tissue infiltration and persistence of miR200c CTLs. Related to FIGS. 3A-3F. For FIGS. 10A-10B, a 1:1 mixture of miR16 and miRScr OT1 CTLs (FIG. 10A) or miR200c and miRScr OT1 CTLs (FIG. 10B) was transferred into mice with either B16OVA (FIG. 10A) or B16 (FIG. 10B) tumors (n≥3 for each group). After 7 days, CTLs were extracted from various organs and quantified by flow cytometry. Data are representative of at least 2 independent experiments.
Figure 10B:
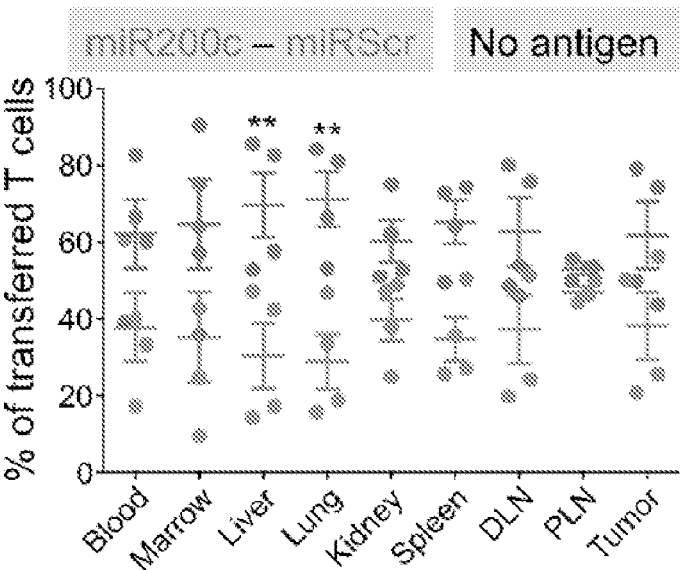
Figure 10C:
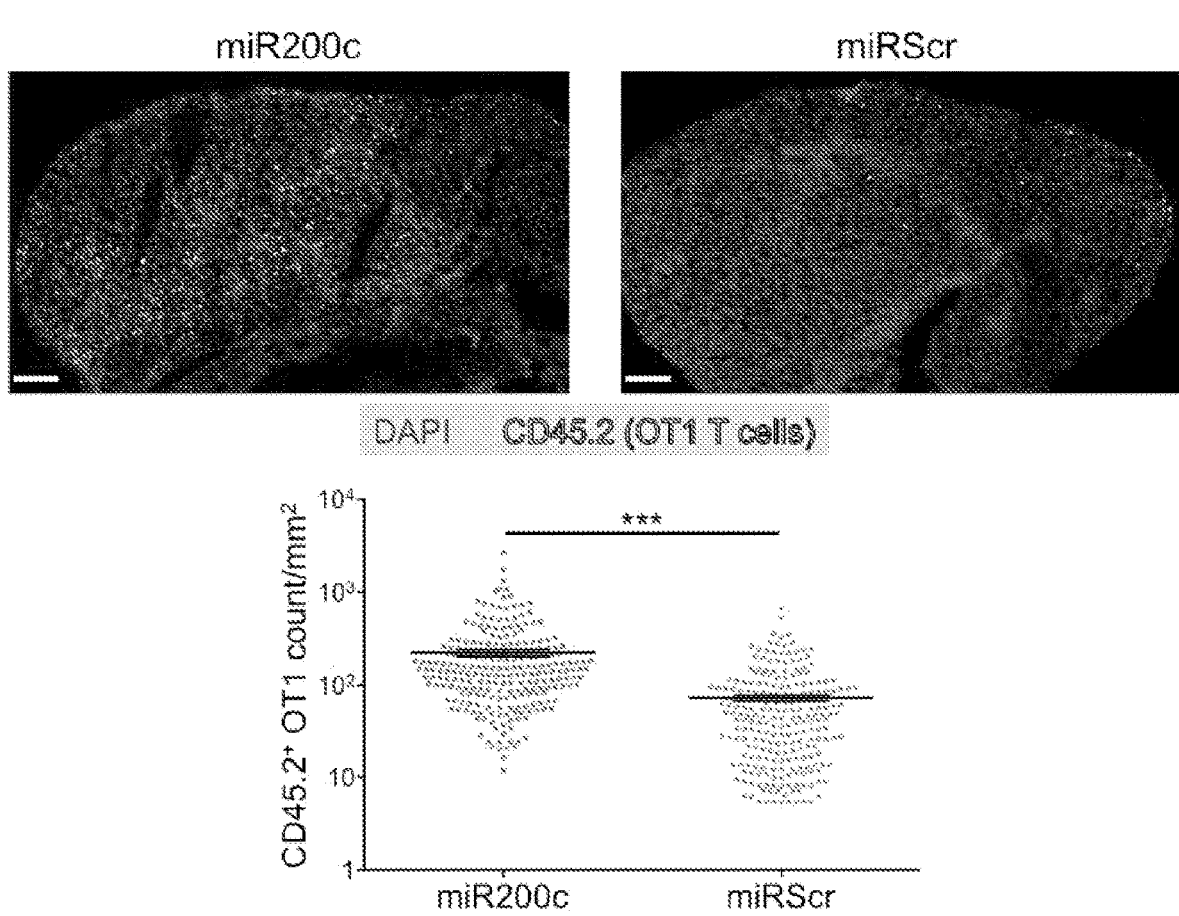

OT1 CTLs expressing either miR200c or miR16 were mixed 1:1 with OT1 miRScr controls and then injected into irradiated, congenically marked recipients bearing B16OVA tumors (FIG. 3A). After one week, OT1 T cells were quantified in the tumor, blood, spleen, lymph nodes, and peripheral organs. miR200c, but not miR16, increased CTL persistence in all locations (FIG. 3A, FIG. 10A). This phenotype did not depend entirely on antigen, as miR200c OT1 CTLs also outcompeted controls in mice carrying B16 tumors without OVA, albeit to a lesser extent (FIG. 10B). To confirm these observations, B16OVA tumor sections from recipient mice treated with either miR200c CTLs or miRScr CTLs were examined. This histological analysis revealed significantly higher densities of miR200c CTLs than miRScr controls in the tumor microenvironment (FIG. 10C), consistent with our flow cytometry-based results.

Figure 3B:
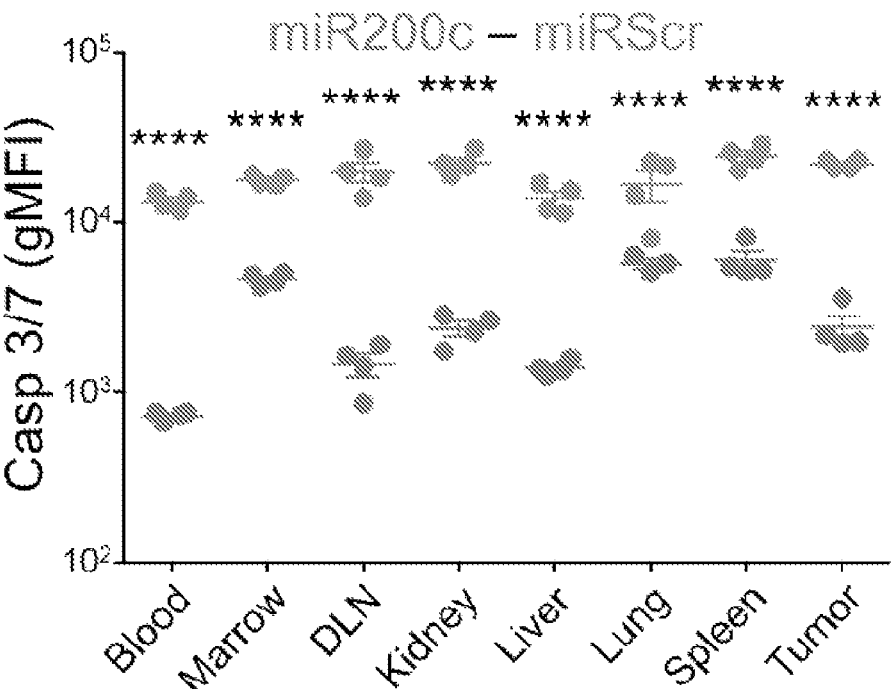
Figure 3C:
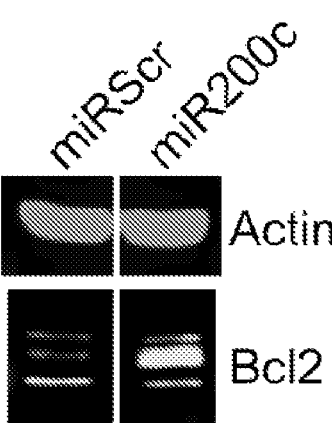
Figure 3D:
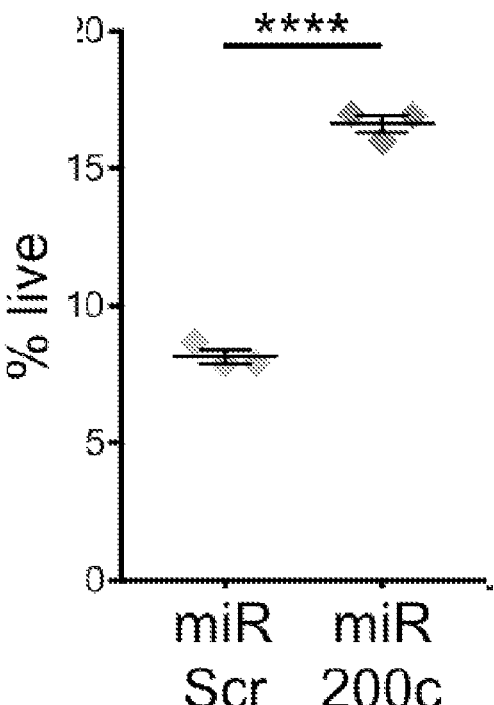
FIG. 3E shows CellEvent Caspase 3/7 staining of miR200c and miRScr CTLs cultured in RPMI with either 30 IU/ml IL2 (left) or 5 ng/ml IL7 (right). n=3 for each group.
FIG. 3F shows CellEvent Caspase 3/7 staining of miR200c and miRScr CTLs treated with 2 μM staurosporine or 20 ng/ml FasL. n=3 for each group. All data are representative of at least 2 independent experiments. See also FIGS. 10A-10C and FIGS. 11A-11J.
Figure 3E:
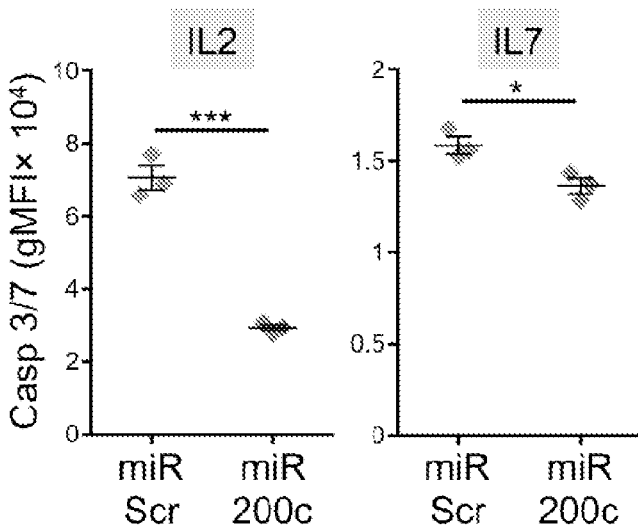
Figure 3F:
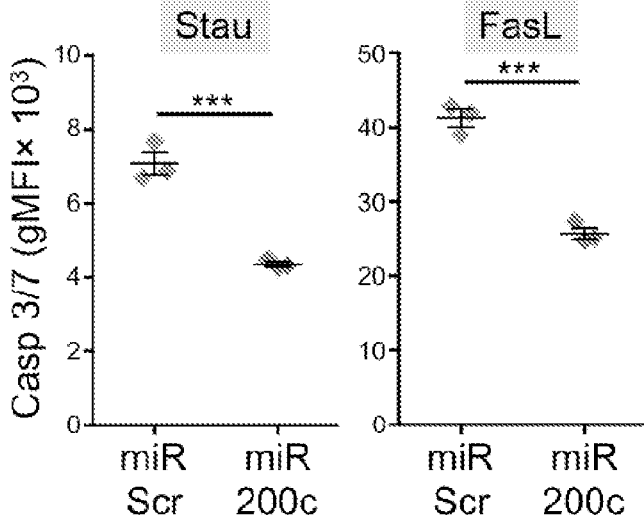

Enhanced miR200c CTL persistence manifested within three days of injection (FIG. 3A), suggesting that miR200c might augment survival during the early stages of engraftment. To investigate this hypothesis, CTLs from tumor bearing mice were extracted three days after initial transfer and stained them with CellEvent Caspase 3/7 reagent, a probe for apoptosis. miR200c CTLs exhibited markedly reduced caspase activation at this early time point (FIG. 3B), suggesting that they can resist the apoptosis associated with engraftment more effectively than controls. Consistent with this interpretation, miR200c CTLs expressed higher levels of the anti-apoptotic protein Bcl2 (FIG. 3C), and they survived better in vitro after transfer into growth medium lacking interleukin-2 (IL2) (FIG. 3D). Additional in vitro experiments indicated that miR200c CTLs were significantly less susceptible to apoptosis at steady state, regardless of whether CTLs were cultured in IL2 or IL7 (FIG. 3E). Overexpression of miR200c also dampened apoptotic responses to the cell death inducers staurosporine and Fas ligand (FIG. 3F). Hence, miR200c transduction promotes the survival of therapeutic T cells.

Figure 11A:
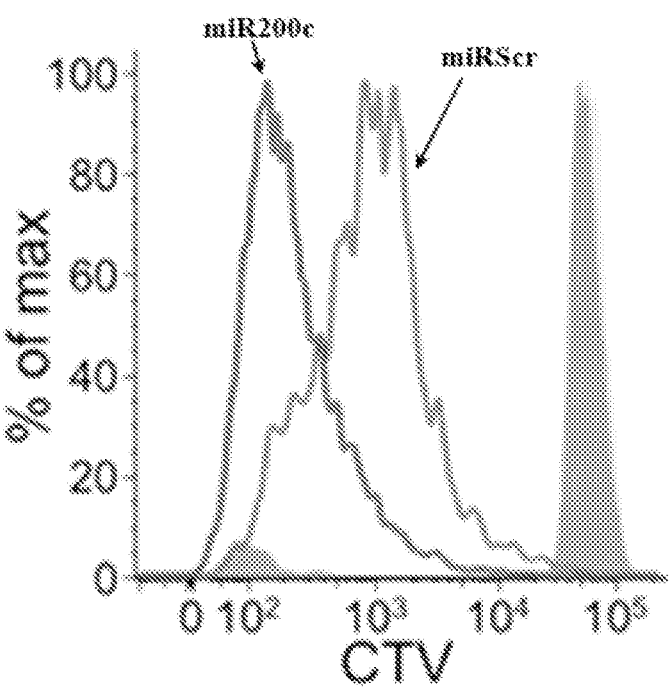
FIGS. 11A-11J show characterization of miR200c CTLs. Related to FIGS. 3A-3F and FIGS. 4A-4H. For FIG. 11A, miRScr and miR200c OT1 CTLs were stained with CTV and then stimulated with OVA-loaded splenocytes. CTV dilution was evaluated after 5 days. Shaded curves denote time 0.
Figure 11B:
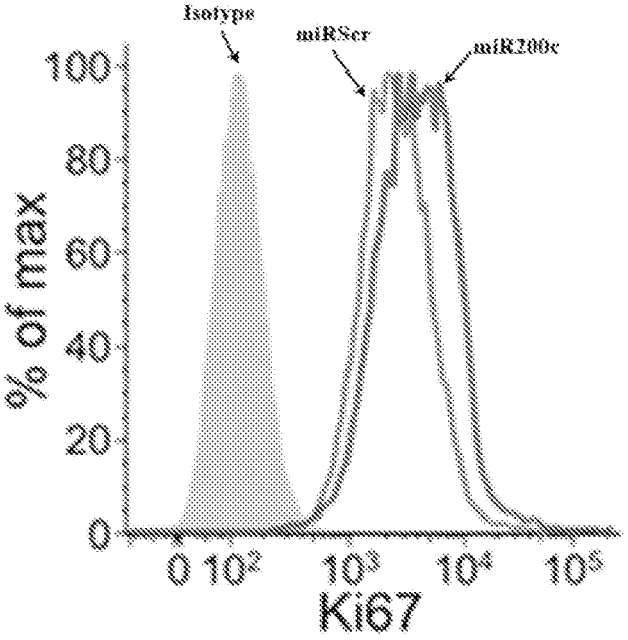
Figure 11C:
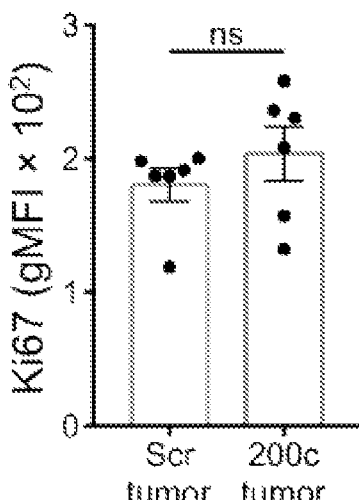

Next, experiments were performed to investigate whether miR200c conferred CTLs with enhanced proliferation, as this could also explain the observed persistence phenotype. miR200c CTLs did divide somewhat more extensively than miRScr controls after antigenic stimulation in vitro, and they also expressed slightly more of the proliferation marker Ki67 (FIGS. 11A-11B). No higher levels of Ki67 were observed in vivo, however, implying little to no proliferative advantage after infusion (FIG. 11C). These results demonstrate that the in vivo persistence phenotype of miR200c CTLs is more likely due to increased survival than enhanced proliferation.

Example 5: miR200c Promotes TCF1 and TNF Expression in Tumors

Figure 4A:
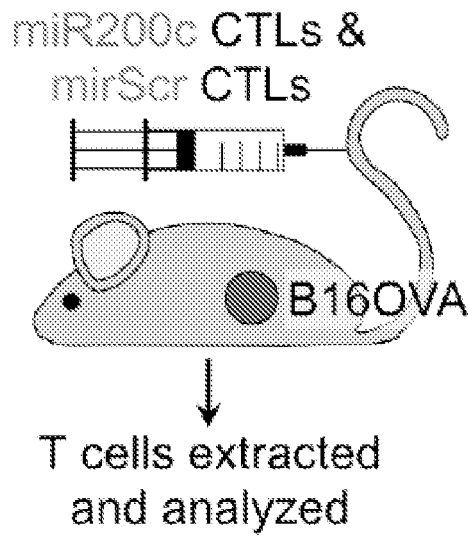
FIGS. 4A-4H show that miR200c promotes CTL survival and effector function. A 1:1 mixture of miR200c and miRScr OT1 CTLs was transferred into B16OVA tumor bearing mice. At various time points, CTLs were extracted and analyzed by flow cytometry.
Figure 4B:
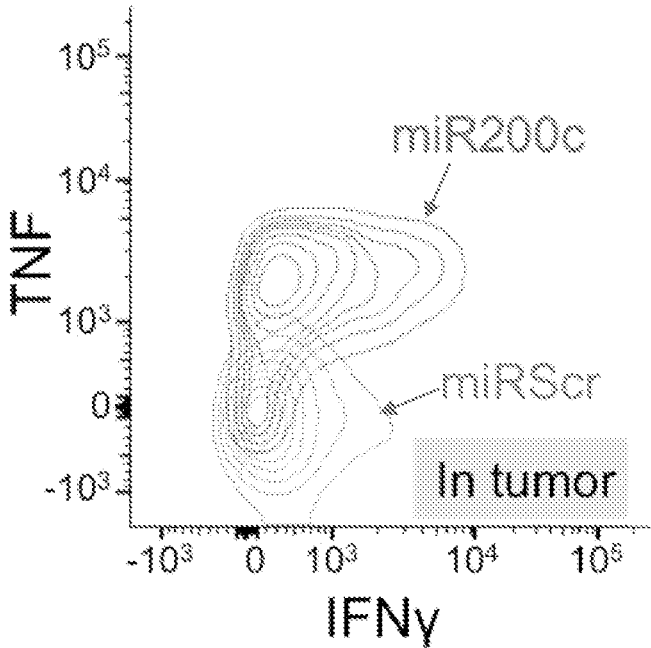
Figure 4C:
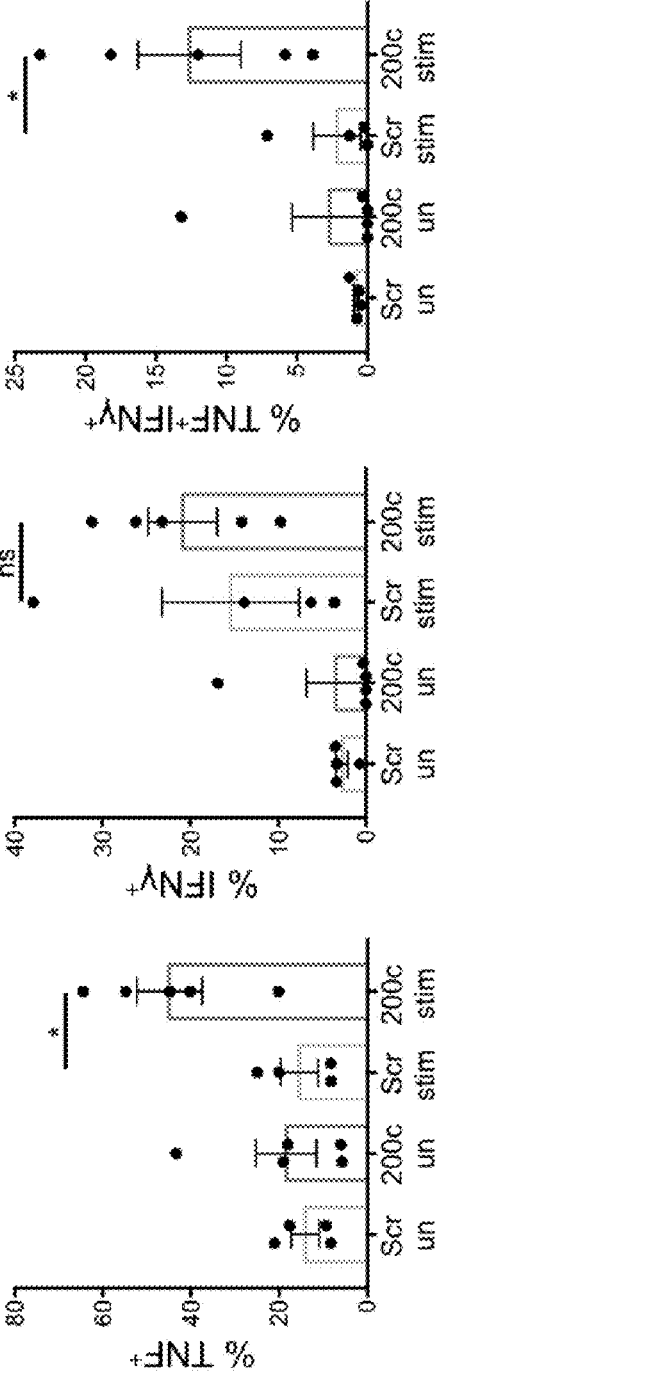
Figure 11D:
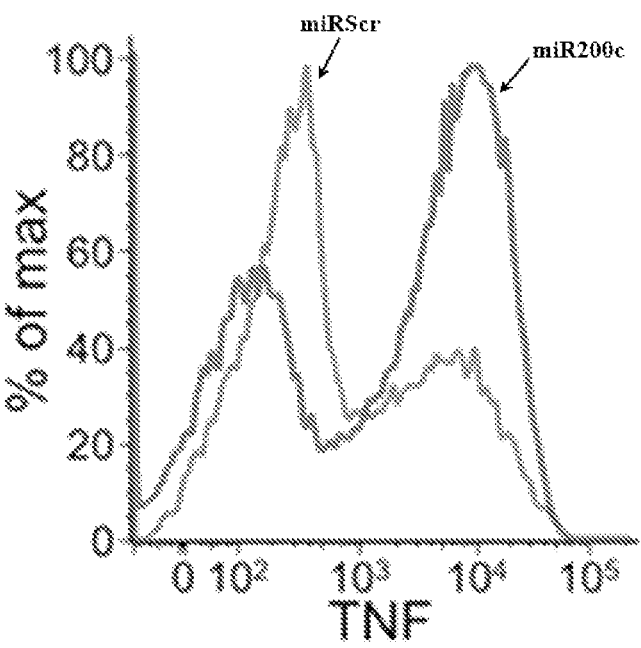
Figure 11E:
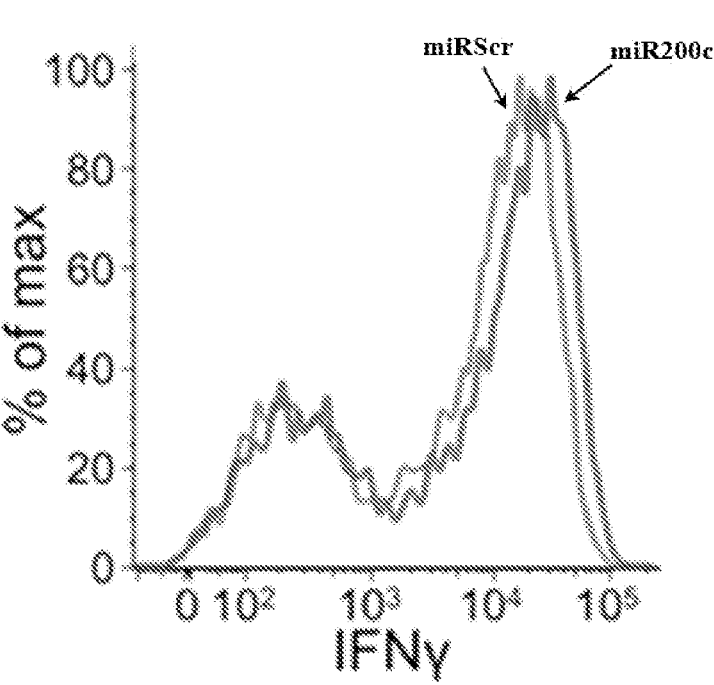

To further explore the functional ramifications of miR200c in T cells, CTLs were activated in vitro and cytokine production was measured. miR200c CTLs generated much more tumor necrosis factor (TNF) than miRScr controls, while interferon-γ (IFNγ) responses were comparable (FIGS. 11D-11E). The same pattern of results were observed after restimulation of CTLs extracted from B16OVA tumors; miR200c dramatically enhanced TNF production without altering interferon-γ (IFNγ) responses (FIGS. 4A-4C). Hence, miR200c augments not only the survival but also the functional capacity of CTLs both in culture and in the tumor microenvironment.

Figure 4D:
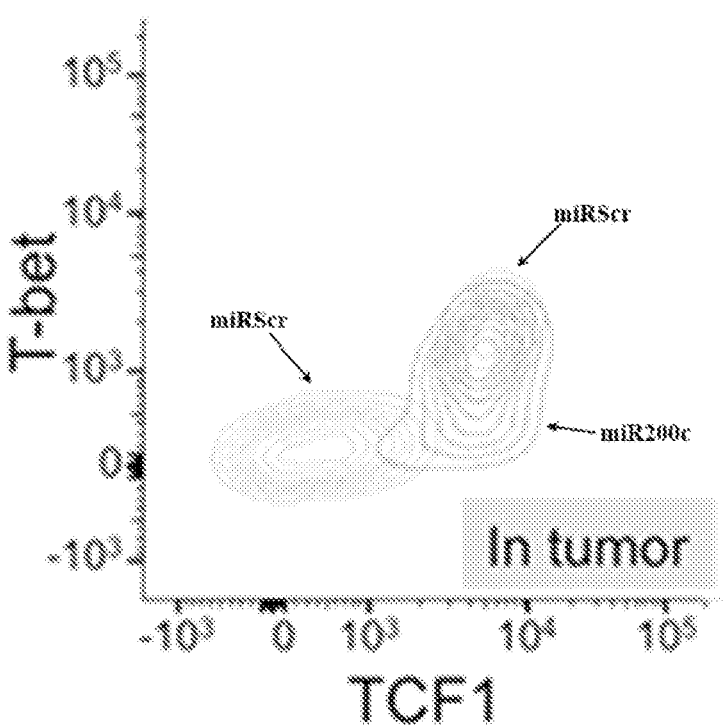
Figure 4E:
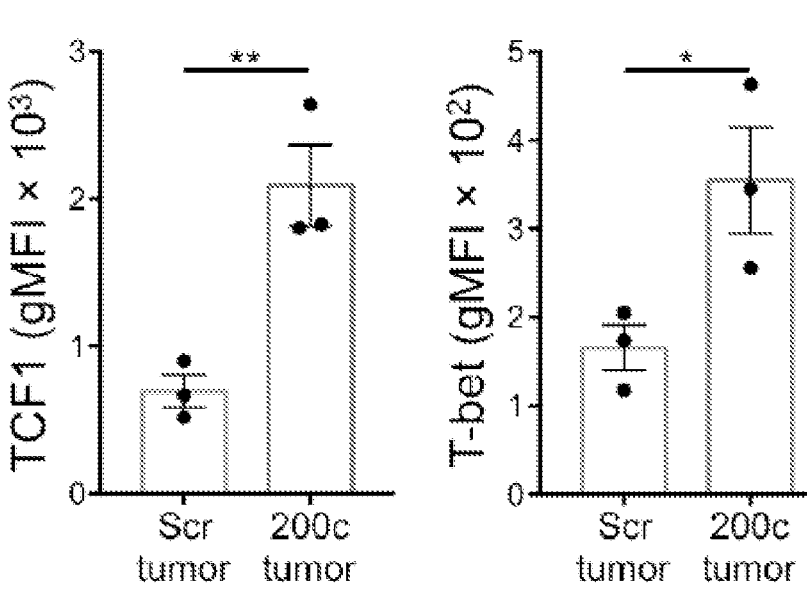
Figure 11F:
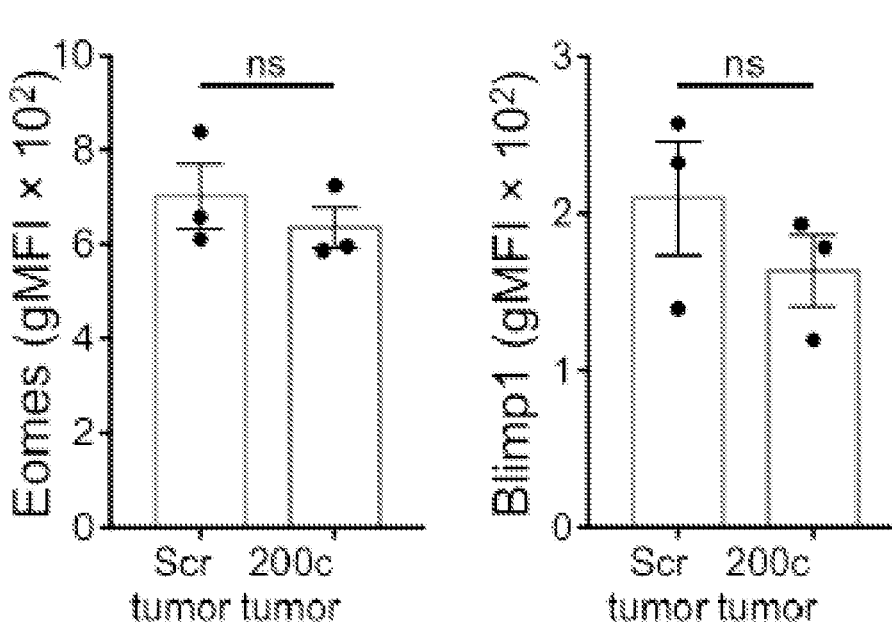
Figure 11G:
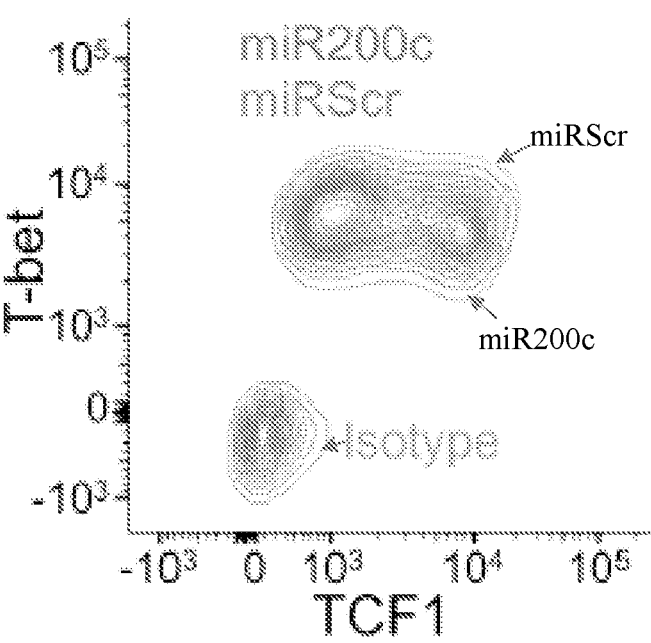

The expression of critical transcription factors that control T cell differentiation was also examined. Tumor infiltrating miR200c CTLs displayed markedly higher levels of TCF1 protein (FIGS. 4A, 4D-4E), consistent with their enhanced survival and anti-tumor activity. They also expressed significantly more of the T-box family member T-bet (FIGS. 4D-4E), which has been associated with sustained functionality in the context of chronic antigen exposure. Conversely, overexpression of miR200c did not alter the expression of Eomes and Blimp1 (FIG. 11F), two transcription factors that characterize differentiated effector subsets. Interestingly, cultured miR200c and miRScr CTLs expressed similar amounts of TCF1 and T-bet in vitro (FIG. 11G), implying that the upregulation of these transcription factors by miR200c also requires some feature of the in vivo environment. Taken together, these results indicate that miR200c predisposes CTLs to acquire the transcriptional indices of self-renewal and pluripotency in vivo.

Figure 4F:
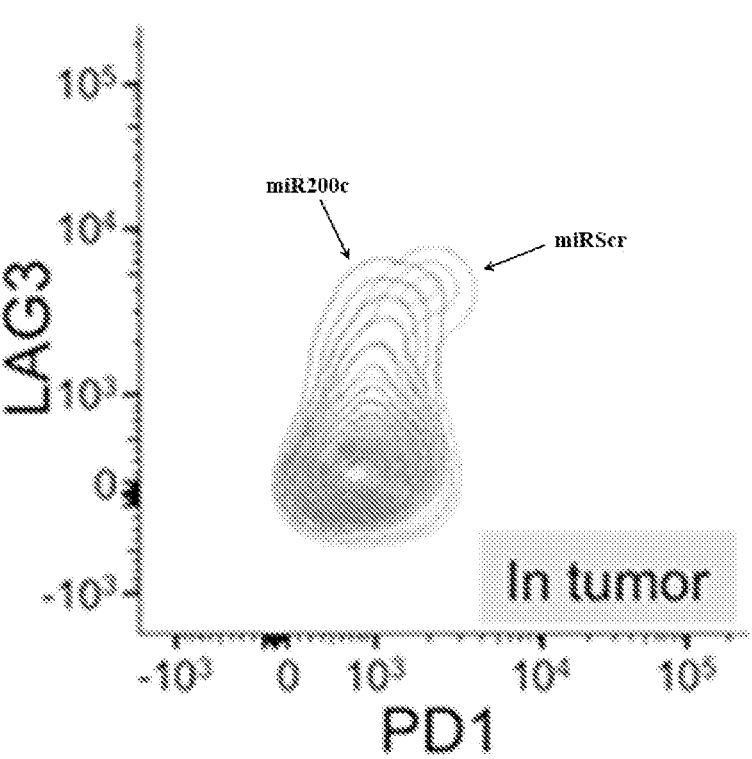
Figure 4G:
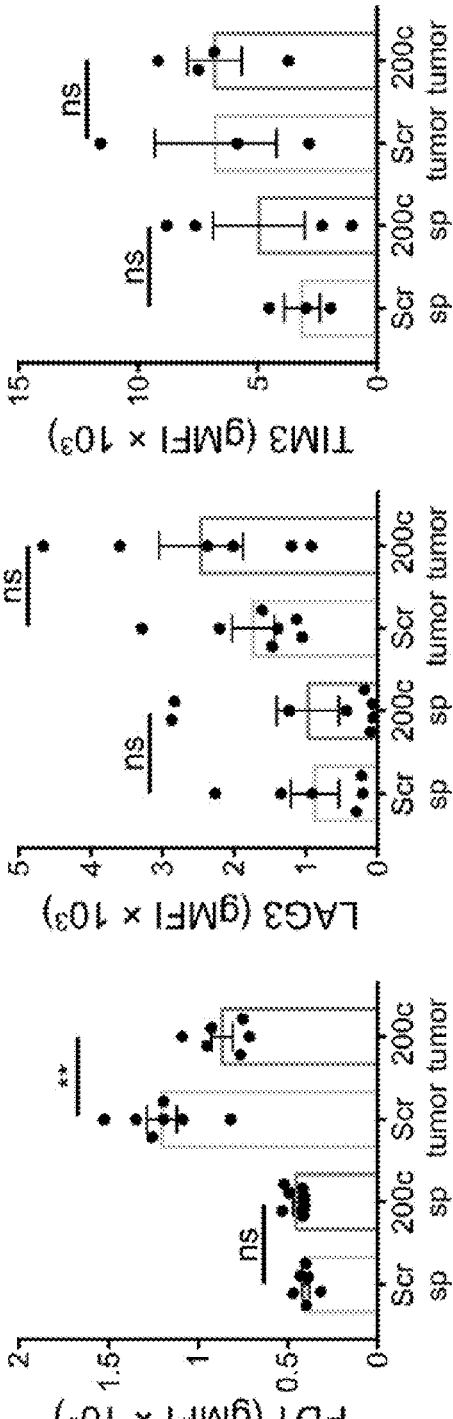
Figure 11H:
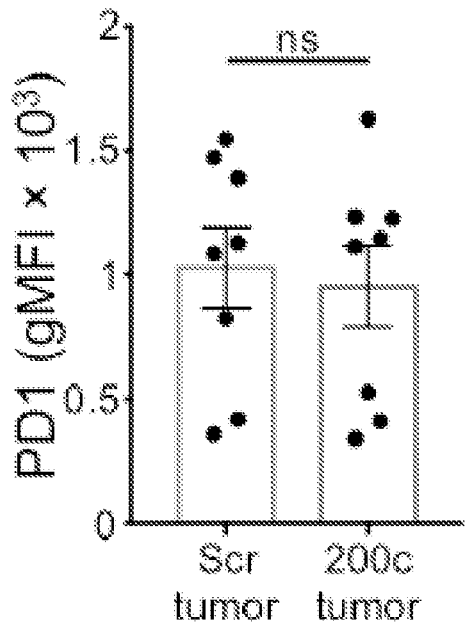

Sustained T cell functionality in the presence of antigen is typically limited by the onset of exhaustion. To assess whether miR200c overexpression alters this process, cell surface levels of PD1, LAG3, and TIM3, three inhibitory receptors associated with the exhausted state were quantified. Compared to miRScr controls, tumor-infiltrating miR200c CTLs expressed equivalent amounts of LAG3 and TIM3 and slightly less PD1 two weeks after infusion (FIGS. 4F-4G). Notably, this modest reduction in PD1 expression was not apparent at the one-week time point (FIG. 11H), when enhanced miR200c CTL persistence and tumor suppression is already apparent (FIG. 2). Hence, it seems unlikely that the robust anti-tumor activity of miR200c CTLs resulted from the suppression of canonical T cell exhaustion.

Figure 4H:
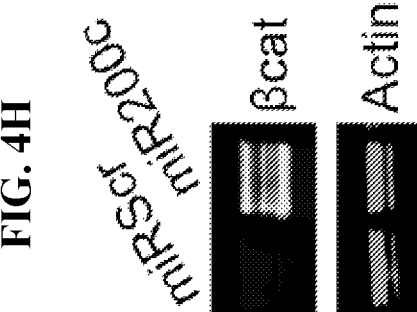
Figure 11I:
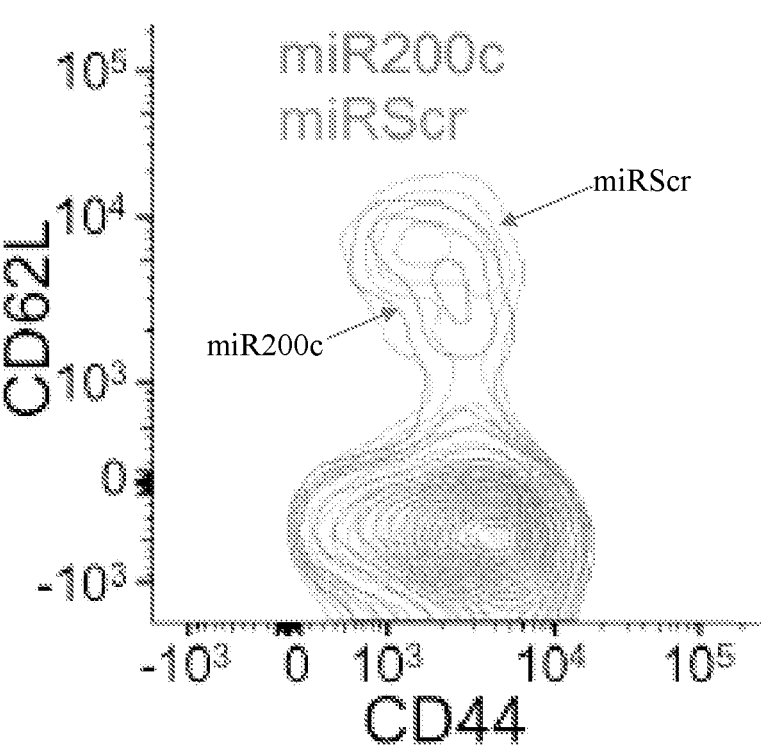

Prolonged in vivo persistence and high expression of TCF1 and Bcl2 are hallmarks of stem cell memory T cells (Tscm), which are known to mediate enhanced anti-tumor responses in ACT models. The phenotypic and functional similarities between miR200c CTLs and Tscm cells raised the possibility that they might be the same cell type. Tscm cells can be generated in vitro by pharmacological stabilization of β-catenin, which drives elevated Wnt signaling. Like Tscm cells, miR200c CTLs expressed high levels of β-catenin protein (FIG. 4H). They did not, however, exhibit reduced proliferation and cytokine secretion (FIG. 4 and FIG. S11), which are both Tscm hallmarks. In addition, whereas Tscm cells express high levels of CD62L and low levels of CD44, indicative of attenuated effector differentiation, miR200c transduction failed to alter the expression of either marker (FIG. 11I). These results demonstrate that, despite some similarities with Tscm cells and other memory subsets, miR200c CTLs exhibit a novel phenotype.

Example 6: miR200c Drives Epithelial Genes Via Suppression of Zeb1

Figure 5A:
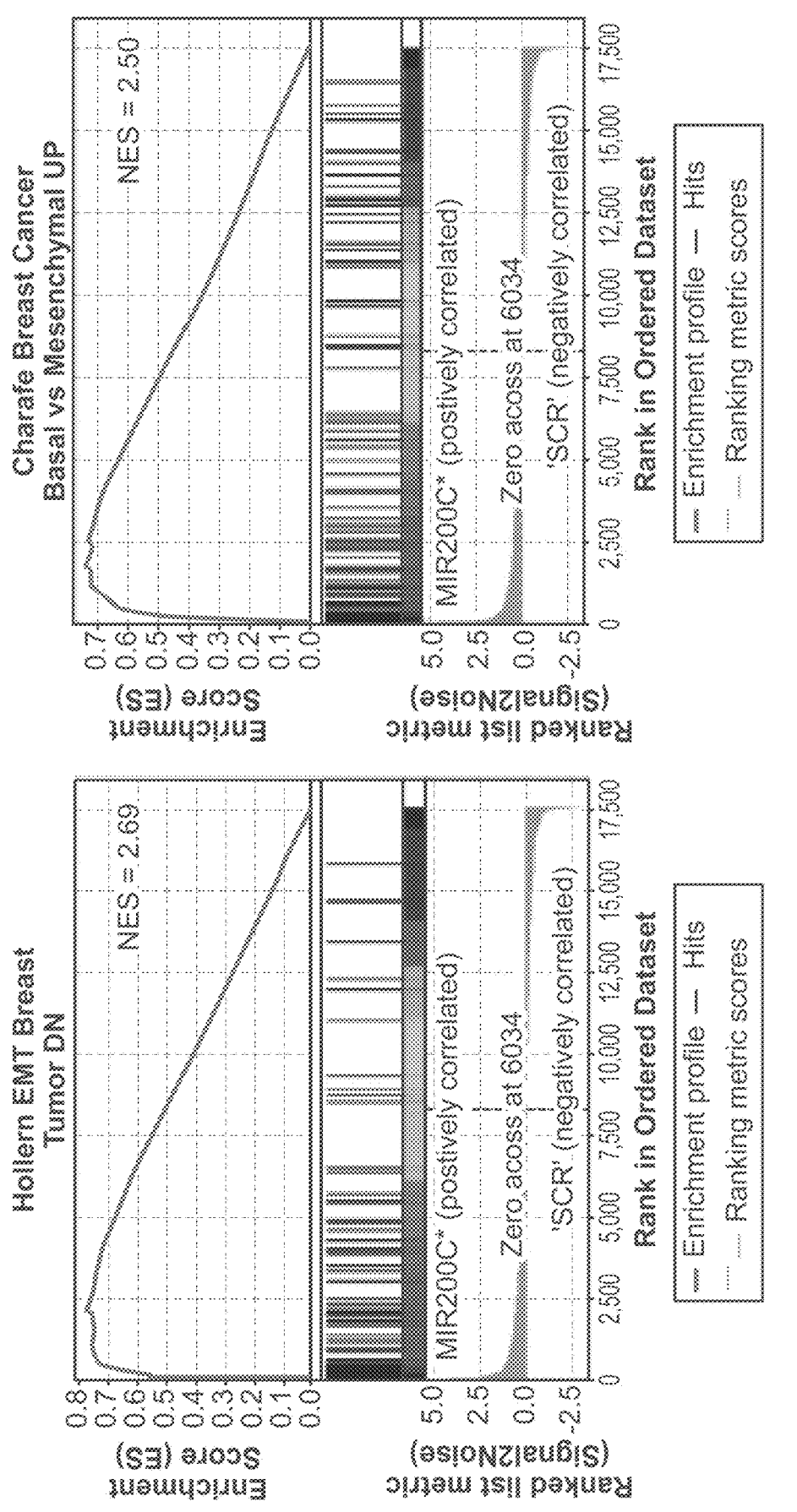
Figure 5A:
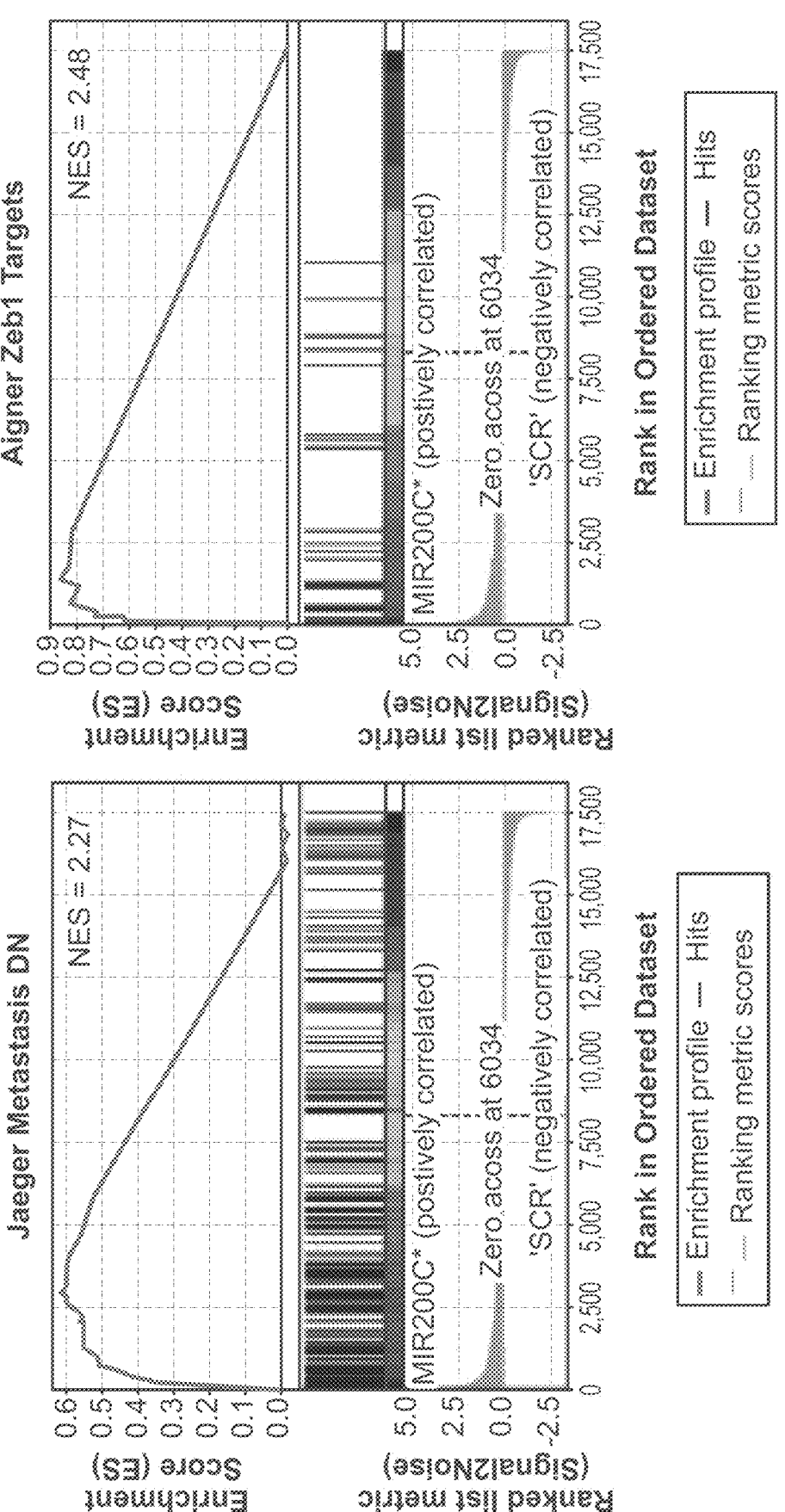
Figure 5B:
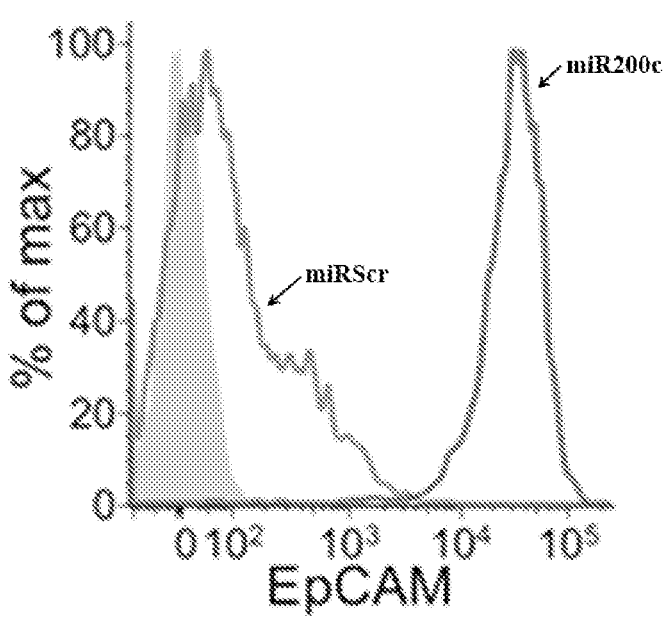
Figure 5C:
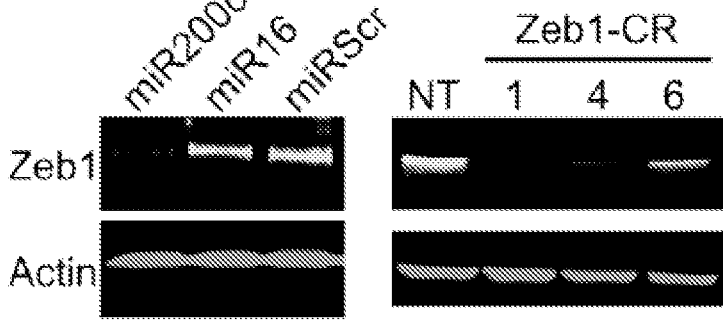
Figure 5D:
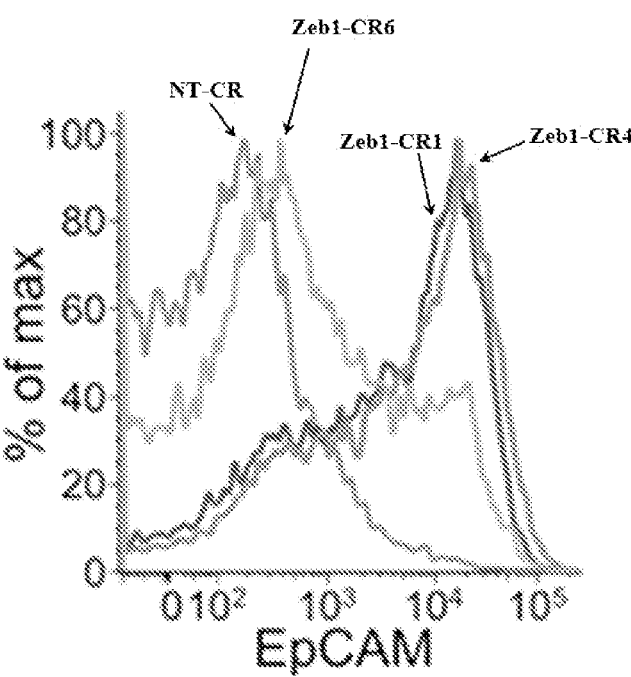
Figure 5E:
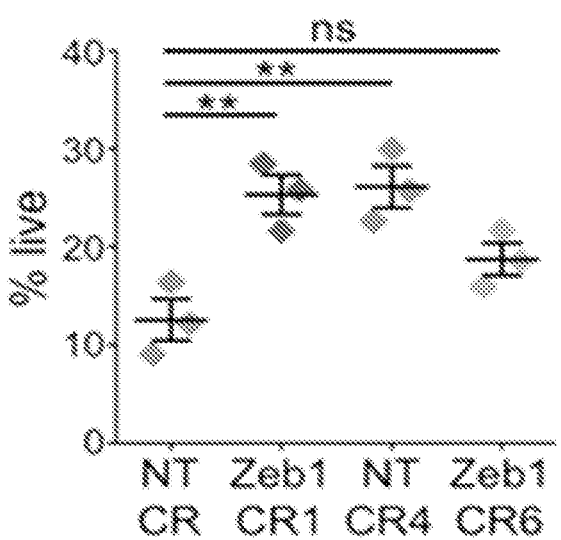
Figure 5F:
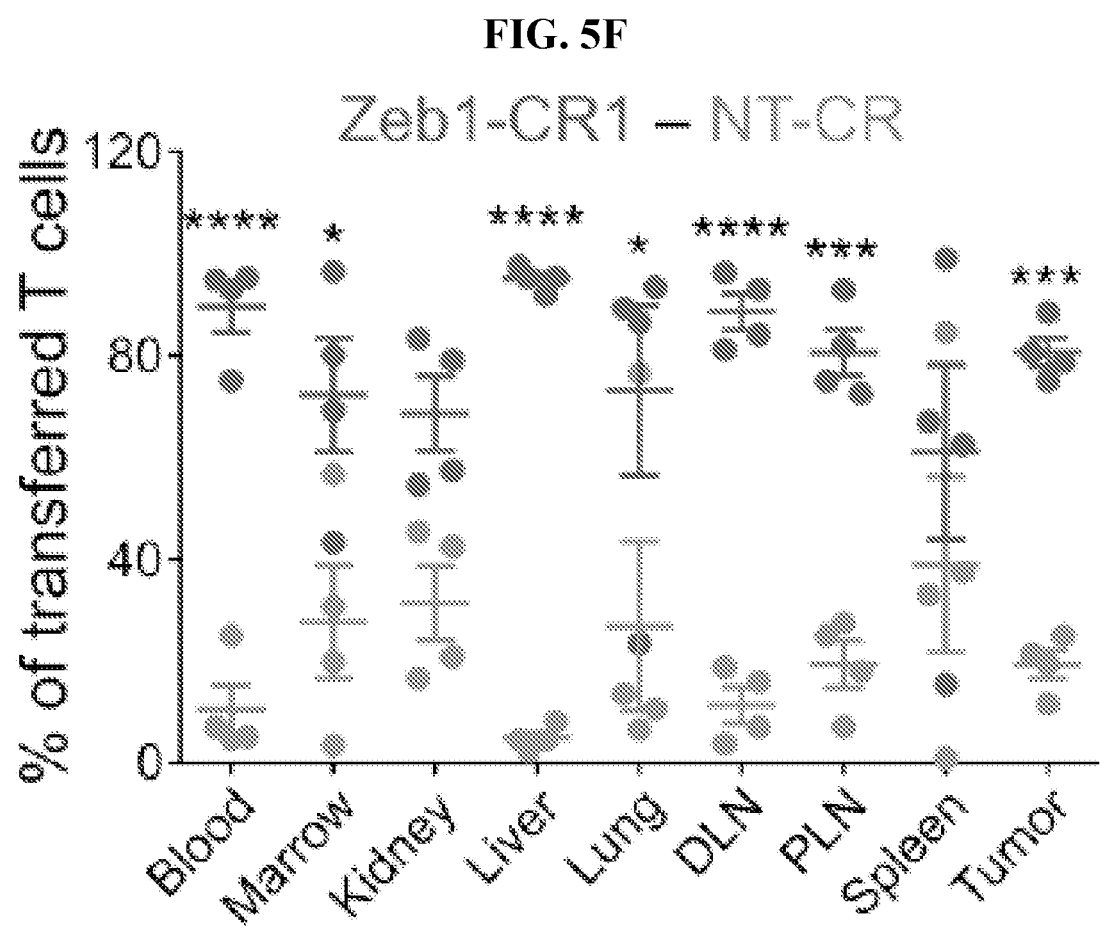
Figure 5G:
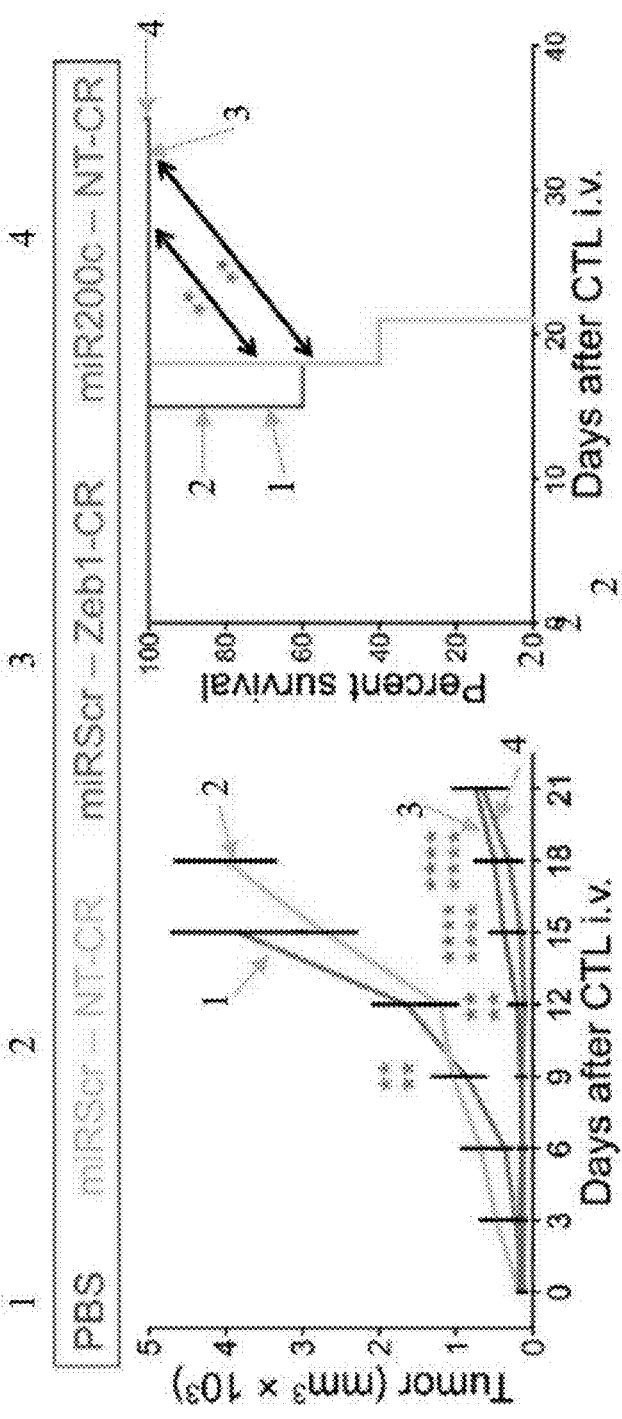
Figure 11J:
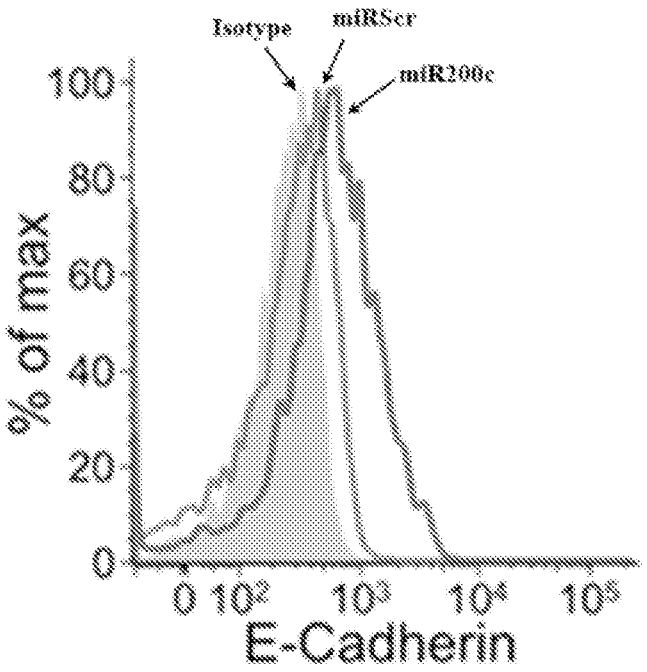
Figure 12A:
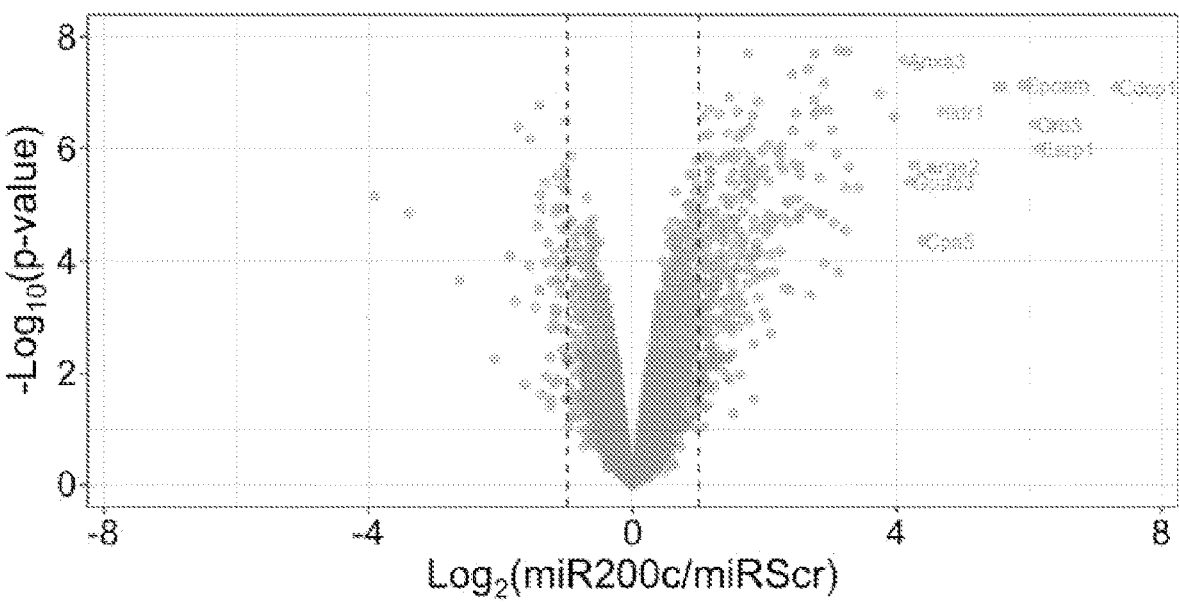
FIGS. 12A-12B show that miR200c does not promote established T cell differentiation pathways. Related to FIGS. 5A-5G.
Figure 12B:
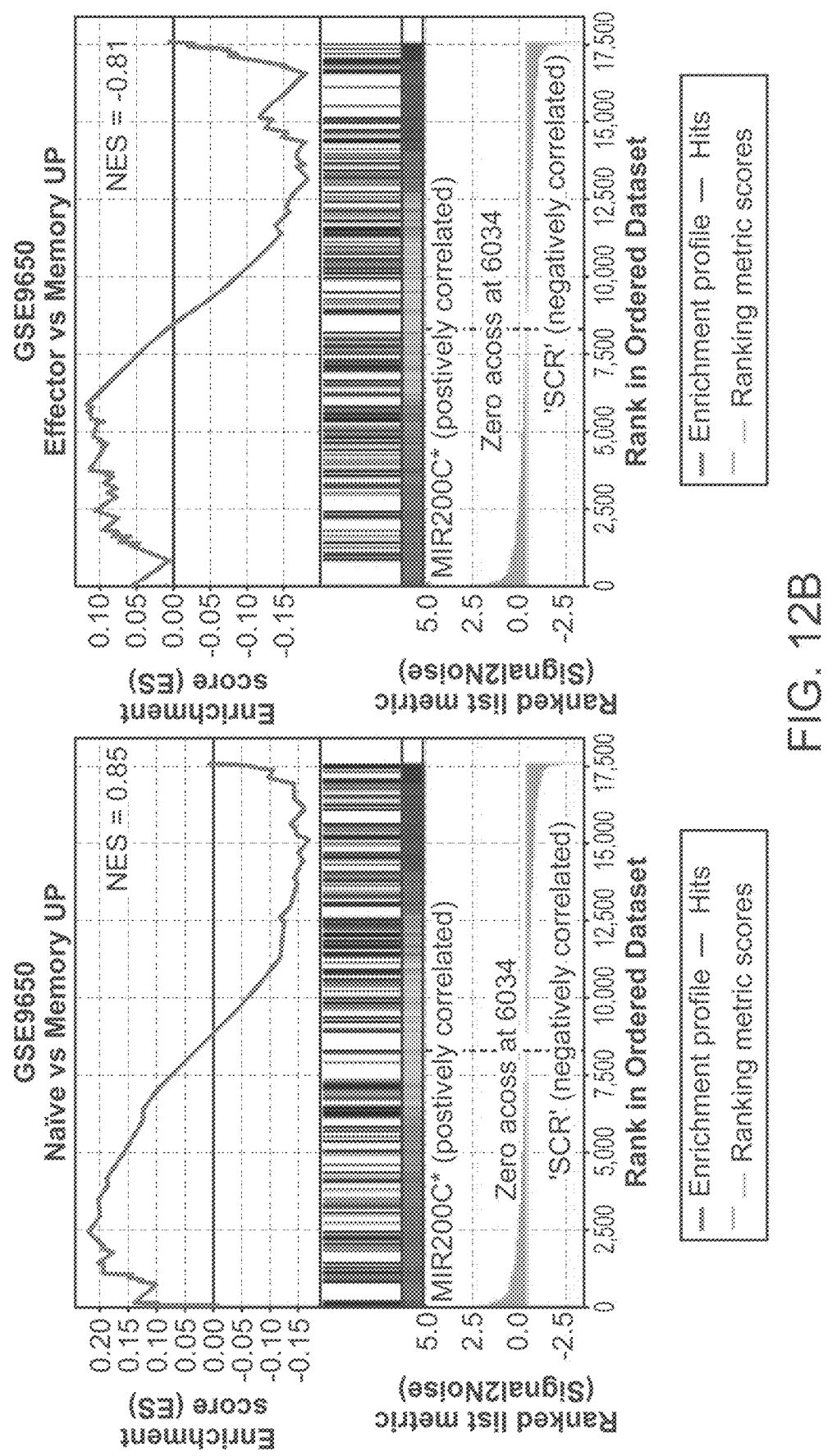
Figure 13A:
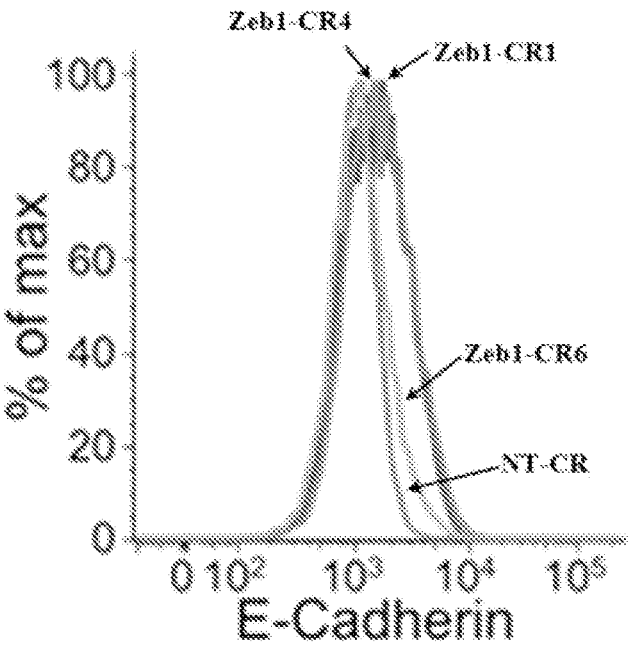
Figure 13B:
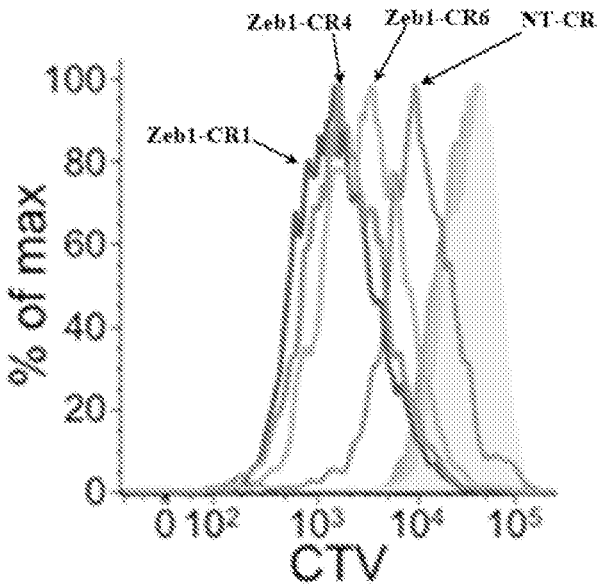
Figure 14A:
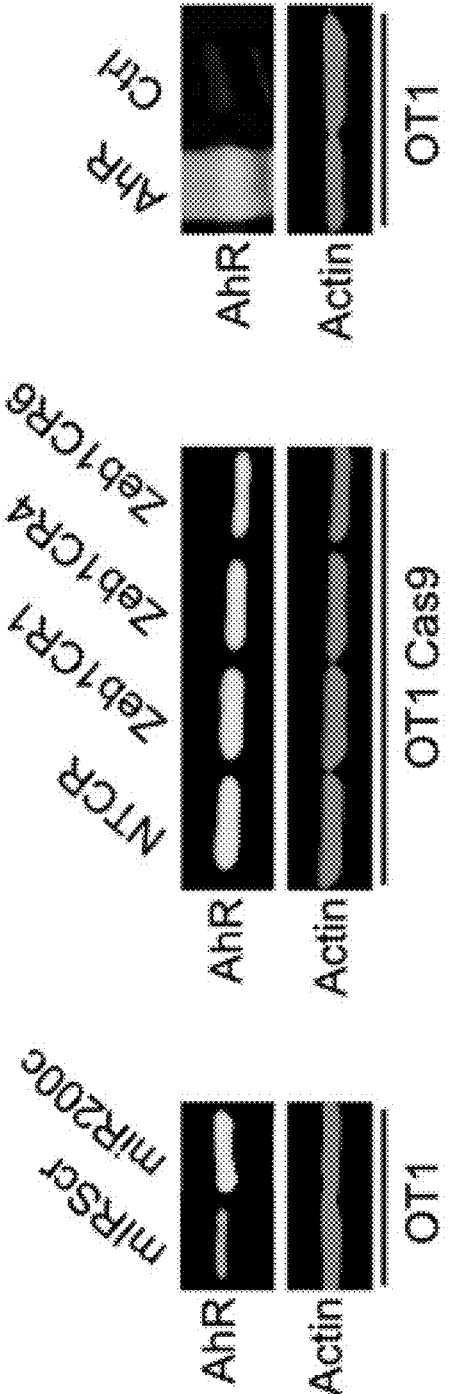
FIGS. 14A-14D show that AhR does not control miR200c dependent enhancement of ACT. Related to FIGS. 5A-5G.
Figure 14B:
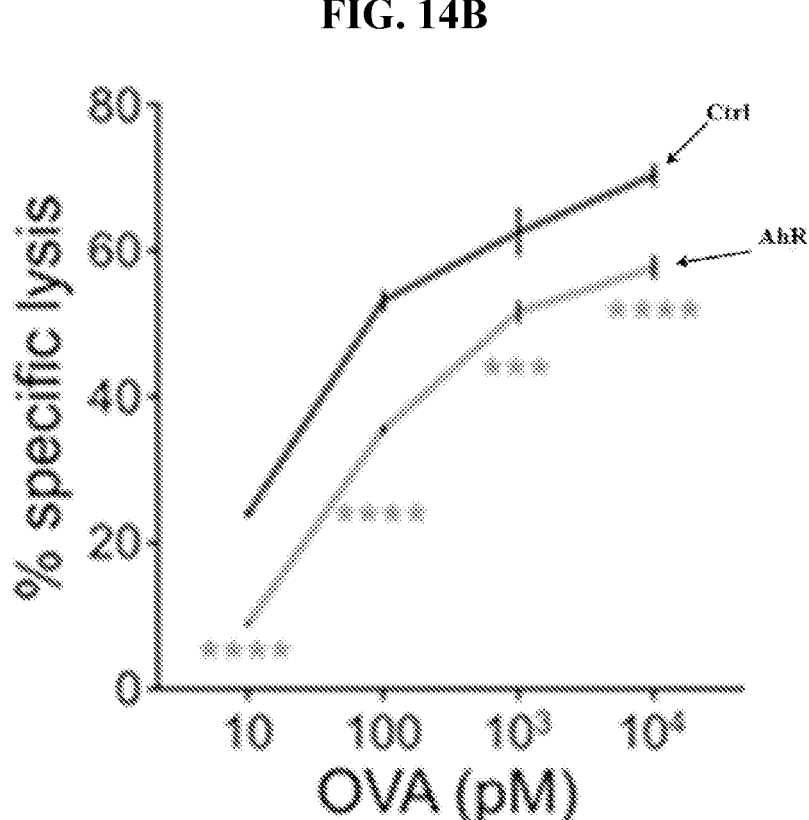
Figure 14C:
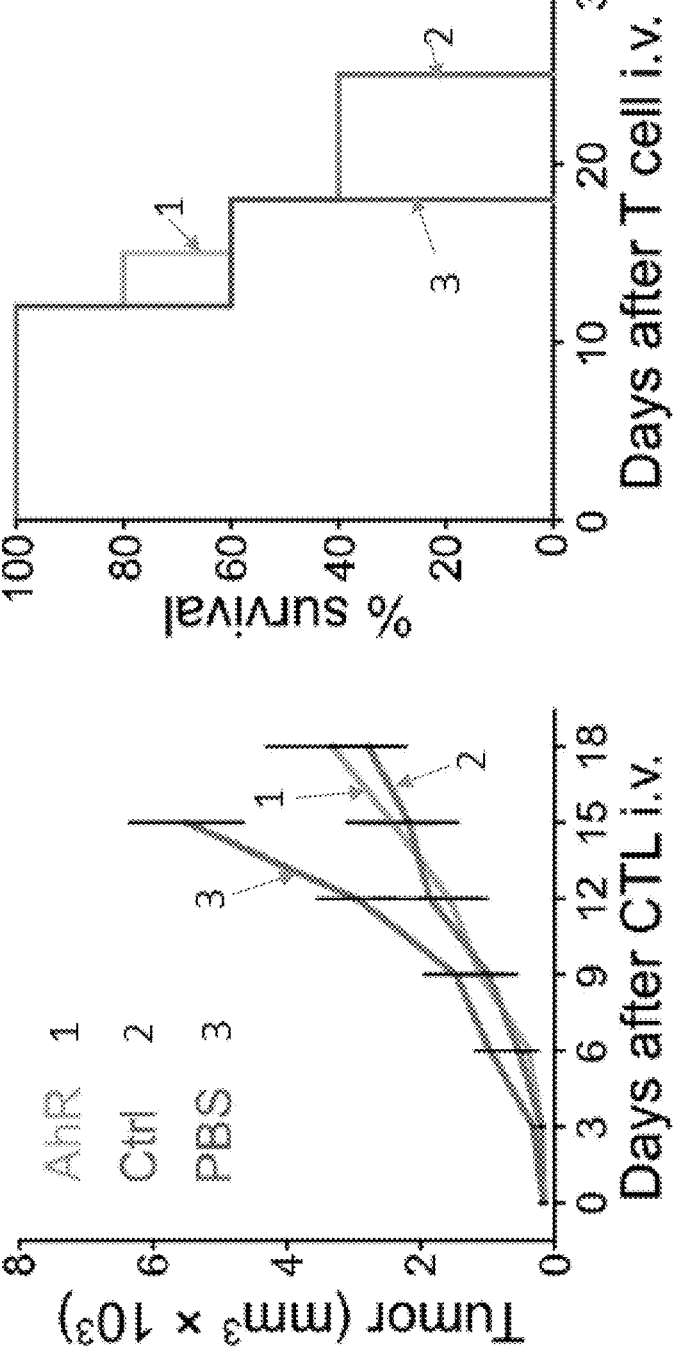
Figure 14D:
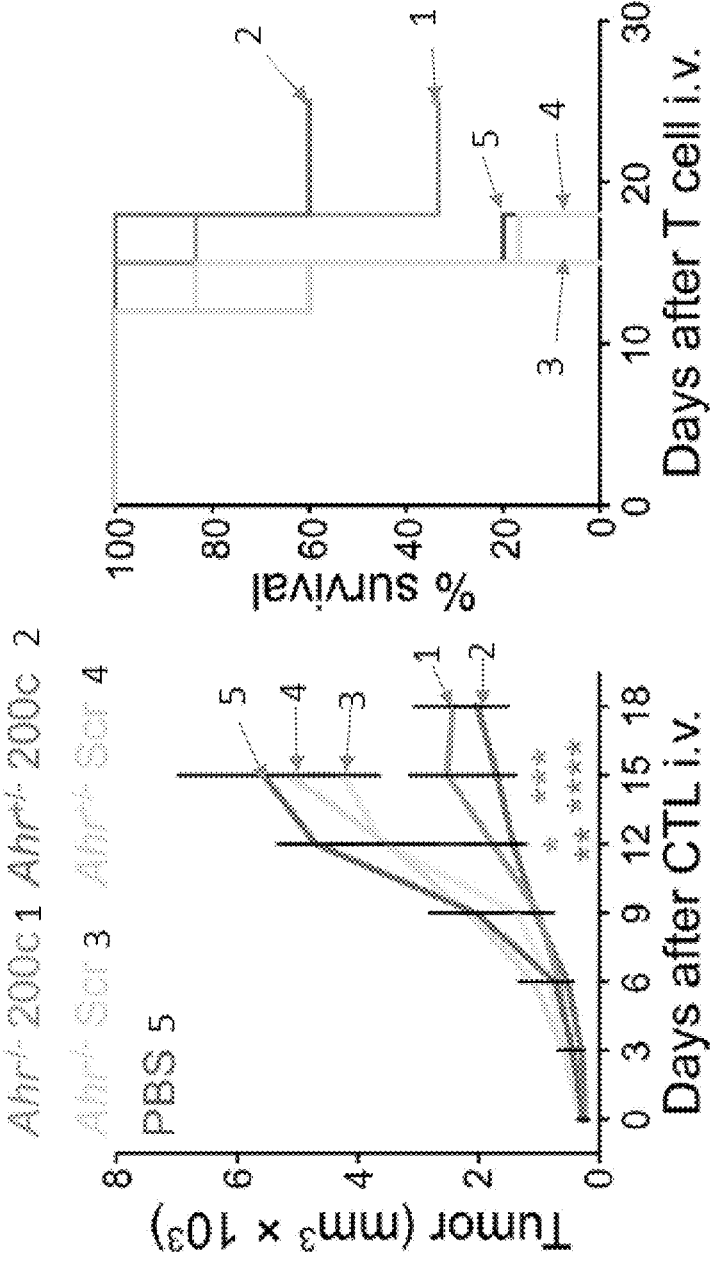

Comparative analysis of whole transcriptome RNA sequencing data from miR200c and miRScr CTLs did not reveal obvious links between miR200c CTLs and established T cell differentiation states. Gene sets associated with T cell memory and exhaustion, for instance, were not markedly enriched relative to those of naïve and effector subsets (FIGS. 12A-12B). By contrast, gene sets characteristic of differentiated epithelial cells, particularly in relation to epithelial-to-mesenchymal transition (EMT) and metastasis, were dramatically upregulated by miR200c (FIG. 5A). Indeed, miR200c CTLs strongly expressed EpCAM and E-cadherin (FIG. 5B and FIG. 11J), two epithelial cell surface markers that are not typically found on lymphocytes. This "epithelialization" phenotype was consistent with the well-established role of miR200c and its homologs (miR200a, miR200b, miR141, miR429) in maintaining epithelial cell fate and restraining malignant transformation.

miR200 family members inhibit EMT and metastasis by blocking expression of the transcription factors Zeb 1 and Zeb2. miR200c sharply downregulated Zeb 1 protein and induced a gene expression signature in CTLs that strongly overlapped with a curated set of Zeb 1 targets (FIGS. 5A, 5C). To determine the importance of Zeb1 for the miR200c CTL phenotype, OT1 T cells expressing the Cas9 nuclease were transduced with guide RNAs (gRNAs) that either completely (CR1 and CR4) or partially (CR6) eliminated Zeb 1 protein (FIG. 5C). Zeb 1 depletion mimicked the effects of miR200c on EpCAM and E-cadherin expression (FIG. 5D and FIG. 13A), in vitro survival and proliferation (FIG. 5E and FIG. 13B), and in vivo persistence (FIG. 5F). In many cases, the severity of the phenotype scaled with the degree of Zeb1 suppression, further supporting a causal link between the latter and the former. Interestingly, Zeb1 depletion did not affect cancer cell killing in vitro (FIG. 13C), implying that miR200c inhibits this response via a distinct mechanism. To assess the extent to which Zeb 1 inhibition accounts for in vivo anti-tumor responses, OT1 Cas9 CTLs were retrovirally transduced with a bicistronic vector expressing a miR (Scr or 200c) and a gRNA (Zeb1-CR1 or nontargeting (NT) control). This design permits comparison of the activity of miR200c and Zeb1 deficient CTLs against the same shared control. Both groups of cells enhanced anti-tumor function to a similar extent (FIG. 5G), strongly suggesting that Zeb1 inhibition accounts for most, if not all, of the therapeutic benefit conferred by miR200c.

miR200c CTLs also exhibited marked upregulation of the aryl hydrocarbon receptor (AhR) (FIG. 14A), a transcription factor that has been implicated in the differentiation of both T cells and B cells. This phenotype was Zeb1 independent, as it was not recapitulated in Zeb1 deficient CTLs (FIG. 14A). Interestingly, ectopic expression of AhR inhibited CTL-mediated killing in vitro, suggesting that the AhR branch of the miR200c network, rather than the Zeb1 branch, regulates cytotoxicity (FIGS. 14A-14B). AhR overexpression had no effect on in vivo anti-tumor responses (FIG. 14C), however, indicating it is dispensable for miR200c-induced potentiation of ACT. Consistent with this interpretation, homozygous deletion of the Ahr gene did not alter the capacity of miR200c to enhance CTL anti-tumor function (FIG. 11D). Hence, unlike Zeb 1, AhR does not appear to play a therapeutically relevant role in CTLs downstream of miR200c.

Example 7: EpCAM Overexpression Recapitulates the Effects of miR200c

Figure 6A:
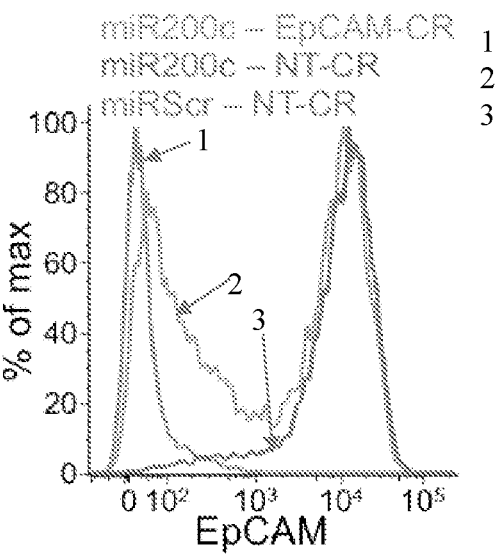
FIGS. 6A-6C show that EpCAM is required for miR200c dependent CTL enhancement.
Figure 6B:
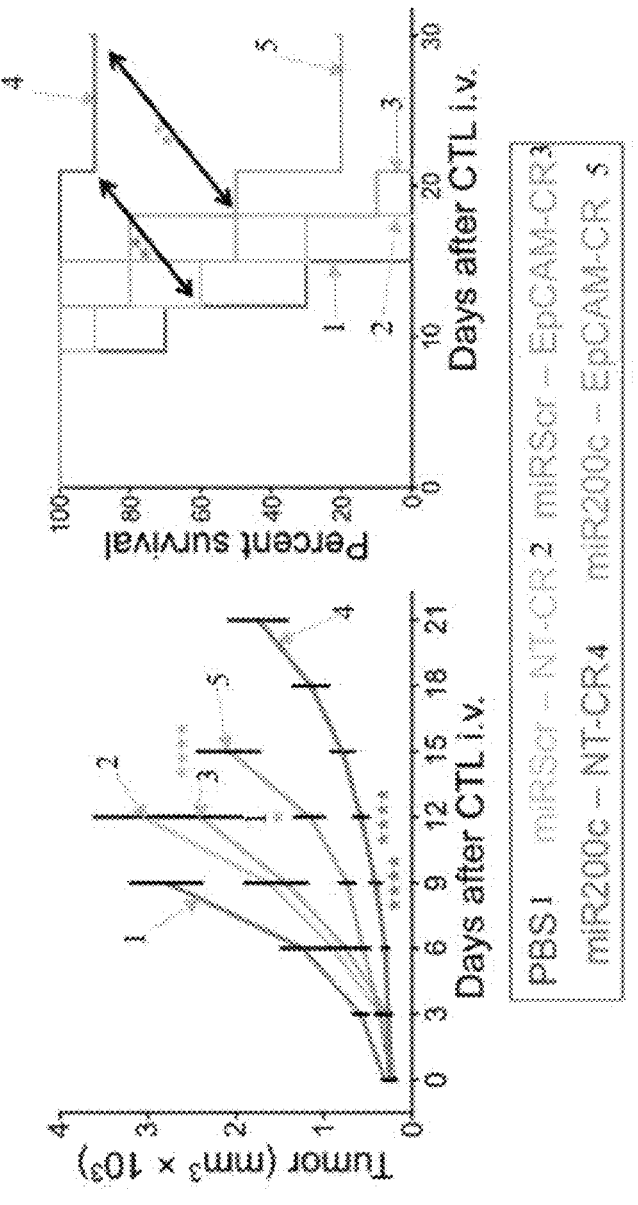
Figure 6C:
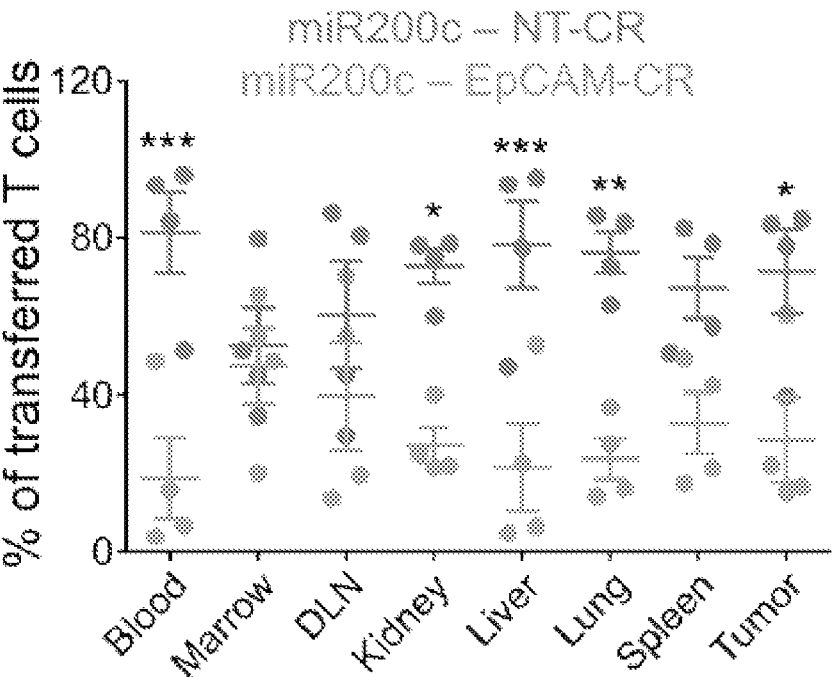
Figure 7A:
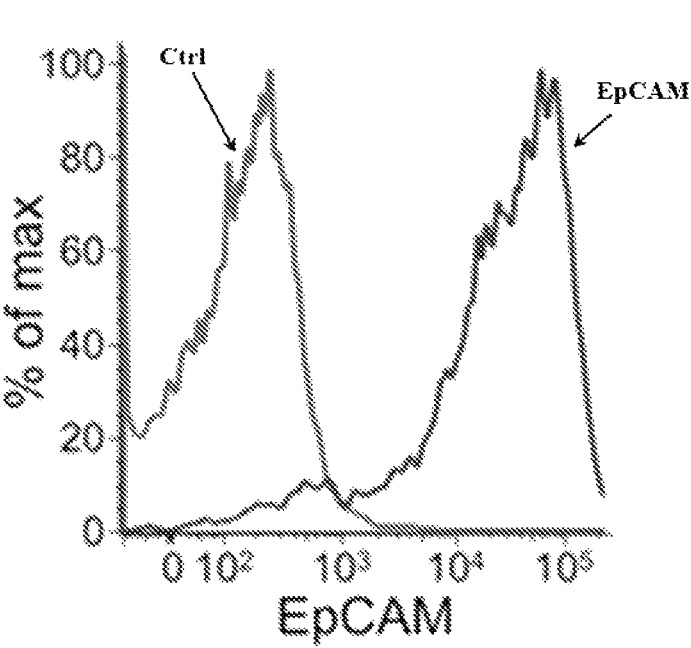
FIGS. 7A-7H show that EpCAM enhances CTL persistence and anti-tumor ACT.
Figure 7B:
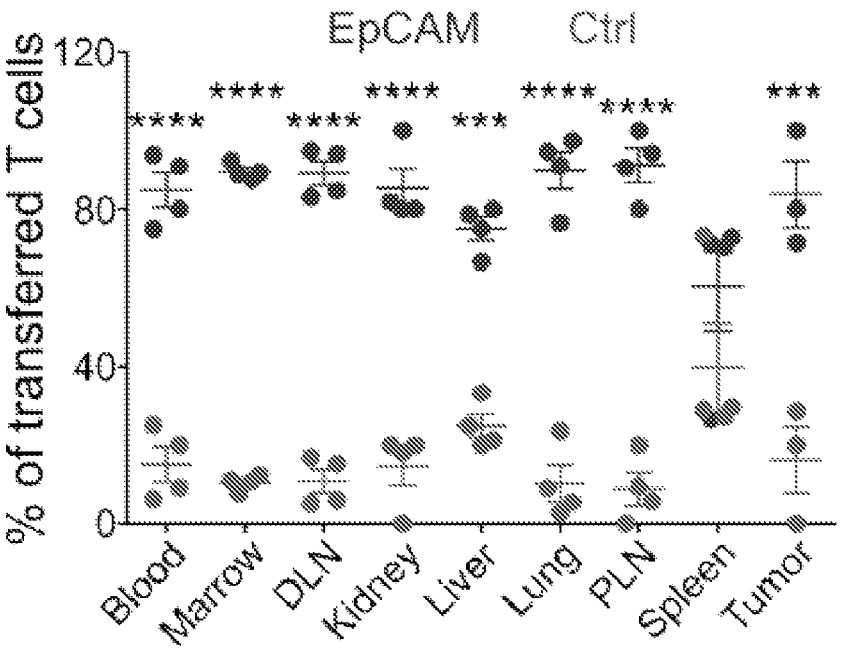
Figure 7C:
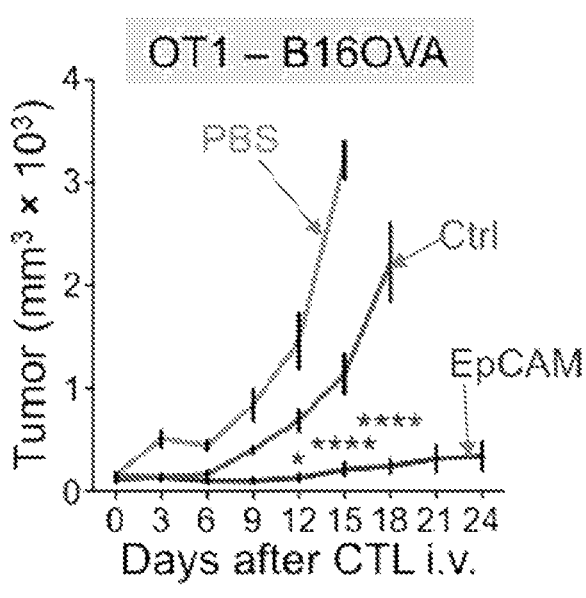
Figure 7C:
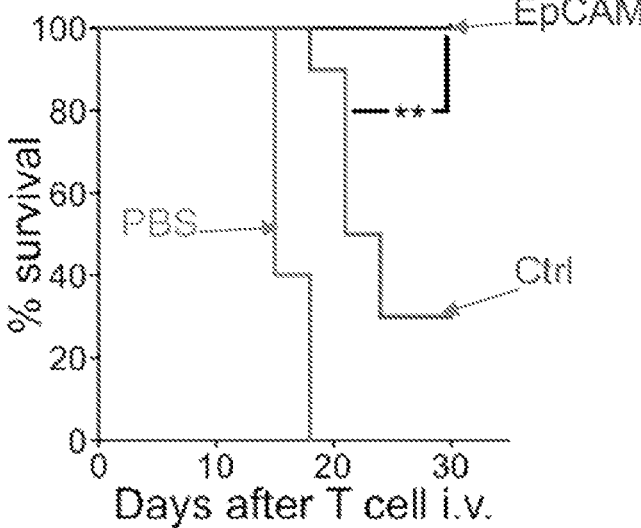
Figure 7D:
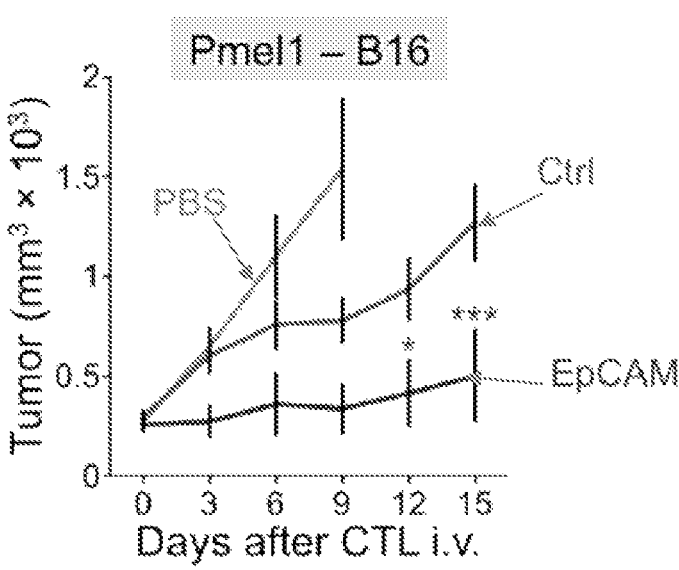
Figure 7D:
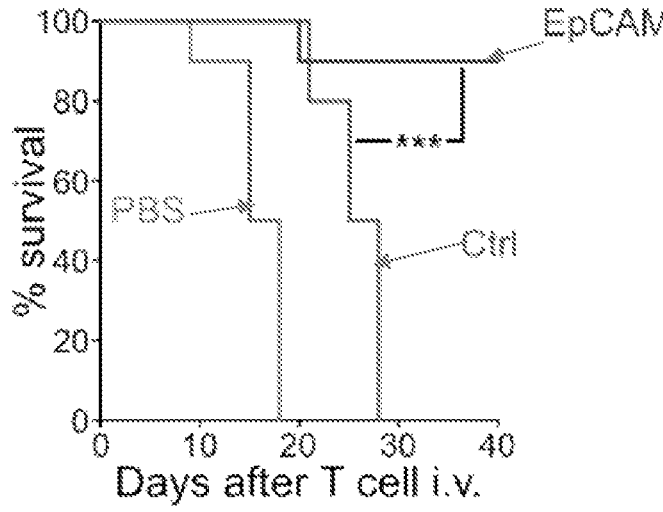
Figure 7E:
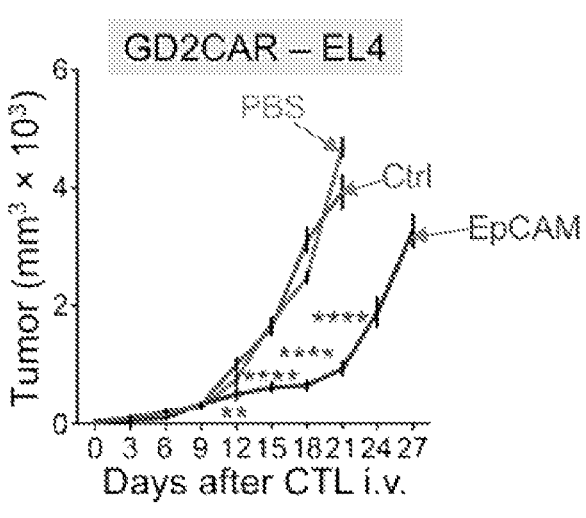
Figure 7E:
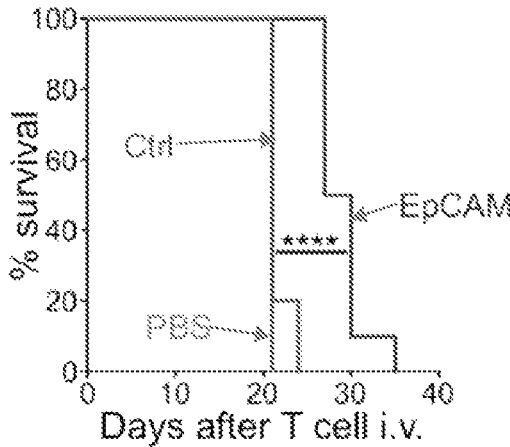
Figure 7F:
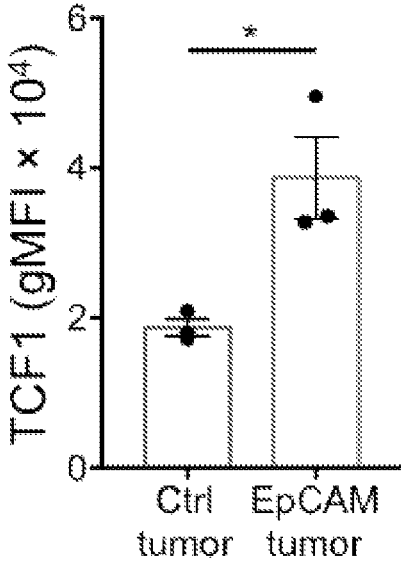
Figure 7G:
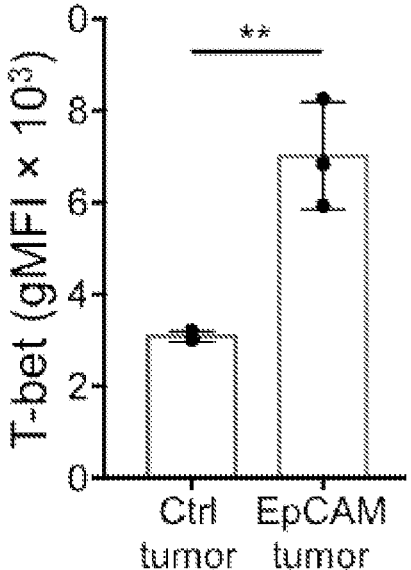
Figure 7H:
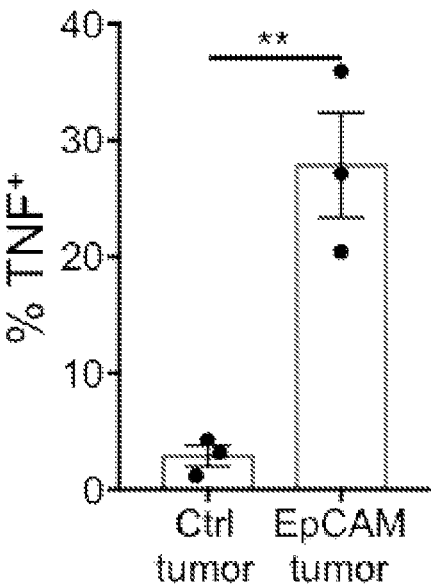
Figure 15A:
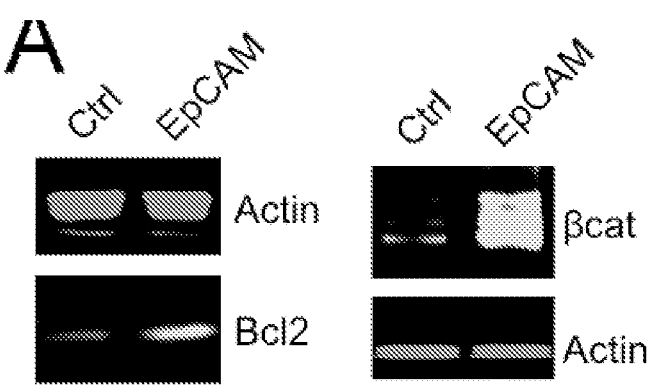
FIGS. 15A-15F show that EpCAM enhances CTL survival, functionality, and anti-tumor ACT. Related to FIGS.
Figure 15B:
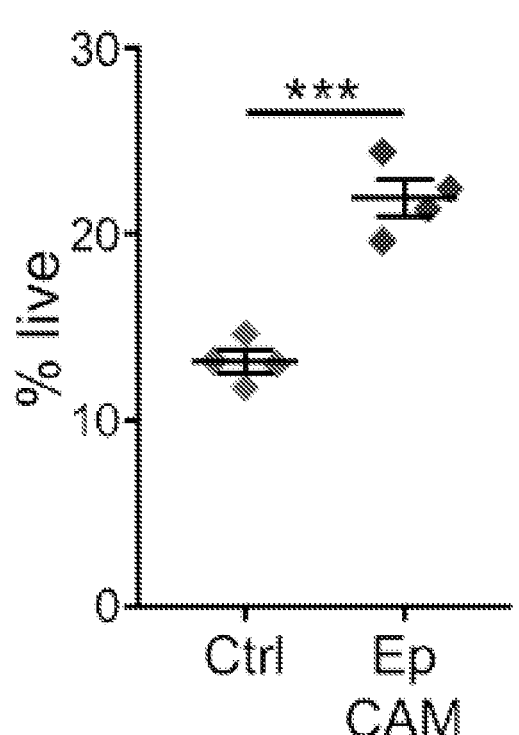
Figure 15C:
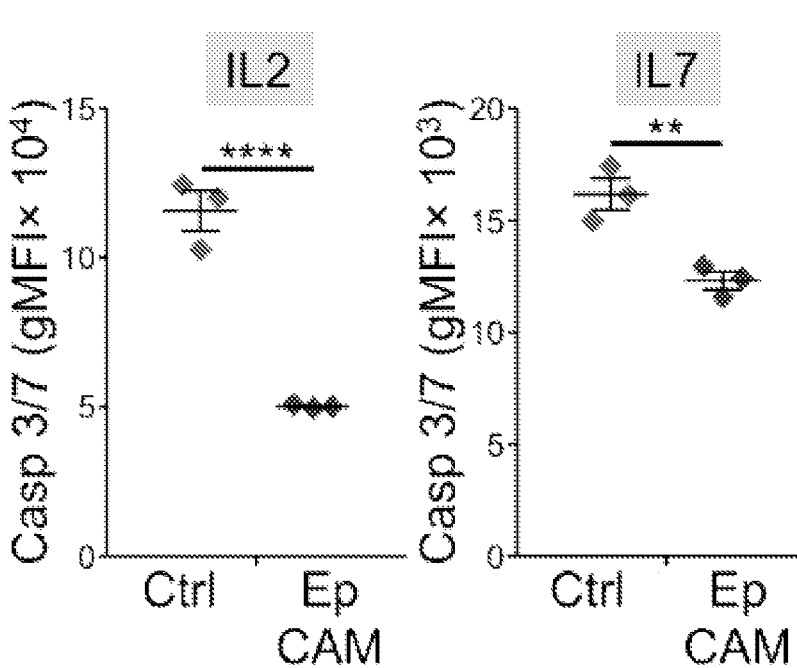
Figure 15D:
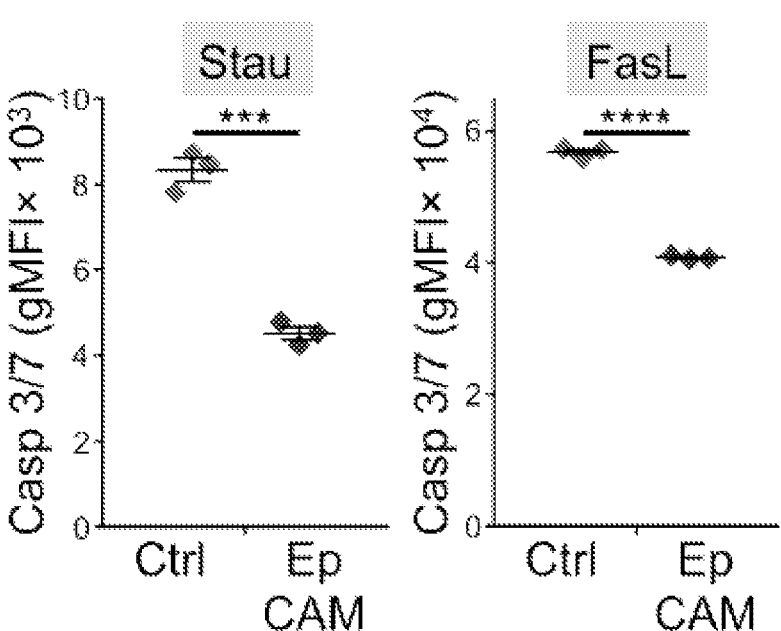
Figure 15E:
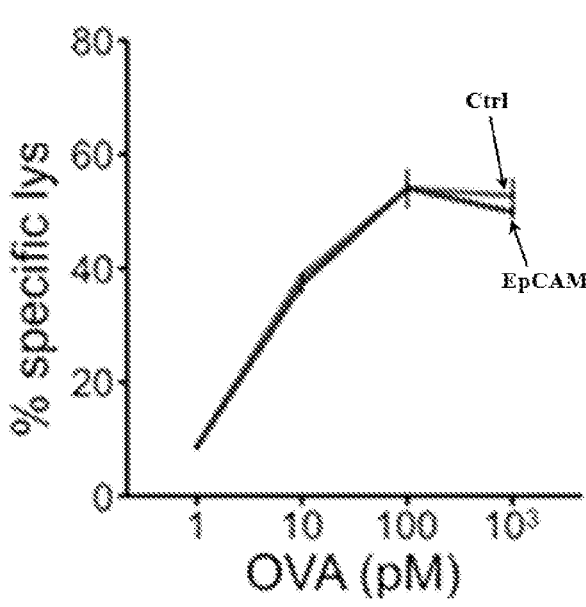

The capacity of Zeb 1 deletion to phenocopy the effects of miR200c in CTLs prompted the exploration of potential roles for Zeb1 target genes. Using CRISPR/Cas9 targeting, the upregulation of EpCAM induced by miR200c overexpression was partially reversed (FIG. 6A). Remarkably, miR200c OT1 CTLs lacking EpCAM were significantly less effective than their EpCAM sufficient counterparts at suppressing B16OVA tumors (FIG. 6B). EpCAM was also required for the potentiation of in vivo persistence by miR200c (FIG. 6C). To determine whether EpCAM alone was sufficient to enhance therapeutic T cell function, CTLs were retrovirally transduced with full-length EpCAM fused to GFP (FIG. 7A). Ectopic EpCAM expression increased the persistence of transferred CTLs in vivo, similar to the effects of miR200c overexpression and Zeb 1 deletion (FIG. 7B). CTLs transduced with EpCAM (EpCAM-CTLs) also exhibited higher levels of Bc12 and β-catenin in vitro, along with enhanced survival and reduced apoptosis (FIGS. 15A-15D). As with Zeb 1 deletion, EpCAM transduction did not alter cytotoxicity (FIG. 15E). Importantly, EpCAM CTLs conferred more effective tumor suppression than controls in both TCR-driven (OT1-B16OVA and Pmel 1-B16) and CAR-driven (GD2CAR-EL4) solid tumor models of ACT (FIGS. 7C-7E). This augmented in vivo functionality was associated with increased TCF1, T-bet, and TNF expression in tumor infiltrating CTLs (FIGS. 7F-7H).

Figure 15F:
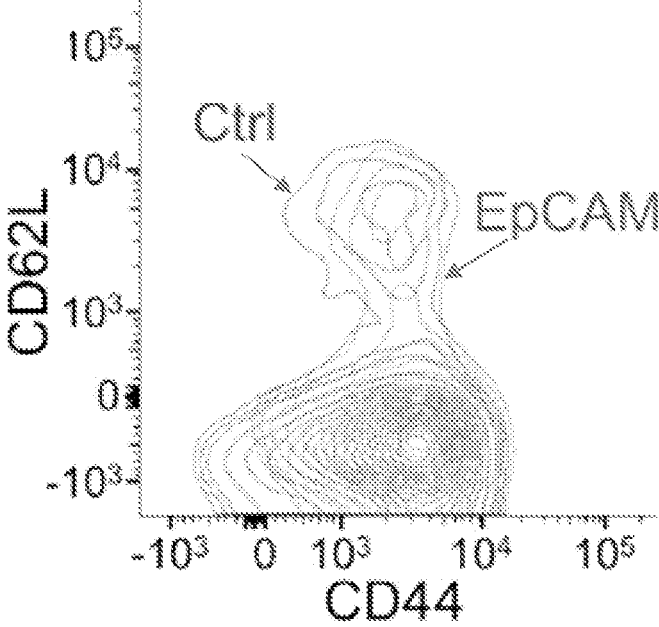
Figure 16A:
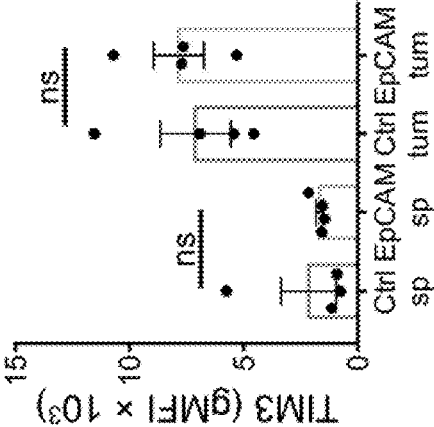
FIGS. 16A-16C show that EpCAM does not alter the expression of exhaustion markers. Related to FIGS. 7A-7H and FIGS. 8A-8F.
Figure 16A:
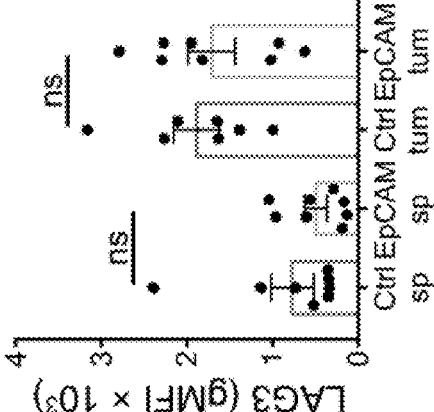
Figure 16A:
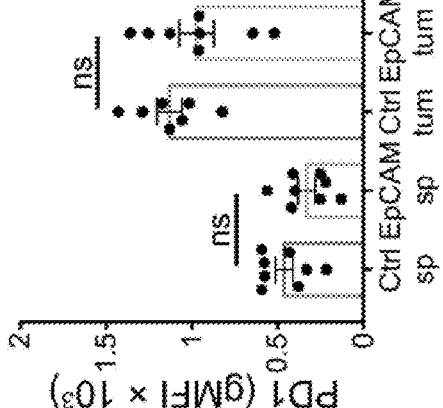

By contrast, EpCAM overexpression had no effect on cell surface levels of PD1, LAG3, and TIM3 (FIG. 16A). Finally, EpCAM CTLs were CD44$^{hi}$ and CD62$^{lo}$, similar to miR200c CTLs and unlike Tscm cells (FIG. 15F). Collectively, these results indicate that EpCAM recapitulates critical features of the miR200c CTL phenotype.

Figure 17:
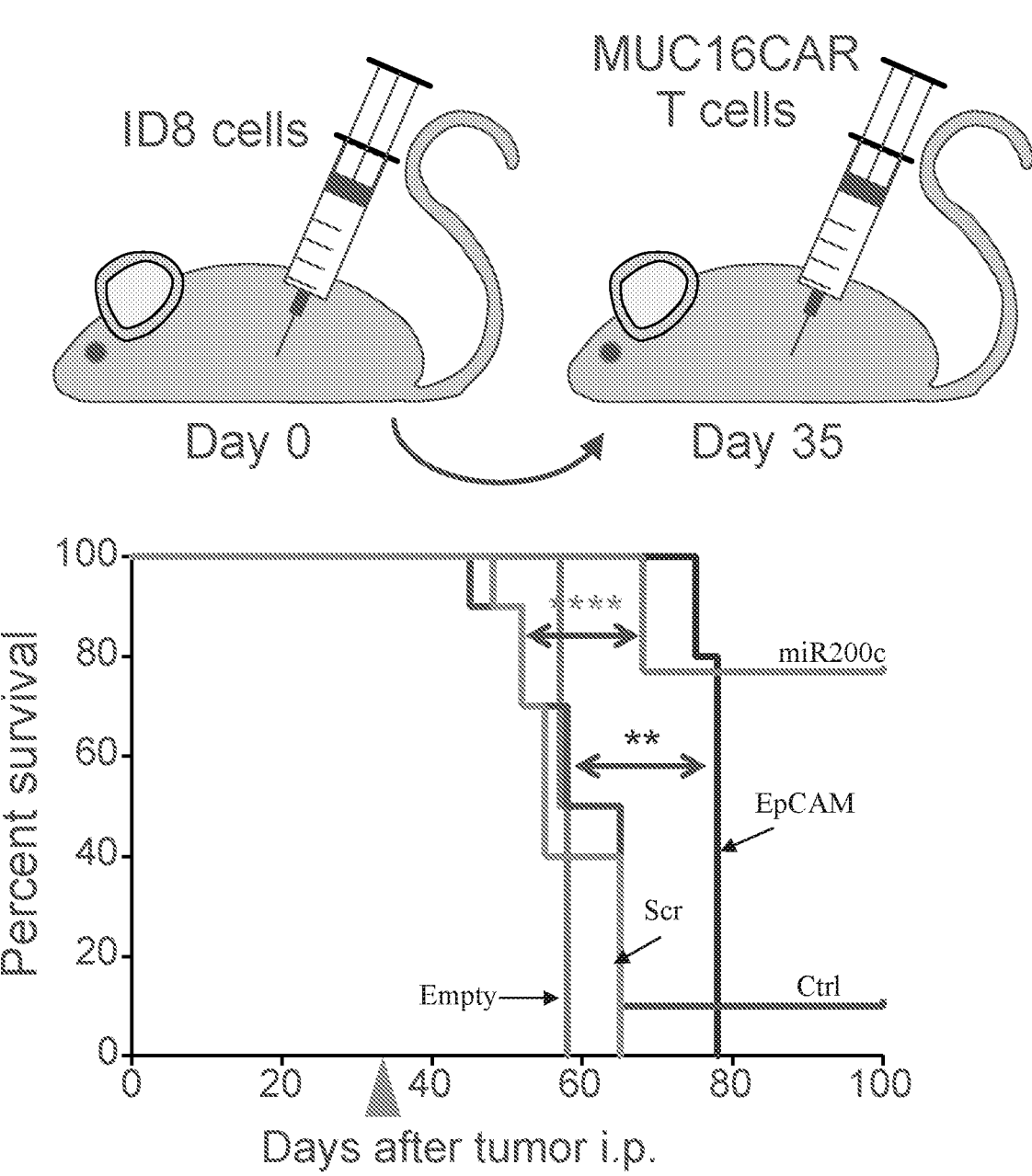
FIG. 17 shows the impact of administering CTLs expressing EpCAM, miR200c, scrambled miR or empty vector (Ctrl) together with MUC16 CAR on survival in mice bearing IDB orthotopic ovarian tumors.

Tumor bearing mice were prepared by intraperitoneally (i.p.) injecting C57BL/6 animals with $1 \times 10^7$ ID8 ovarian cancer cells expressing the retained domain of MUC16 along with luciferase. 35 days later, $2 \times 10^6$ CAR T cells were injected i.p. and subsequent tumor growth was monitored by bioluminescence imaging once a week for up to 3 months. Peritoneal ID8 cells colonized the intestine, liver, pancreas, kidneys, and abdominal wall, leading to the production of ascites fluid that swells the abdomen. Animals were sacrificed when abdominal swelling was observed. Therapeutic T cells expressing miR200c and MUC16 CAR were compared with T cells expressing miRScr (a scrambled miR control) and MUC16CAR. In parallel, T cells expressing EpCAM-GFP and MUC16CAR were compared with T cells expressing GFP (control) and MUC16CAR. FIG. 17 demonstrates that animals bearing orthotopic ovarian tumors receiving miR200c or EpCAM overexpressing CTLs comprising MUC16 CAR T cells showed a significantly higher degree of survival relative to scrambled miR or GFP control CTLs comprising MUC16 CAR T cells.

Figure 8A:
FIGS. 8A-8F show that EpCAM promotes CD19CAR ACT of B cell leukemia. NSG mice bearing NALM6 tumors were injected with human CD19CAR T cells expressing EpCAM or CD271 (Ctrl).
Figure 8A:
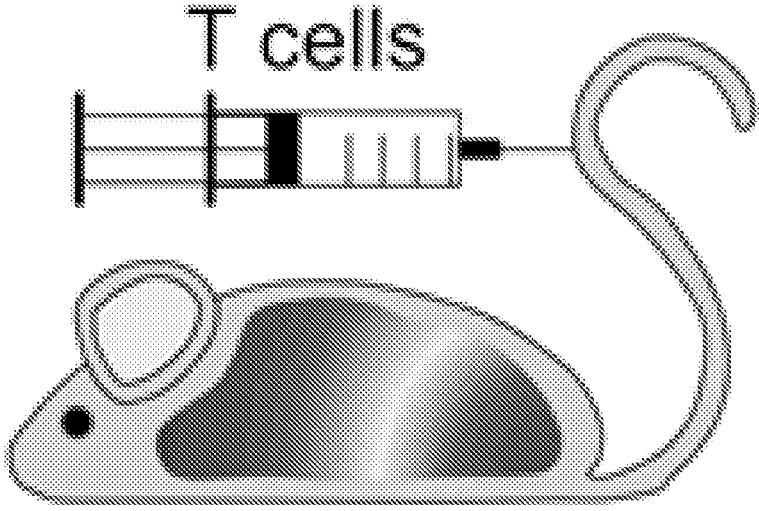
Figure 8B:
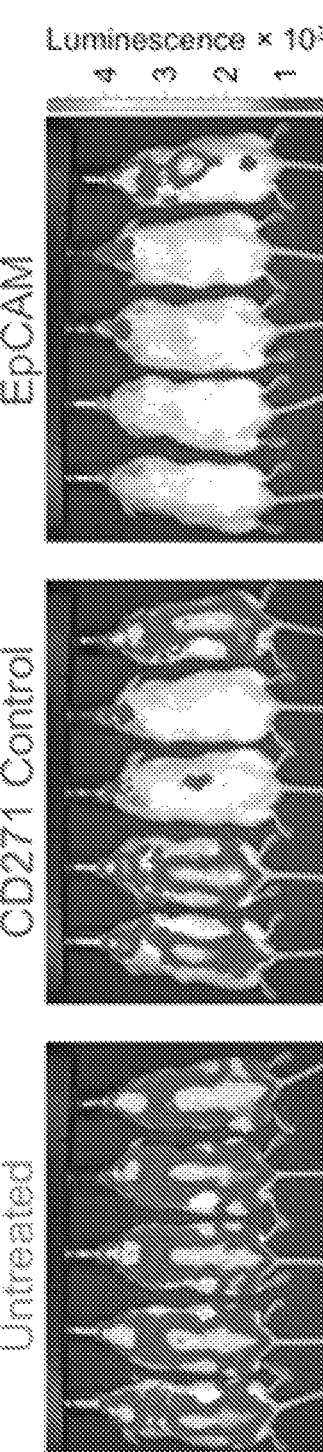
Figure 8C:
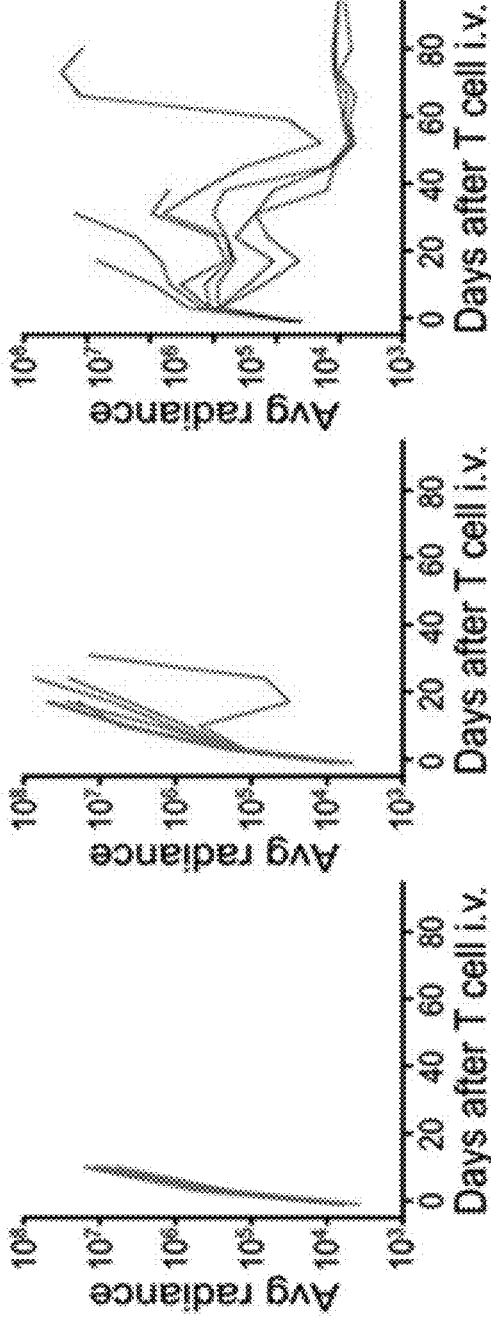
Figure 8D:
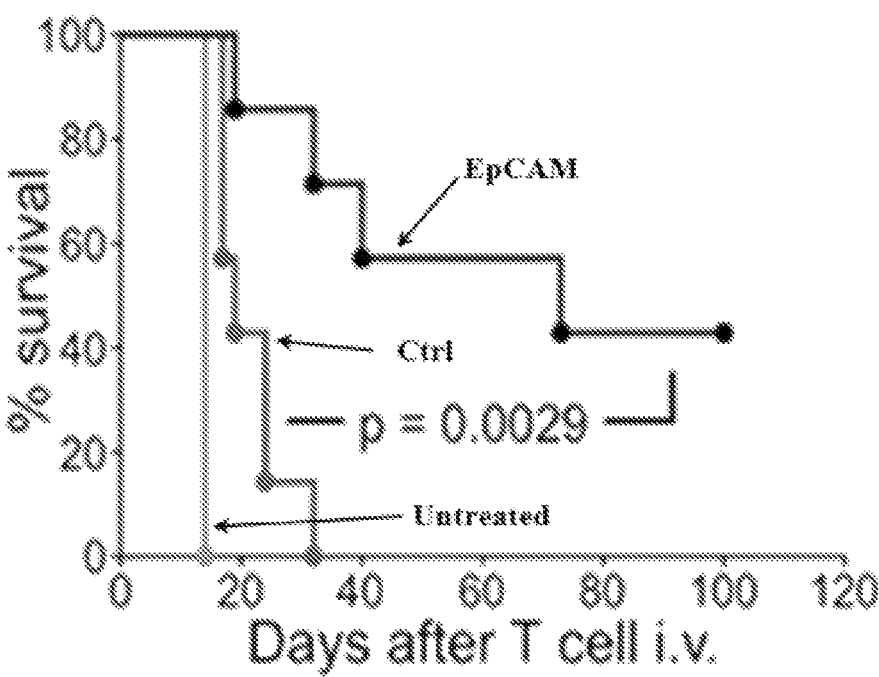
Figure 8E:
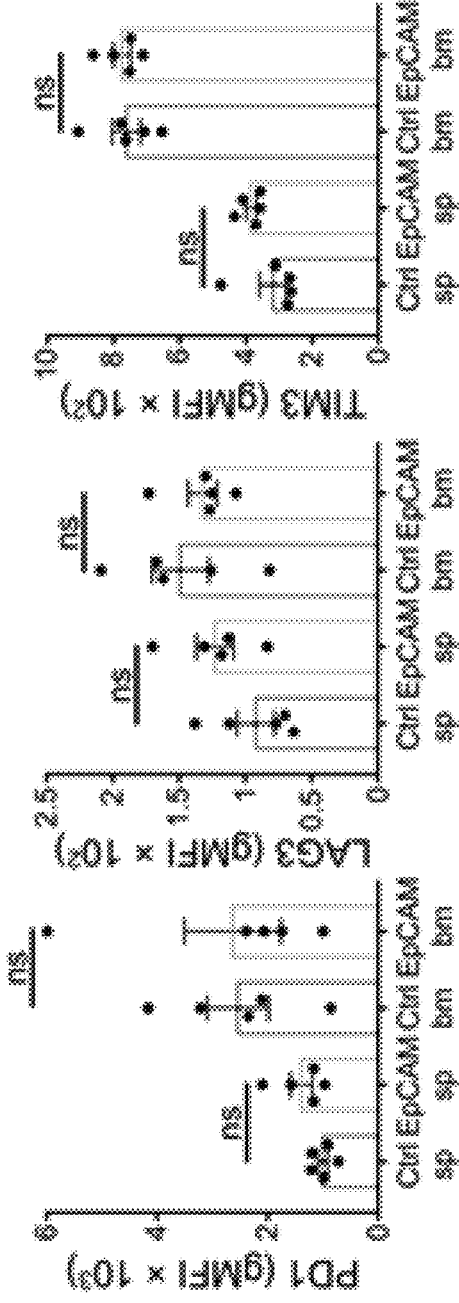
Figure 8F:
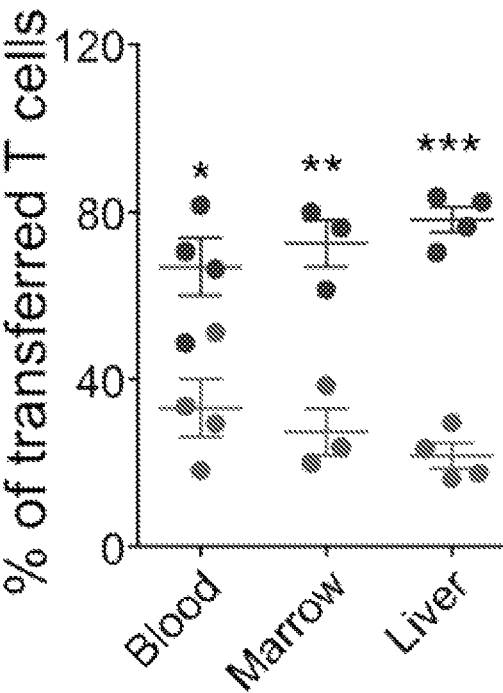
Figure 16B:
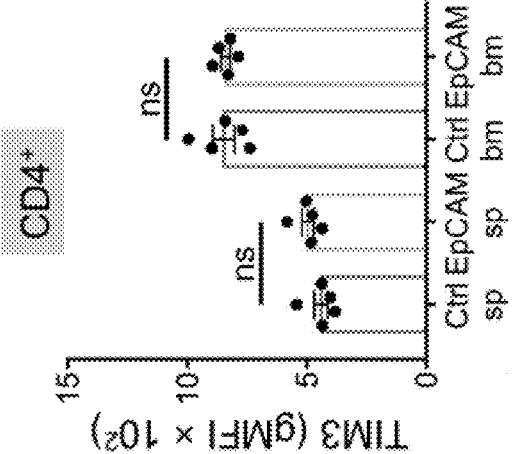
Figure 16B:
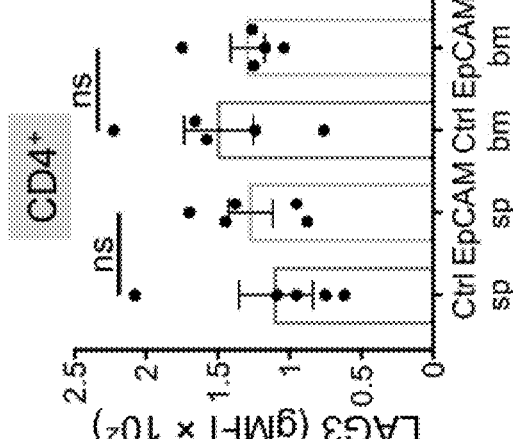
Figure 16B:
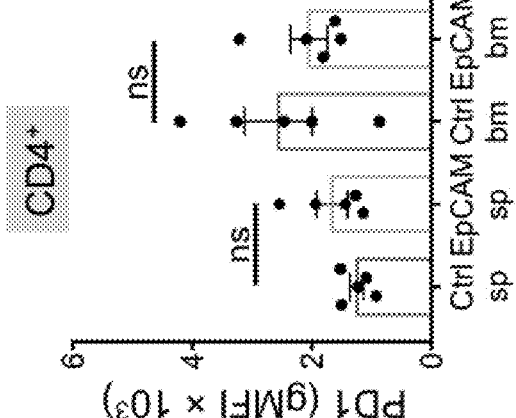
Figure 16C:
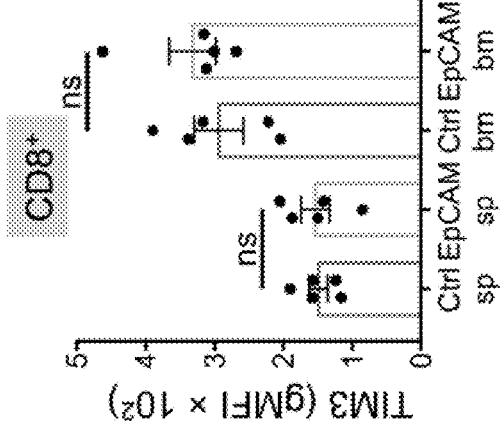
Figure 16C:
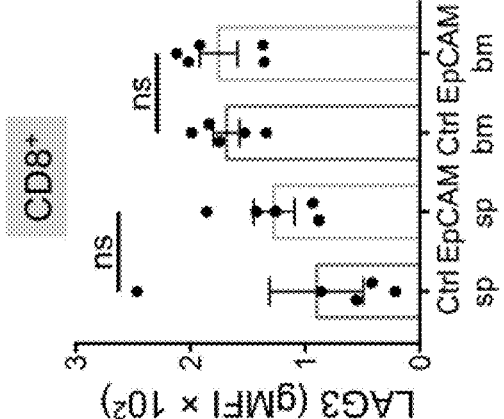
Figure 16C:
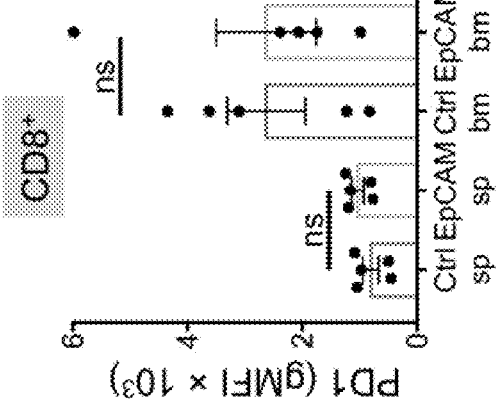

Finally, the capacity of EpCAM to potentiate therapeutic T cell responses against liquid tumors was assessed using an established system in which human T cells expressing a CAR against the B cell antigen CD19 are used to treat NOD-scid il2rg–/– (NSG) mice injected with NALM6 B cell leukemia (FIG. 8A). EpCAM overexpression enhanced tumor suppression in this model (FIGS. 8B-8C), leading to a significant increase in survival (FIG. 8D). Comparative analysis of EpCAM and control CAR T cells extracted from the spleen and bone marrow 17 days after infusion revealed no differences in the expression of PD1, LAG3, and TIM3 (FIG. 8E and FIGS. 16B-16C), implying that the enhanced activity of EpCAM T cells in this model did not result from suppressed exhaustion. The effects of EpCAM on CAR T cell persistence were also examined by injecting NALM6-bearing NSG mice with a 1:1 mixture of EpCAM and control CAR T cells. After seven days, EpCAM T cells were significantly over-represented in the blood, bone marrow, and liver (FIG. 8F), suggesting that EpCAM transduction boosts the engraftment and persistence of human T cells, as well. These results demonstrate that modulation of the miR200c-EpCAM axis improves ACT against both solid and liquid malignancies.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. An engineered immune cell comprising a non-endogenous expression vector comprising the miR200c nucleic acid sequence of SEQ ID NO: 25 and a non-endogenous expression vector comprising the EpCAM nucleic acid sequence of SEQ ID NO: 27 or a nucleic acid encoding the EpCAM polypeptide of SEQ ID NO: 29 wherein the engineered immune cell is a lymphocyte, a myeloid cell, a T cell, a B cell, a tumor infiltrating lymphocyte, or a natural killer cell and wherein the engineered immune cell is from an autologous donor or an allogenic donor.

2. The engineered immune cell of claim 1, wherein the miR200c nucleic acid sequence and the EpCAM nucleic acid sequence are in the same non-endogenous vector, or wherein the non-endogenous expression vector comprising the miR200c nucleic acid sequence is distinct from the non-endogenous expression vector comprising the EpCAM nucleic acid sequence.

3. The engineered immune cell of claim 1, wherein the non-endogenous expression vector comprising the miR200c nucleic acid sequence or the non-endogenous expression vector comprising the EpCAM nucleic acid sequence is a plasmid, a cosmid, a bacmid, a bacterial artificial chromosome (BAC), a yeast artificial chromosome (YAC), a viral vector or a retroviral vector.

4. The engineered immune cell of claim 1, wherein the miR200c nucleic acid sequence or the EpCAM nucleic acid sequence is operably linked to an expression control sequence, selected from the group consisting of an inducible promoter, a constitutive promoter, an endogenous promoter, and a heterologous promoter.

5. The engineered immune cell of claim 1, wherein the non-endogenous vector comprising the miR200c nucleic acid sequence or the EpCAM nucleic acid sequence further comprises at least one of a bioluminescent protein, a fluorescent protein, a chemiluminescent protein, an epitope tag, or a selectable marker.

6. The engineered immune cell of claim 1, wherein the T cell is a CD8$^+$ cytotoxic T cell or a CD4$^+$ T cell.

7. The engineered immune cell of claim 6, wherein the T cell comprises a non-native TCR, or a chimeric antigen receptor (CAR).

8. A composition comprising an effective amount of the engineered immune cell of claim 1 and a pharmaceutically acceptable carrier.

* * * * *

SEQUENCE LISTING

<160> NUMBER OF SEQ ID NOS: 31

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ile Ile Asn Phe Glu Lys Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Gly Ser Arg Asn Gln Asp Trp Leu
1               5

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caccgacctg cccgtattgt gatag                                           25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaacctatca caatacgggc aggtc                                           25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
caccggtacc gccatgagaa gaacg                                           25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaaccgttct tctcatggcg gtacc                                                     25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
caccgggggc ggtgccaaga actgc                                                     25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaacgcagtt cttggcaccg ccccc                                                     25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caccggaatg ccagtgtact tccta                                                     25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aaactaggaa gtacactggc attcc                                                     25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caccgacgtg gggacatata cgtgt                                                     25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaacacacgt atatgtcccc acgtc                                                    25

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tttttggatc ctagtaggag gcttggtag                                               29

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tttttgaatt ctgtctacta ttctttccc                                               29

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tacaatactc gagatggcgg gtccccaggc cctc                                         34

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atagtttagc ggccgcggca ttaagctctc tgtgga                                       36

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aggcgccgga attagatctc atgagcagcg gcgccaacat c                                 41

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgcctcccct acccggtagt caactctgca ccttgcttag                                   40

```
<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtccctccat cattattagc agtattaaat ttccatcatt attagcagta ttag          54

<210> SEQ ID NO 20
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gaccctaata ctgctaataa tgatggaaat ttaatactgc taataatgat ggagg          55

<210> SEQ ID NO 21
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtcccctacc tgcactccga tgctctgtta tctacctgca ctccgatgct ctggg          55

<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaccccagag catcggagtg caggtagata acagagcatc ggagtgcagg tagg          54

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
accggtaggc ctcgtacgct ta          22

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tccacagggt cgaccactg          19
```

-continued

```
<210> SEQ ID NO 25
<211> LENGTH: 68
<212> TYPE: DNA
<213> ORGANISM: Homo sapiens

<400> SEQUENCE: 25
ccctcgtctt acccagcagt gtttgggtgc ggttgggagt ctctaatact gccgggtaat          60
gatggagg                                                                   68

<210> SEQ ID NO 26
<211> LENGTH: 69
<212> TYPE: DNA
<213> ORGANISM: Mus musculus

<400> SEQUENCE: 26
ccctcgtctt acccagcagt gtttgggtgc tggttgggag tctctaatac tgccgggtaa          60
tgatggagg                                                                  69

<210> SEQ ID NO 27
<211> LENGTH: 1547
<212> TYPE: DNA
<213> ORGANISM: Homo sapiens

<400> SEQUENCE: 27
acagagcgct agtccttcgg cgagcgagca ccttcgacgc ggtccgggga ccccctcgtc          60
gctgtcctcc cgacgcggac ccgcgtgccc caggcctcgc gctgcccggc cggctcctcg         120
tgtcccactc ccggcgcacg ccctccccgcg agtcccgggc ccctcccgcg ccctcttct         180 cggcgcgcgc gcagcatggc gcccccgcag gtcctcgcgt cgggcttct gcttgccgcg          240 gcgacggcga cttttgccgc agctcaggaa gaatgtgtct gtgaaaacta caagctggcc         300
gtaaactgct ttgtgaataa taatcgtcaa tgccagtgta cttcagttgg tgcacaaaat        360
actgtcattt gctcaaagct ggctgccaaa tgtttggtga tgaaggcaga aatgaatggc        420
tcaaaacttg ggagaagagc aaaacctgaa ggggccctcc agaacaatga tgggctttat       480
gatcctgact gcgatgagag cgggctcttt aaggccaagc agtgcaacgg cacctccatg        540
tgctggtgtg tgaacactgc tggggtcaga agaacagaca aggacactga ataacctgc         600 tctgagcgag tgagaaccta ctggatcatc attgaactaa aacacaaagc aagagaaaaa       660
ccttatgata gtaaaagttt gcggactgca cttcagaagg agatcacaac gcgttatcaa        720
ctggatccaa aatttatcac gagtattttg tatgagaata atgttatcac tattgatctg        780
gttcaaaatt cttctcaaaa aactcagaat gatgtggaca tagctgatgt ggcttattat        840
tttgaaaaag atgttaaagg tgaatccttg tttcattcta agaaaatgga cctgacagta        900 aatgggggaac aactggatct ggatcctggt caaactttaa tttattatgt tgatgaaaaa      960
gcacctgaat tctcaatgca gggtctaaaa gctggtgtta ttgctgttat tgtggttgtg     1020
gtgatagcag ttgttgctgg aattgttgtg ctggttattt ccagaaagaa gagaatggca     1080
aagtatgaga aggctgagat aaaggagatg ggtgagatgc atagggaact caatgcataa     1140
ctatataatt tgaagattat agaagaaggg aaatagcaaa tggacacaaa ttacaaatgt      1200
gtgtgcgtgg gacgaagaca tctttgaagg tcatgagttt gttagtttaa catcatatat     1260
ttgtaatagt gaaacctgta ctcaaaatat aagcagcttg aaactggctt taccaatctt     1320
gaaatttgac cacaagtgtc ttatatatgc agatctaatg taaaatccag aacttggact     1380
ccatcgttaa aattatttat gtgtaacatt caaatgtgtg cattaaatat gcttccacag     1440
```

-continued

```
taaaatctga aaaactgatt tgtgattgaa agctgccttt ctatttactt gagtcttgta    1500
catacatact tttttatgag ctatgaaata aaacatttta aactgaa                  1547

<210> SEQ ID NO 28
<211> LENGTH: 2061
<212> TYPE: DNA
<213> ORGANISM: Mus musculus

<400> SEQUENCE: 28
gcacttcttc cctctgatgg actgattctg cacgtgagac ctgcggcggc ggcggcggcg      60
gctgctgcag ctgcagctgc atgtttcact agaggaagtt ctcggtttga cttggtatcc     120
ctttcggctt tcacgtccag tctcgtccgt gtgtccgcga catccggtcc ttccgggta      180 ctggaatccc cgcctctggt ccgggacagc gcacacctgg agaggggggcg aggtggggcg     240 ggtgagtcac cgcgggcgag cgggcgggtg ggcgggcgag cggaggtgag ggcggggagg     300
ggcgtggccg gccgccgggg cagcagatcc gcaggtccgc tcccgcctcg ccgcgcgcac     360
agcgctcagt ccgtccgccg ccgcgcagcg cgactgtcct ccgagccgtc ccgcgccgca     420
cctccgcgag tcgccctcgc cgctccgcgc gcagcatggc gggtcccag gccctcgcgt      480 tcgggctcct gctcgcggtg gtcacagcga cgctggccgc ggctcagaga gactgtgtct     540
gtgacaacta caagctggca acaagttgct ctctgaatga atatggtgaa tgccagtgta     600
cttcctatgg tacacagaat actgtcattt gctccaaact ggcgtctaaa tgcttggcga     660
tgaaagcaga aatgactcac agcaagtctg ggaggaggag aaagcccgaa ggggcgatcc     720
agaacaacga tgggctgtac gacccccgact gcgacgagca ggggctcttc aaagccaagc     780
agtgcaacgg caccgccacg tgctggtgtg tcaacaccgc cggagtccga agaaccgaca     840
aggacacgga gatcacgtgc tccgagcgcg tgaggaccta ctggatcatc attgaactaa     900
aacacaaaga aagagaaagc ccctacgacc atcagagctt gcagactgcg cttcaagagg     960
cgttcacatc tcgatataag ctgaatcaga aatttatcaa aaacattatg tatgagaata    1020
atgttatcac cattgatctg atgcaaaact cttctcagaa aacacaagac gacgtggaca    1080
tagctgatgt ggcttactat tttgaaaaag atgtgaaggg ggagtccctg ttccattctt    1140
ctaagagcat ggacctgaga gtgaacggag agccgctcga tctggacccc gggcagactc    1200
tgatttacta cgttgatgaa aaggcacccg agttctccat gcagggcctc acggccggga    1260
tcatcgctgt cattgtggtg gtgtcattag cagtcatcgc ggggattgtt gtcctggtta    1320
tatctacaag gaagaaatca gcaaaatatg agaaggctga gataaaggag atgggtgaga    1380
tccacagaga gcttaatgcc tagccgtgct gagtgctgaa ctgaggaggg gccgcccgac    1440
cggaagtggc agaagagctc ggactgcaga tgtataaacc tggggaagat gaagacctgc    1500
gaagggttac tgctttgata gttactttgt tagtttcaca tttgtaacag tgaaatttgt    1560
actcgtaaat acaagcagct ggacaccggc attaccgatc gtaaaattag acgaacgtct    1620
tataggtgca ggtccagtgt ggtactcaga acttagcctg caaagttaag agagttgatg    1680
cttattatga cagagtgtgc gtcgcaaaca ttccaacagt agaatgcggt gactagtctc    1740
attttttttt ttttttgtg attaaggctg cccttctata tacctgagtc ttgtacataa    1800
taaacttttt tttaatgaaa taaaacattt taaagtgagt ttctaagttt gtttgaatca    1860
aattttccta gcatgtgcat aattaagata atagatgtct aaatgctctg gcactgctaa    1920
ctggtacaaa cctgtaattc tgtacttggg aggtagaggt aggagggtta gcgcttccga    1980
```
ggtagctgct gtgtatctgc tctgccactg actggccttg actatccaac accctatctg       2040
aaagaaataa aaatcaaact t                                                   2061

<210> SEQ ID NO 29
<211> LENGTH: 314
<212> TYPE: PRT
<213> ORGANISM: Homo sapiens

<400> SEQUENCE: 29

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Asn Arg Gln Cys Gln Cys
        35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
    130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
            195                 200                 205

Ile Ala Asp Val Ala Tyr Tyr Phe Glu Lys Asp Val Lys Gly Glu Ser
    210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270

Val Val Val Val Ile Ala Val Val Ala Gly Ile Val Val Leu Val Ile
        275                 280                 285

Ser Arg Lys Lys Arg Met Ala Lys Tyr Glu Lys Ala Glu Ile Lys Glu
    290                 295                 300

Met Gly Glu Met His Arg Glu Leu Asn Ala
305                 310

<210> SEQ ID NO 30
<211> LENGTH: 315
<212> TYPE: PRT
<213> ORGANISM: Mus musculus

<400> SEQUENCE: 30

-continued

```
Met Ala Gly Pro Gln Ala Leu Ala Phe Gly Leu Leu Leu Ala Val Val
1               5                   10                  15

Thr Ala Thr Leu Ala Ala Ala Gln Arg Asp Cys Val Cys Asp Asn Tyr
            20                  25                  30

Lys Leu Ala Thr Ser Cys Ser Leu Asn Glu Tyr Gly Glu Cys Gln Cys
        35                  40                  45

Thr Ser Tyr Gly Thr Gln Asn Thr Val Ile Cys Ser Lys Leu Ala Ser
    50                  55                  60

Lys Cys Leu Ala Met Lys Ala Glu Met Thr His Ser Lys Ser Gly Arg
65                  70                  75                  80

Arg Ile Lys Pro Glu Gly Ala Ile Gln Asn Asn Asp Gly Leu Tyr Asp
                85                  90                  95

Pro Asp Cys Asp Glu Gln Gly Leu Phe Lys Ala Lys Gln Cys Asn Gly
            100                 105                 110

Thr Ala Thr Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
    130                 135                 140

Ile Ile Glu Leu Lys His Lys Glu Arg Glu Ser Pro Tyr Asp His Gln
145                 150                 155                 160

Ser Leu Gln Thr Ala Leu Gln Glu Ala Phe Thr Ser Arg Tyr Lys Leu
            165                 170                 175

Asn Gln Lys Phe Ile Lys Asn Ile Met Tyr Glu Asn Asn Val Ile Thr
            180                 185                 190

Ile Asp Leu Met Gln Asn Ser Ser Gln Lys Thr Gln Asp Asp Val Asp
            195                 200                 205

Ile Ala Asp Val Ala Tyr Tyr Phe Glu Lys Asp Val Lys Gly Glu Ser
    210                 215                 220

Leu Phe His Ser Ser Lys Ser Met Asp Leu Arg Val Asn Gly Glu Pro
225                 230                 235                 240

Leu Asp Leu Asp Pro Gly Gln Thr Leu Ile Tyr Tyr Val Asp Glu Lys
            245                 250                 255

Ala Pro Glu Phe Ser Met Gln Gly Leu Thr Ala Gly Ile Ile Ala Val
            260                 265                 270

Ile Val Val Val Ser Leu Ala Val Ile Ala Gly Ile Val Val Leu Val
            275                 280                 285

Ile Ser Thr Arg Lys Lys Ser Ala Lys Tyr Glu Lys Ala Glu Ile Lys
    290                 295                 300

Glu Met Gly Glu Ile His Arg Glu Leu Asn Ala
305                 310                 315
```

```
<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 31

His His His His His His
1               5
```